United States Patent
Lin et al.

(10) Patent No.: US 10,787,666 B2
(45) Date of Patent: Sep. 29, 2020

(54) COMPOSITIONS AND METHODS FOR TREATING CANCER BY INHIBITING PIWIL4

(71) Applicant: ShanghaiTech University, Shanghai (CN)

(72) Inventors: Haifan Lin, New Haven, CT (US); Zifeng Wang, Shanghai (CN); Sanhong Liu, Shanghai (CN); Shuo Shi, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 16/469,816

(22) PCT Filed: Dec. 14, 2016

(86) PCT No.: PCT/CN2016/109858
§ 371 (c)(1),
(2) Date: Jun. 14, 2019

(87) PCT Pub. No.: WO2018/107381
PCT Pub. Date: Jun. 21, 2018

(65) Prior Publication Data
US 2019/0323011 A1    Oct. 24, 2019

(51) Int. Cl.
*A61K 48/00* (2006.01)
*C07H 21/04* (2006.01)
*C12N 15/113* (2010.01)
*C12Q 1/6886* (2018.01)

(52) U.S. Cl.
CPC .......... *C12N 15/113* (2013.01); *C12Q 1/6886* (2013.01); *C12N 2310/14* (2013.01); *C12N 2310/531* (2013.01); *C12Q 2600/136* (2013.01); *C12Q 2600/158* (2013.01)

(58) Field of Classification Search
CPC ........................... A61K 31/713; C12N 15/113
See application file for complete search history.

(56) References Cited

U.S. PATENT DOCUMENTS

| 2003/0232442 A1 | 12/2003 | Dobie |
| 2011/0287968 A1* | 11/2011 | Weinhausel ......... C12Q 1/6886 506/9 |
| 2014/0199415 A1* | 7/2014 | Westermarck ....... A61K 31/436 424/649 |

FOREIGN PATENT DOCUMENTS

| CN | 104099333 A | 10/2014 |
| WO | WO-2007/048629 A2 | 5/2007 |

OTHER PUBLICATIONS

International Search Report and Written Opinion dated Sep. 6, 2017 for International Application No. PCT/CN2016/109858, filed Dec. 14, 2016.
Wang, Z.F. et al. "The Rose of PIWIL4, an Argonaute Family Protein, in Breast Cancer" The Journal of Biological Chemistry, vol. 291, No. 20, May 13, 2016 (May 13, 2016), 10646-10658.
Su, C. et al. "PIWIL4 regulates cervical cancer cell line growth and is involved in down-regulating the expression of p14ARF and p53", FEBS Letters, vol. 586, Mar. 31, 2012 (Mar. 31, 2012), 1356-1362.
Chen, C. et al. " Overexpression of PIWI proteins in human stage III epithelial ovarian cancer with lymph node metastasis" Cancer Biomarkers, vol. 13, No. 5, Dec. 24, 2013 (Dec. 24, 2013), 315-321.
Navarro, A. et al. "The significance of PIWI family expression in human lung embryogenesis and non-small cell lung cancer" Oncotarget, vol. 6, No. 31, Jan. 23, 2015 (Jan. 23, 2015), 31544-31556.

* cited by examiner

*Primary Examiner* — Amy H Bowman
(74) *Attorney, Agent, or Firm* — Muriel Liberto, Esq.; Mintz Levin Cohn Ferris Glovsky and Popeo, P.C.

(57) ABSTRACT

Provided methods for diagnosing and treating cancer by reducing the biological activity and/or expression of P-element induced wimpy testis-like protein 4 (PIWIL4), and related compositions and methods.

6 Claims, 27 Drawing Sheets

Specification includes a Sequence Listing.

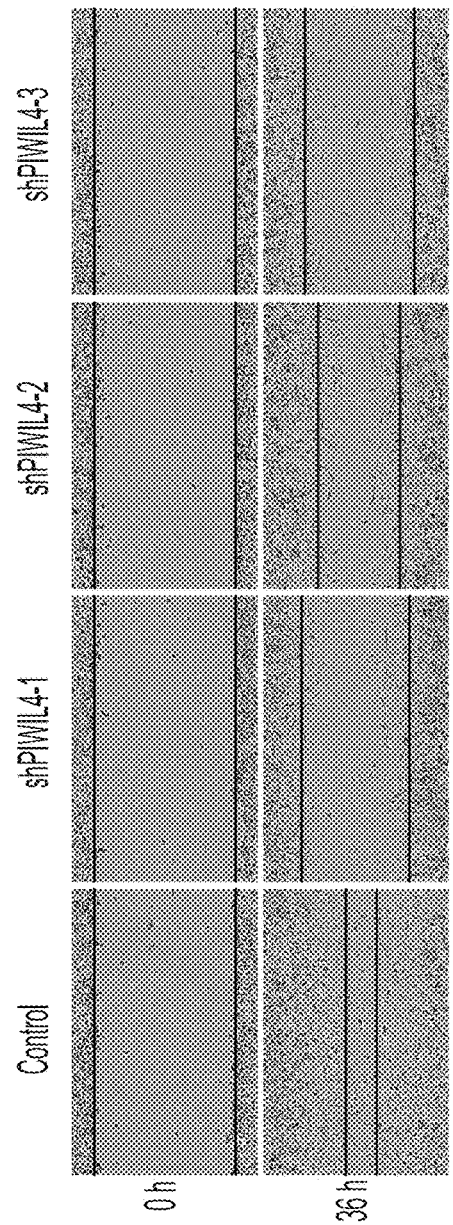
FIG. 4G
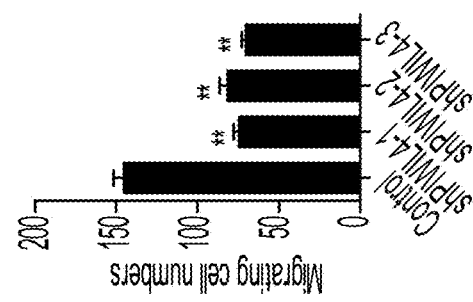
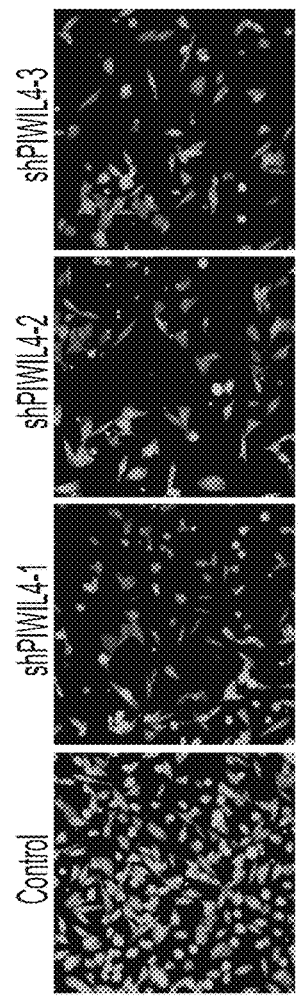
FIG. 4H

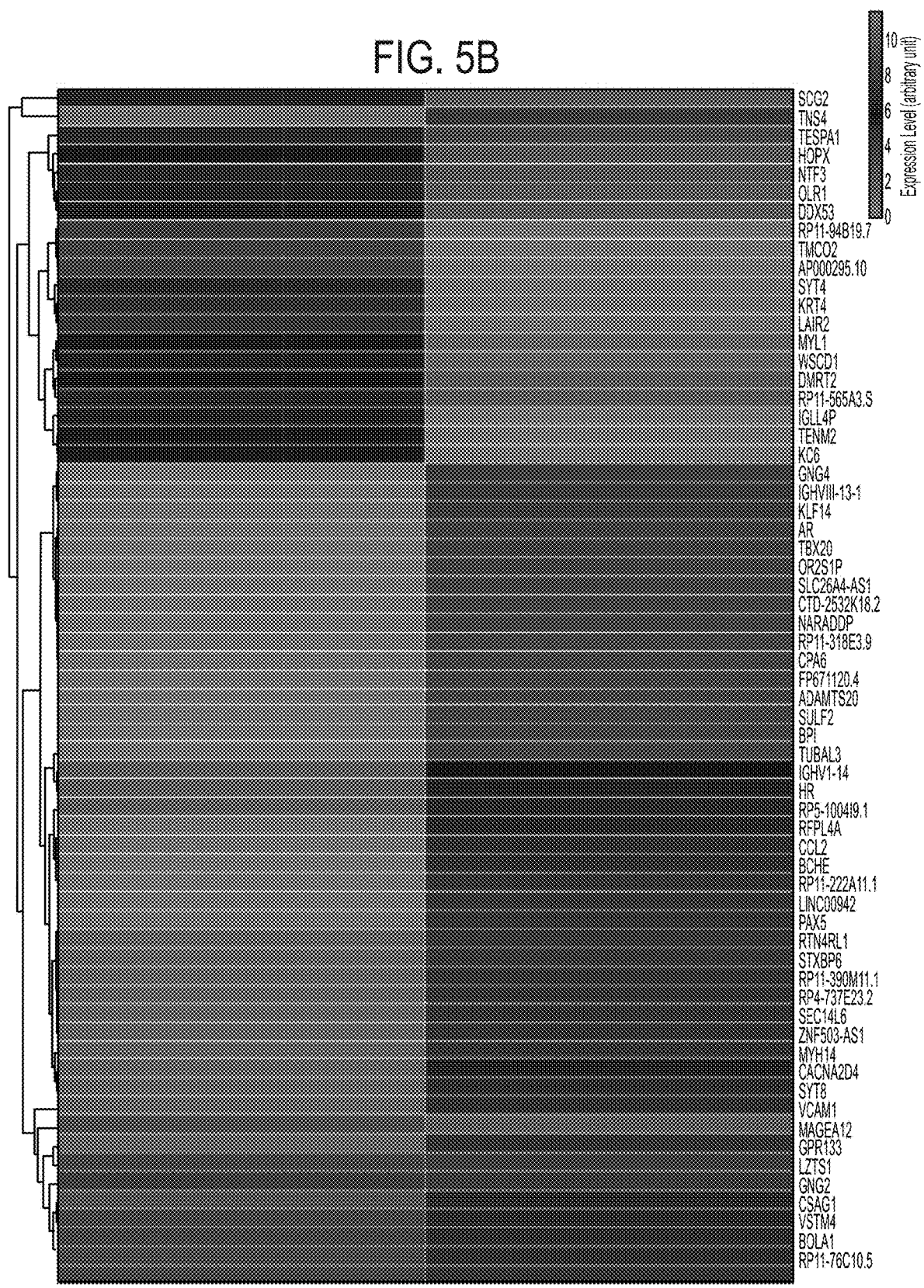

☐ 5397 proteins in MDA-MB-231 without shPIWIL4
☐ 2571 proteins common in three MDA-MB-231 with shPIWIL4
☐ 7094 total proteins in three MDA-MB-231 with shPIWIL4

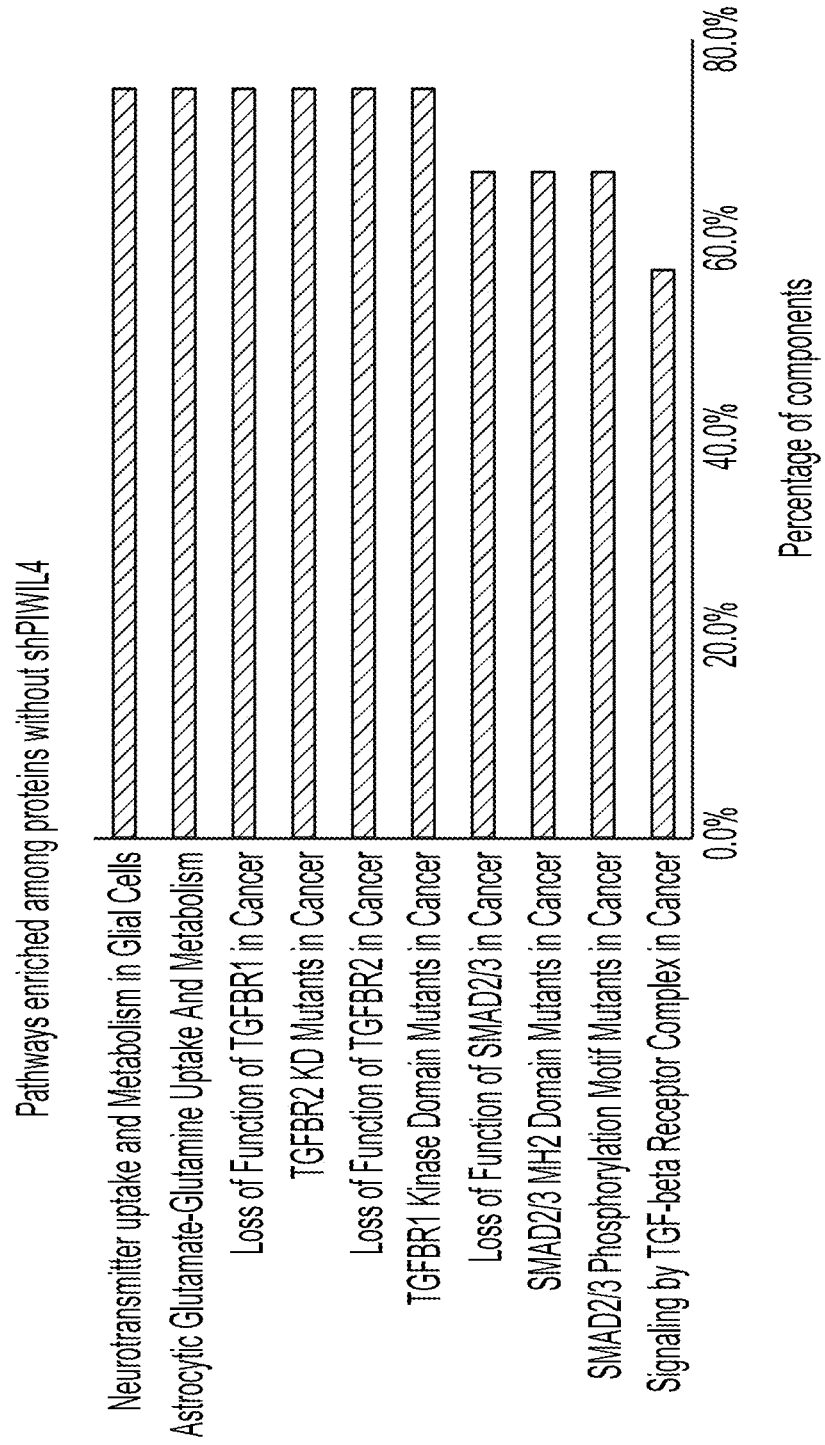

FIG. 6D
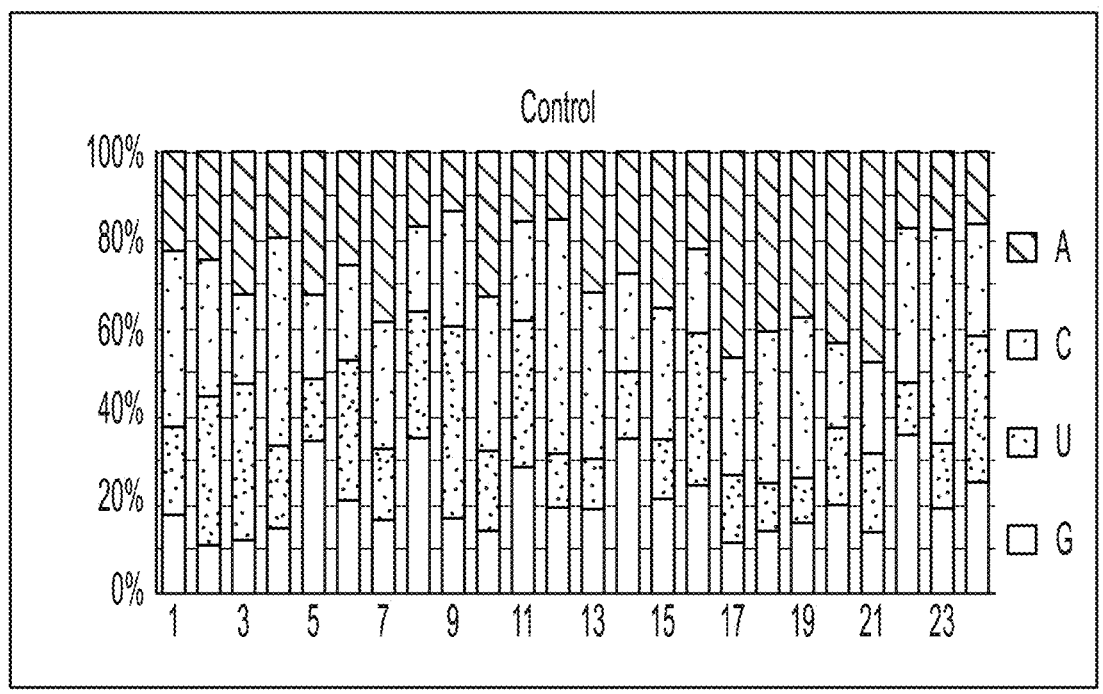
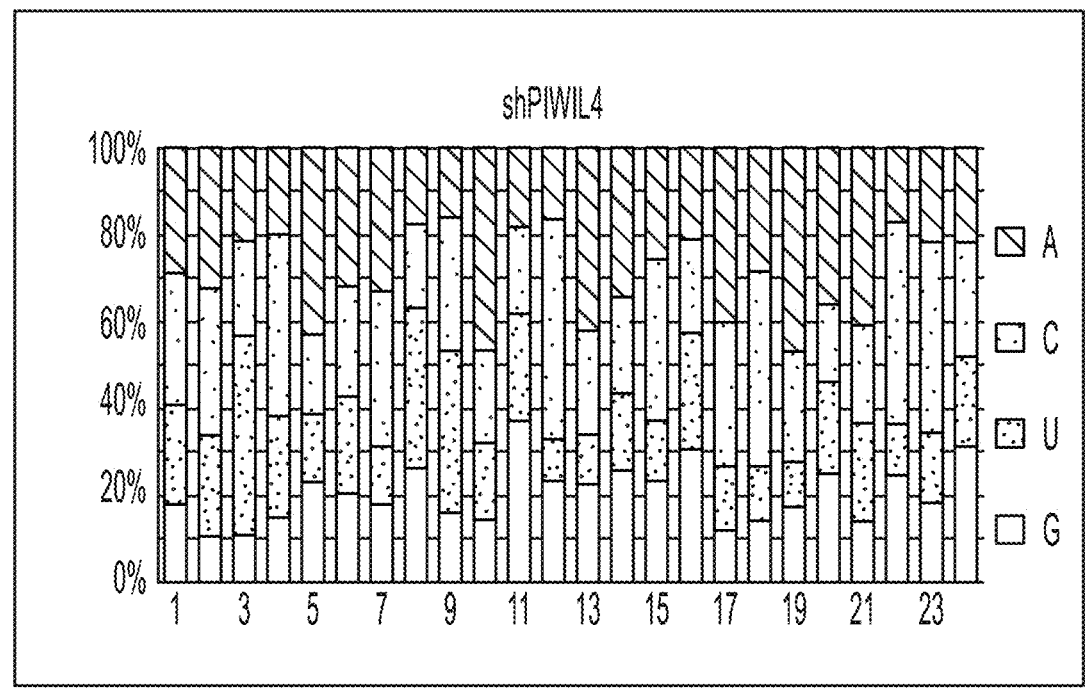

SEQUENCE LISTING

```
<160> NUMBER OF SEQ ID NOS: 89

<210> SEQ ID NO 1
<211> LENGTH: 852
<212> TYPE: PRT
<213> ORGANISM: Homo sapiens

<400> SEQUENCE: 1

Met Ser Gly Arg Ala Arg Val Lys Ala Arg Gly Ile Ala Arg Ser Pro
1               5                   10                  15

Ser Ala Thr Glu Val Gly Arg Ile Gln Ala Ser Pro Leu Pro Arg Ser
            20                  25                  30

Val Asp Leu Ser Asn Asn Glu Ala Ser Ser Ser Asn Gly Phe Leu Gly
        35                  40                  45

Thr Ser Arg Ile Ser Thr Asn Asp Lys Tyr Gly Ile Ser Ser Gly Asp
    50                  55                  60

Ala Gly Ser Thr Phe Met Glu Arg Gly Val Lys Asn Lys Gln Asp Phe
65                  70                  75                  80

Met Asp Leu Ser Ile Cys Thr Arg Glu Lys Leu Ala His Val Arg Asn
                85                  90                  95

Cys Lys Thr Gly Ser Ser Gly Ile Pro Val Lys Leu Val Thr Asn Leu
            100                 105                 110

Phe Asn Leu Asp Phe Pro Gln Asp Trp Gln Leu Tyr Gln Tyr His Val
        115                 120                 125

Thr Tyr Ile Pro Asp Leu Ala Ser Arg Arg Leu Arg Ile Ala Leu Leu
    130                 135                 140

Tyr Ser His Ser Glu Leu Ser Asn Lys Ala Lys Ala Phe Asp Gly Ala
145                 150                 155                 160

Ile Leu Phe Leu Ser Gln Lys Leu Glu Glu Lys Val Thr Glu Leu Ser
                165                 170                 175

Ser Glu Thr Gln Arg Gly Glu Thr Ile Lys Met Thr Ile Thr Leu Lys
```

```
              180                 185                 190
Arg Glu Leu Pro Ser Ser Ser Pro Val Cys Ile Gln Val Phe Asn Ile
            195                 200                 205
Ile Phe Arg Lys Ile Leu Lys Lys Leu Ser Met Tyr Gln Ile Gly Arg
210                 215                 220
Asn Phe Tyr Asn Pro Ser Glu Pro Met Glu Ile Pro Gln His Lys Leu
225                 230                 235                 240
Ser Leu Trp Pro Gly Phe Ala Ile Ser Val Ser Tyr Phe Glu Arg Lys
                245                 250                 255
Leu Leu Phe Ser Ala Asp Val Ser Tyr Lys Val Leu Arg Asn Glu Thr
            260                 265                 270
Val Leu Glu Phe Met Thr Ala Leu Cys Gln Arg Thr Gly Leu Ser Cys
        275                 280                 285
Phe Thr Gln Thr Cys Glu Lys Gln Leu Ile Gly Leu Ile Val Leu Thr
    290                 295                 300
Arg Tyr Asn Asn Arg Thr Tyr Ser Ile Asp Asp Ile Asp Trp Ser Val
305                 310                 315                 320
Lys Pro Thr His Thr Phe Gln Lys Arg Asp Gly Thr Glu Ile Thr Tyr
                325                 330                 335
Val Asp Tyr Tyr Lys Gln Gln Tyr Asp Ile Thr Val Ser Asp Leu Asn
            340                 345                 350
Gln Pro Met Leu Val Ser Leu Leu Lys Lys Arg Asn Asp Asn Ser
        355                 360                 365
Glu Ala Gln Leu Ala His Leu Ile Pro Glu Leu Cys Phe Leu Thr Gly
    370                 375                 380
Leu Thr Asp Gln Ala Thr Ser Asp Phe Gln Leu Met Lys Ala Val Ala
385                 390                 395                 400
Glu Lys Thr Arg Leu Ser Pro Ser Gly Arg Gln Gln Arg Leu Ala Arg
                405                 410                 415
Leu Val Asp Asn Ile Gln Arg Asn Thr Asn Ala Arg Phe Glu Leu Glu
            420                 425                 430
Thr Trp Gly Leu His Phe Gly Ser Gln Ile Ser Leu Thr Gly Arg Ile
        435                 440                 445
Val Pro Ser Glu Lys Ile Leu Met Gln Asp His Ile Cys Gln Pro Val
    450                 455                 460
Ser Ala Ala Asp Trp Ser Lys Asp Ile Arg Thr Cys Lys Ile Leu Asn
465                 470                 475                 480
Ala Gln Ser Leu Asn Thr Trp Leu Ile Leu Cys Ser Asp Arg Thr Glu
                485                 490                 495
Tyr Val Ala Glu Ser Phe Leu Asn Cys Leu Arg Arg Val Ala Gly Ser
            500                 505                 510
Met Gly Phe Asn Val Asp Tyr Pro Lys Ile Ile Lys Val Gln Glu Asn
        515                 520                 525
Pro Ala Ala Phe Val Arg Ala Ile Gln Gln Tyr Val Asp Pro Asp Val
    530                 535                 540
Gln Leu Val Met Cys Ile Leu Pro Ser Asn Gln Lys Thr Tyr Tyr Asp
545                 550                 555                 560
Ser Ile Lys Lys Tyr Leu Ser Ser Asp Cys Pro Val Pro Ser Gln Cys
                565                 570                 575
Val Leu Ala Arg Thr Leu Asn Lys Gln Gly Met Met Met Ser Ile Ala
            580                 585                 590
Thr Lys Ile Ala Met Gln Met Thr Cys Lys Leu Gly Gly Glu Leu Trp
        595                 600                 605
```

Ala Val Glu Ile Pro Leu Lys Ser Leu Met Val Val Gly Ile Asp Val
610             615                 620

Cys Lys Asp Ala Leu Ser Lys Asp Val Met Val Val Gly Cys Val Ala
625             630                 635                 640

Ser Val Asn Pro Arg Ile Thr Arg Trp Phe Ser Arg Cys Ile Leu Gln
            645                 650                 655

Arg Thr Met Thr Asp Val Ala Asp Cys Leu Lys Val Phe Met Thr Gly
                660                 665                 670

Ala Leu Asn Lys Trp Tyr Lys Tyr Asn His Asp Leu Pro Ala Arg Ile
            675                 680                 685

Ile Val Tyr Arg Ala Gly Val Gly Asp Gly Gln Leu Lys Thr Leu Ile
            690                 695                 700

Glu Tyr Glu Val Pro Gln Leu Leu Ser Ser Val Ala Glu Ser Ser
705             710                 715                 720

Asn Thr Ser Ser Arg Leu Ser Val Ile Val Arg Lys Lys Cys Met
                725                 730                 735

Pro Arg Phe Phe Thr Glu Met Asn Arg Thr Val Gln Asn Pro Pro Leu
                740                 745                 750

Gly Thr Val Val Asp Ser Glu Ala Thr Arg Asn Glu Trp Tyr Asp Phe
                755                 760                 765

Tyr Leu Ile Ser Gln Val Ala Cys Arg Gly Thr Val Ser Pro Thr Tyr
770                 775                 780

Tyr Asn Val Ile Tyr Asp Asp Asn Gly Leu Lys Pro Asp His Met Gln
785                 790                 795                 800

Arg Leu Thr Phe Lys Leu Cys His Leu Tyr Tyr Asn Trp Pro Gly Ile
                805                 810                 815

Val Ser Val Pro Ala Pro Cys Gln Tyr Ala His Lys Leu Thr Phe Leu
                820                 825                 830

Val Ala Gln Ser Ile His Lys Glu Pro Ser Leu Glu Leu Ala Asn His
            835                 840                 845

Leu Phe Tyr Leu
    850

<210> SEQ ID NO 2
<211> LENGTH: 3214
<212> TYPE: DNA
<213> ORGANISM: Homo sapiens

<400> SEQUENCE: 2
gtgctcgcgc caaccctac gccccagcgc gccttctcca cccacgcacg ggcctcggac    60
gcatttccag ccccggcgtt ggttgtggat gctggacatc accgcctcc aggcagtttc   120 gccgtcacac cgtcgccatc tgtagccaaa gcaaaacata tcctaactga gactttgcag   180
ctcttgtggc cactctgggc tcaccgggaa catgagtgga agagcccgag tgaaggccag   240
aggcatcgcc cgcagcccca gtgccacaga gtggggcgc atccaagcct cgccattgcc   300
tagatctgtt gatcttagta caatgaagc atcctctagc aatggcttct tgggaacaag   360
caggatctca accaacgata aatatgggat atcttctggt gatgctggaa gtaccttcat   420
ggaaagaggt gtgaaaaaca aacaggactt tatggatttg agtatctgta ccagagaaaa   480
attggcacat gtgagaaatt gtaaaacagg ttccagtgga atacctgtga actggttac   540 aaacctcttt aacttagatt ttccccaaga ctggcagcta taccagtacc atgtgacata   600
tattccagat ttagcatcta gaaggctgag aattgcttta ctttatagtc atagtgaact   660

```
ttccaacaaa gcaaaagcat tcgacggtgc catccttttt ctgtcacaaa agctagaaga      720
aaaggtcaca gagttgtcaa gtgaaactca aagaggtgag actataaaga tgactatcac      780
cctgaagagg gagctgccat caagttctcc cgtgtgcatc caggtcttca atatcatctt      840
cagaaagatc ctcaaaaagt tgtccatgta ccaaattgga cggaacttct ataatccttc      900
agagccaatg gaaattcccc agcacaaatt atccctttgg cctgggtttg ccatttctgt      960
gtcatatttt gaaaggaagc tcctgtttag tgctgatgtg agttacaaag tcctccggaa     1020
tgagacggtt ctggaattca tgactgctct ctgtcaaaga actggcttgt cctgtttcac     1080
ccagacgtgt gagaagcagc taatagggct cattgtcctt acaagataca ataacagaac     1140
ctactccatt gatgacattg actggtcagt gaagcccaca cacacctttc agaagcggga     1200
tggcaccgag atcacctatg tggattacta caagcagcag tatgatatta ctgtatcgga     1260
cctgaatcag cccatgcttg ttagtctgtt aaagaagaag agaaatgaca acagtgaggc     1320
tcagctcgcc cacctgatac ctgagctctg ctttctaaca gggctgactg accaggcaac     1380
atctgatttc cagctgatga aggctgtggc tgaaaagaca cgtctcagtc cttcaggccg     1440
gcagcagcgc ctggccaggc ttgtggacaa catccagagg aataccaatg ctcgctttga     1500
actagagacc tggggactgc attttggaag ccagatatct ctgactggcc ggattgtgcc     1560
ttcagaaaaa atattaatgc aagaccacat atgtcaacct gtgtctgctg ctgactggtc     1620
caaggatatt cgaacttgca agattttaaa tgcacagtct ttgaatacct ggttgatttt     1680
atgtagcgac agaactgaat atgttgccga gagctttctg aactgcttga agagagttgc     1740
aggttccatg ggatttaatg tggactaccc caaaatcata aaagtacaag aaaatccagc     1800
tgcatttgtt agagctatac agcaatatgt tgatcctgat gttcagctgg taatgtgcat     1860
tctgccttct aatcagaaga cctattatga ttccattaaa aaatatttga gctcagactg     1920
cccagtccca agccaatgtg tgcttgctcg gaccttgaat aaacagggca tgatgatgag     1980
tatcgccacc aagatcgcta tgcagatgac ttgcaagctc ggaggcgagc tgtgggctgt     2040
ggaaatacct ttaaagtccc tgatggtggt cggtattgat gtctgtaaag atgcactcag     2100
caaggacgtg atggttgttg gatgcgtggc cagtgttaac cccagaatca ccaggtggtt     2160
ttcccgctgt atccttcaga gaacaatgac tgatgttgca gattgcttga agttttcat      2220 gactggagca ctcaacaaat ggtacaagta caatcatgat ttgccagcac ggataattgt     2280
gtaccgtgct ggtgtagggg atggtcagct gaaaacactt attgaatatg aagtcccaca     2340
gctgctgagc agtgtggcag aatccagctc aaataccagc tcaagactgt cggtgattgt     2400
ggtcaggaag aagtgcatgc cacgattctt taccgaaatg aaccgcactg tacagaaccc     2460
cccacttggc actgttgtgg attcagaagc aacacgtaac gaatggtatg acttttatct     2520
gatcagccag gtggcctgcc ggggaactgt tagtcctacc tactataatg tcatctatga     2580
tgacaacggc ttgaagcccg accatatgca gagacttaca ttcaaattgt gccacctgta     2640
ctacaactgg ccgggcatag tcagtgtccc agcaccatgt cagtatgctc acaagctgac     2700
ctttctggtg gcacaaagca ttcataaaga acccagtctg gaattagcca accatctctt     2760
ctacctgtga tggcatgaac tactggcatc actagatgga caatccaaga agaaattggt     2820
atactttgtg caaatctgcc ataagctcaa ggctgtgact ggggaaaaag attgagctta     2880
gttttcatgt ctaggaaaaa aagcaaaaca acttaatctg aaacagtttt aaaaaatgtg     2940 tgttatttttg ttttaaagag ttgtatgctt ggggtaaatt tcattgtca tatgtggaat      3000 ttaaatatac catcatctac aaagaattcc acagagttaa atatcttaag ttaaacactt     3060
```

```
aaaataagtg tttgcgtgat attttgatga cagataaaca gagtctaatt cccaccccaa    3120
attttgctga ggttttctta atgttgtaga gcattttgta gagtggttta aatagttgaa    3180
aataaagttc agaacatcaa aaaaaaaaaa aaaa                                 3214
```

<210> SEQ ID NO 3
<211> LENGTH: 27
<212> TYPE: DNA
<213> ORGANISM: Artificial Sequence
<220> FEATURE:
<223> OTHER INFORMATION: small RNA

<400> SEQUENCE: 3

```
ggccgtgatc gtatagtggt tagtact                                         27
```

<210> SEQ ID NO 4
<211> LENGTH: 27
<212> TYPE: DNA
<213> ORGANISM: Artificial Sequence
<220> FEATURE:
<223> OTHER INFORMATION: small RNA

<400> SEQUENCE: 4

```
gattatgatg atgccttaac actgact                                         27
```

<210> SEQ ID NO 5
<211> LENGTH: 26
<212> TYPE: DNA
<213> ORGANISM: Artificial Sequence
<220> FEATURE:
<223> OTHER INFORMATION: small RNA

<400> SEQUENCE: 5

```
agccctgatg atgcccactc ctgagc                                          26
```

<210> SEQ ID NO 6
<211> LENGTH: 26
<212> TYPE: DNA
<213> ORGANISM: Artificial Sequence
<220> FEATURE:
<223> OTHER INFORMATION: small RNA

<400> SEQUENCE: 6

```
ccccccactg ctaaatttga ctggct                                          26
```

<210> SEQ ID NO 7
<211> LENGTH: 24
<212> TYPE: DNA
<213> ORGANISM: Artificial Sequence
<220> FEATURE:
<223> OTHER INFORMATION: small RNA

<400> SEQUENCE: 7

```
ccccccactg ctaaatttga ctgg                                            24
```

<210> SEQ ID NO 8
<211> LENGTH: 27
<212> TYPE: DNA
<213> ORGANISM: Artificial Sequence
<220> FEATURE:
<223> OTHER INFORMATION: small RNA

<400> SEQUENCE: 8

```
ccccccactg ctaaatttga ctggcta                                         27
```

```
<210> SEQ ID NO 9
<211> LENGTH: 25
<212> TYPE: DNA
<213> ORGANISM: Artificial Sequence
<220> FEATURE:
<223> OTHER INFORMATION: small RNA

<400> SEQUENCE: 9 cccccactg ctaaatttga ctggc                                          25

<210> SEQ ID NO 10
<211> LENGTH: 25
<212> TYPE: DNA
<213> ORGANISM: Artificial Sequence
<220> FEATURE:
<223> OTHER INFORMATION: small RNA

<400> SEQUENCE: 10
ccccccactg ctaaatttga ctggt                                         25

<210> SEQ ID NO 11
<211> LENGTH: 24
<212> TYPE: DNA
<213> ORGANISM: Artificial Sequence
<220> FEATURE:
<223> OTHER INFORMATION: artificial sequence

<400> SEQUENCE: 11 ccccactgc taaatttgac tggc                                           24

<210> SEQ ID NO 12
<211> LENGTH: 25
<212> TYPE: DNA
<213> ORGANISM: Artificial Sequence
<220> FEATURE:
<223> OTHER INFORMATION: small RNA

<400> SEQUENCE: 12 ccccactgc taaatttgac tggct                                          25

<210> SEQ ID NO 13
<211> LENGTH: 29
<212> TYPE: DNA
<213> ORGANISM: Artificial Sequence
<220> FEATURE:
<223> OTHER INFORMATION: small RNA

<400> SEQUENCE: 13
ctgagcaaca tagcgagacc ccgtctcta                                     29

<210> SEQ ID NO 14
<211> LENGTH: 26
<212> TYPE: DNA
<213> ORGANISM: Artificial Sequence
<220> FEATURE:
<223> OTHER INFORMATION: small RNA

<400> SEQUENCE: 14 ccccactgc taaatttgac tggcta                                         26

<210> SEQ ID NO 15
<211> LENGTH: 24
<212> TYPE: DNA
<213> ORGANISM: Artificial Sequence
<220> FEATURE:
<223> OTHER INFORMATION: small RNA
```

<400> SEQUENCE: 15
cccccactgc taaatttgac tggt                                              24

<210> SEQ ID NO 16
<211> LENGTH: 31
<212> TYPE: DNA
<213> ORGANISM: Artificial Sequence
<220> FEATURE:
<223> OTHER INFORMATION: small RNA

<400> SEQUENCE: 16
gcctgagcaa catagcgaga ccccgtctct a                                      31

<210> SEQ ID NO 17
<211> LENGTH: 28
<212> TYPE: DNA
<213> ORGANISM: Artificial Sequence
<220> FEATURE:
<223> OTHER INFORMATION: small RNA

<400> SEQUENCE: 17
ggccgtgatc gtatagtggt tagtactc                                          28

<210> SEQ ID NO 18
<211> LENGTH: 28
<212> TYPE: DNA
<213> ORGANISM: Artificial Sequence
<220> FEATURE:
<223> OTHER INFORMATION: small RNA

<400> SEQUENCE: 18
atgcagtgtg gaacacaatg aactgaac                                          28

<210> SEQ ID NO 19
<211> LENGTH: 26
<212> TYPE: DNA
<213> ORGANISM: Artificial Sequence
<220> FEATURE:
<223> OTHER INFORMATION: small RNA

<400> SEQUENCE: 19
ggccgtgatc gtatagtggt tagtac                                            26

<210> SEQ ID NO 20
<211> LENGTH: 30
<212> TYPE: DNA
<213> ORGANISM: Artificial Sequence
<220> FEATURE:
<223> OTHER INFORMATION: small RNA

<400> SEQUENCE: 20
ggccgtgatc gtatagtggt tagtactctg                                        30

<210> SEQ ID NO 21
<211> LENGTH: 26
<212> TYPE: DNA
<213> ORGANISM: Artificial Sequence
<220> FEATURE:
<223> OTHER INFORMATION: small RNA

<400> SEQUENCE: 21 cccccactg ctaaatttga ctggtt                                             26

<210> SEQ ID NO 22

<210> SEQ ID NO 22
<211> LENGTH: 24
<212> TYPE: DNA
<213> ORGANISM: Artificial Sequence
<220> FEATURE:
<223> OTHER INFORMATION: small RNA

<400> SEQUENCE: 22
ccccactgct aaatttgact ggct                                          24

<210> SEQ ID NO 23
<211> LENGTH: 32
<212> TYPE: DNA
<213> ORGANISM: Artificial Sequence
<220> FEATURE:
<223> OTHER INFORMATION: small RNA

<400> SEQUENCE: 23
agcctgagca acatagcgag accccgtctc ta                                 32

<210> SEQ ID NO 24
<211> LENGTH: 30
<212> TYPE: DNA
<213> ORGANISM: Artificial Sequence
<220> FEATURE:
<223> OTHER INFORMATION: small RNA

<400> SEQUENCE: 24
gcctgagcaa catagcgaga ccccgtctct                                    30

<210> SEQ ID NO 25
<211> LENGTH: 29
<212> TYPE: DNA
<213> ORGANISM: Artificial Sequence
<220> FEATURE:
<223> OTHER INFORMATION: small RNA

<400> SEQUENCE: 25
cctgagcaac atagcgagac cccgtctct                                     29

<210> SEQ ID NO 26
<211> LENGTH: 27
<212> TYPE: DNA
<213> ORGANISM: Artificial Sequence
<220> FEATURE:
<223> OTHER INFORMATION: small RNA

<400> SEQUENCE: 26
ttcactgatg agagcattgt tctgagc                                       27

<210> SEQ ID NO 27
<211> LENGTH: 28
<212> TYPE: DNA
<213> ORGANISM: Artificial Sequence
<220> FEATURE:
<223> OTHER INFORMATION: small RNA

<400> SEQUENCE: 27
gttcactgat gagagcattg ttctgagc                                      28

<210> SEQ ID NO 28
<211> LENGTH: 25
<212> TYPE: DNA
<213> ORGANISM: Artificial Sequence
<220> FEATURE:
<223> OTHER INFORMATION: small RNA

<400> SEQUENCE: 28
cccccactgc taaatttgac tggtt                                              25

<210> SEQ ID NO 29
<211> LENGTH: 26
<212> TYPE: DNA
<213> ORGANISM: Artificial Sequence
<220> FEATURE:
<223> OTHER INFORMATION: small RNA

<400> SEQUENCE: 29
cccacccagg gacgcgtggt gacttt                                             26

<210> SEQ ID NO 30
<211> LENGTH: 27
<212> TYPE: DNA
<213> ORGANISM: Artificial Sequence
<220> FEATURE:
<223> OTHER INFORMATION: small RNA

<400> SEQUENCE: 30
atgcagtgtg gaacacaatg aactgaa                                            27

<210> SEQ ID NO 31
<211> LENGTH: 27
<212> TYPE: DNA
<213> ORGANISM: Artificial Sequence
<220> FEATURE:
<223> OTHER INFORMATION: small RNA

<400> SEQUENCE: 31
tgcagtgtgg aacacaatga actgaac                                            27

<210> SEQ ID NO 32
<211> LENGTH: 25
<212> TYPE: DNA
<213> ORGANISM: Artificial Sequence
<220> FEATURE:
<223> OTHER INFORMATION: small RNA

<400> SEQUENCE: 32
cactgatgag agcattgttc tgagc                                              25

<210> SEQ ID NO 33
<211> LENGTH: 31
<212> TYPE: DNA
<213> ORGANISM: Artificial Sequence
<220> FEATURE:
<223> OTHER INFORMATION: small RNA

<400> SEQUENCE: 33
agcctgagca acatagcgag accccgtctc t                                       31

<210> SEQ ID NO 34
<211> LENGTH: 29
<212> TYPE: DNA
<213> ORGANISM: Artificial Sequence
<220> FEATURE:
<223> OTHER INFORMATION: small RNA

<400> SEQUENCE: 34
ttgcaagcaa cactctgtgg cagatgatc                                          29

<210> SEQ ID NO 35
<211> LENGTH: 26
<212> TYPE: DNA

```
<213> ORGANISM: Artificial Sequence
<220> FEATURE:
<223> OTHER INFORMATION: small RNA

<400> SEQUENCE: 35
gtagtgcgct atgccgatcg ggtgtc                                          26

<210> SEQ ID NO 36
<211> LENGTH: 30
<212> TYPE: DNA
<213> ORGANISM: Artificial Sequence
<220> FEATURE:
<223> OTHER INFORMATION: small RNA

<400> SEQUENCE: 36
gttcactgat gagagcattg ttctgagcca                                      30

<210> SEQ ID NO 37
<211> LENGTH: 27
<212> TYPE: DNA
<213> ORGANISM: Artificial Sequence
<220> FEATURE:
<223> OTHER INFORMATION: TTAAGGGGAACGTGTGGGCTATTTAGG

<400> SEQUENCE: 37
ttaaggggaa cgtgtgggct atttagg                                         27

<210> SEQ ID NO 38
<211> LENGTH: 27
<212> TYPE: DNA
<213> ORGANISM: Artificial Sequence
<220> FEATURE:
<223> OTHER INFORMATION: small RNA

<400> SEQUENCE: 38
ttgcaagcaa cactctgtgg cagatga                                         27

<210> SEQ ID NO 39
<211> LENGTH: 26
<212> TYPE: DNA
<213> ORGANISM: Artificial Sequence
<220> FEATURE:
<223> OTHER INFORMATION: small RNA

<400> SEQUENCE: 39
tggaaaggat gaagagctga ctgatg                                          26

<210> SEQ ID NO 40
<211> LENGTH: 27
<212> TYPE: DNA
<213> ORGANISM: Artificial Sequence
<220> FEATURE:
<223> OTHER INFORMATION: small RNA

<400> SEQUENCE: 40 cccccttttaa aaagcactca atgggcc                                        27

<210> SEQ ID NO 41
<211> LENGTH: 27
<212> TYPE: DNA
<213> ORGANISM: Artificial Sequence
<220> FEATURE:
<223> OTHER INFORMATION: small RNA

<400> SEQUENCE: 41
ggtgctgatg acacccactg gctgaac                                         27
```

<210> SEQ ID NO 42
<211> LENGTH: 28
<212> TYPE: DNA
<213> ORGANISM: Artificial Sequence
<220> FEATURE:
<223> OTHER INFORMATION: small RNA

<400> SEQUENCE: 42
gatcagtagt gggatcgcgc ctgtgaat                                    28

<210> SEQ ID NO 43
<211> LENGTH: 26
<212> TYPE: DNA
<213> ORGANISM: Artificial Sequence
<220> FEATURE:
<223> OTHER INFORMATION: small RNA

<400> SEQUENCE: 43
tgatcagtag tgggatcgcg cctgtg                                      26

<210> SEQ ID NO 44
<211> LENGTH: 26
<212> TYPE: DNA
<213> ORGANISM: Artificial Sequence
<220> FEATURE:
<223> OTHER INFORMATION: small RNA

<400> SEQUENCE: 44
tgtagtgcgc tatgccgatc gggtgt                                      26

<210> SEQ ID NO 45
<211> LENGTH: 27
<212> TYPE: DNA
<213> ORGANISM: Artificial Sequence
<220> FEATURE:
<223> OTHER INFORMATION: small RNA

<400> SEQUENCE: 45
gtagtgcgct atgccgatcg ggtgtcc                                     27

<210> SEQ ID NO 46
<211> LENGTH: 25
<212> TYPE: DNA
<213> ORGANISM: Artificial Sequence
<220> FEATURE:
<223> OTHER INFORMATION: small RNA

<400> SEQUENCE: 46
gtagtgcgct atgccgatcg ggtgt                                       25

<210> SEQ ID NO 47
<211> LENGTH: 28
<212> TYPE: DNA
<213> ORGANISM: Artificial Sequence
<220> FEATURE:
<223> OTHER INFORMATION: small RNA

<400> SEQUENCE: 47
ttgcaagcaa cactctgtgg cagatgat                                    28

<210> SEQ ID NO 48
<211> LENGTH: 25
<212> TYPE: DNA
<213> ORGANISM: Artificial Sequence
<220> FEATURE:

<223> OTHER INFORMATION: small RNA

<400> SEQUENCE: 48
agtgcgctat gccgatcggg tgtcc                                          25

<210> SEQ ID NO 49
<211> LENGTH: 26
<212> TYPE: DNA
<213> ORGANISM: Artificial Sequence
<220> FEATURE:
<223> OTHER INFORMATION: small RNA

<400> SEQUENCE: 49
tcagtagtgg gatcgcgcct gtgaat                                         26

<210> SEQ ID NO 50
<211> LENGTH: 26
<212> TYPE: DNA
<213> ORGANISM: Artificial Sequence
<220> FEATURE:
<223> OTHER INFORMATION: small RNA

<400> SEQUENCE: 50
tcataccata tgcgtgtctc caaagt                                         26

<210> SEQ ID NO 51
<211> LENGTH: 31
<212> TYPE: DNA
<213> ORGANISM: Artificial Sequence
<220> FEATURE:
<223> OTHER INFORMATION: small RNA

<400> SEQUENCE: 51
tcgccgtgat cgtatagtgg ttagtactct g                                   31

<210> SEQ ID NO 52
<211> LENGTH: 26
<212> TYPE: DNA
<213> ORGANISM: Artificial Sequence
<220> FEATURE:
<223> OTHER INFORMATION: small RNA

<400> SEQUENCE: 52
tgtaaaagac gtgaaccagc aggagt                                         26

<210> SEQ ID NO 53
<211> LENGTH: 27
<212> TYPE: DNA
<213> ORGANISM: Artificial Sequence
<220> FEATURE:
<223> OTHER INFORMATION: small RNA

<400> SEQUENCE: 53
tggaaaggat gaagagctga ctgatgg                                        27

<210> SEQ ID NO 54
<211> LENGTH: 26
<212> TYPE: DNA
<213> ORGANISM: Artificial Sequence
<220> FEATURE:
<223> OTHER INFORMATION: small RNA

<400> SEQUENCE: 54
gcagtgtgga acacaatgaa ctgaac                                         26

<210> SEQ ID NO 55
<211> LENGTH: 29
<212> TYPE: DNA
<213> ORGANISM: Artificial Sequence
<220> FEATURE:
<223> OTHER INFORMATION: small RNA

<400> SEQUENCE: 55
tgatcagtag tgggatcgcg cctgtgaat                                    29

<210> SEQ ID NO 56
<211> LENGTH: 31
<212> TYPE: DNA
<213> ORGANISM: Artificial Sequence
<220> FEATURE:
<223> OTHER INFORMATION: small RNA

<400> SEQUENCE: 56
agcattggtg gttcagtggt agaattctcg c                                 31

<210> SEQ ID NO 57
<211> LENGTH: 25
<212> TYPE: DNA
<213> ORGANISM: Artificial Sequence
<220> FEATURE:
<223> OTHER INFORMATION: small RNA

<400> SEQUENCE: 57
cagtgtggaa cacaatgaac tgaac                                        25

<210> SEQ ID NO 58
<211> LENGTH: 29
<212> TYPE: DNA
<213> ORGANISM: Artificial Sequence
<220> FEATURE:
<223> OTHER INFORMATION: small RNA

<400> SEQUENCE: 58
ctgcaatgat gaaaatgtag ctactgagc                                    29

<210> SEQ ID NO 59
<211> LENGTH: 31
<212> TYPE: DNA
<213> ORGANISM: Artificial Sequence
<220> FEATURE:
<223> OTHER INFORMATION: small RNA

<400> SEQUENCE: 59
gagcatggta atggatttat ggtgggtcct t                                 31

<210> SEQ ID NO 60
<211> LENGTH: 26
<212> TYPE: DNA
<213> ORGANISM: Artificial Sequence
<220> FEATURE:
<223> OTHER INFORMATION: small RNA

<400> SEQUENCE: 60
ggaaaggatg aagagctgac tgatgg                                       26

<210> SEQ ID NO 61
<211> LENGTH: 28
<212> TYPE: DNA
<213> ORGANISM: Artificial Sequence
<220> FEATURE:
<223> OTHER INFORMATION: small RNA

```
<400> SEQUENCE: 61
tgcgcgacat caaggagaag ctgtgcta                                        28

<210> SEQ ID NO 62
<211> LENGTH: 28
<212> TYPE: DNA
<213> ORGANISM: Artificial Sequence
<220> FEATURE:
<223> OTHER INFORMATION: small RNA

<400> SEQUENCE: 62
tgtagtgcgc tatgccgatc gggtgtcc                                        28

<210> SEQ ID NO 63
<211> LENGTH: 28
<212> TYPE: DNA
<213> ORGANISM: Artificial Sequence
<220> FEATURE:
<223> OTHER INFORMATION: small RNA

<400> SEQUENCE: 63
ttggaggatg aaacaaagga atctgact                                        28

<210> SEQ ID NO 64
<211> LENGTH: 22
<212> TYPE: DNA
<213> ORGANISM: Artificial Sequence
<220> FEATURE:
<223> OTHER INFORMATION: PIWIL1 Forward

<400> SEQUENCE: 64
acgctgcata tttcaggata ga                                              22

<210> SEQ ID NO 65
<211> LENGTH: 22
<212> TYPE: DNA
<213> ORGANISM: Artificial Sequence
<220> FEATURE:
<223> OTHER INFORMATION: PIWIL1 Reverse

<400> SEQUENCE: 65
gacagtgaca gatttggctc tc                                              22

<210> SEQ ID NO 66
<211> LENGTH: 20
<212> TYPE: DNA
<213> ORGANISM: Artificial Sequence
<220> FEATURE:
<223> OTHER INFORMATION: PIWIL2 Forward

<400> SEQUENCE: 66
ttgtggacag cctgaagcta                                                 20

<210> SEQ ID NO 67
<211> LENGTH: 20
<212> TYPE: DNA
<213> ORGANISM: Artificial Sequence
<220> FEATURE:
<223> OTHER INFORMATION: PIWIL2 Reverse

<400> SEQUENCE: 67
ccatcagaca ctccatcacg                                                 20

<210> SEQ ID NO 68
<211> LENGTH: 23
```

```
<212> TYPE: DNA
<213> ORGANISM: Artificial Sequence
<220> FEATURE:
<223> OTHER INFORMATION: PIWIL4 forward

<400> SEQUENCE: 68
aatgctcgct ttgaactaga gac                                      23

<210> SEQ ID NO 69
<211> LENGTH: 25
<212> TYPE: DNA
<213> ORGANISM: Artificial Sequence
<220> FEATURE:
<223> OTHER INFORMATION: PIWIL4 reverse

<400> SEQUENCE: 69
attttggggt agtccacatt aaatc                                    25

<210> SEQ ID NO 70
<211> LENGTH: 24
<212> TYPE: DNA
<213> ORGANISM: Artificial Sequence
<220> FEATURE:
<223> OTHER INFORMATION: GAPDH forward

<400> SEQUENCE: 70
ggctgagaac gggaagcttg tcat                                     24

<210> SEQ ID NO 71
<211> LENGTH: 24
<212> TYPE: DNA
<213> ORGANISM: Artificial Sequence
<220> FEATURE:
<223> OTHER INFORMATION: GAPDH Reverse

<400> SEQUENCE: 71
cagccttctc catggtggtg aaga                                     24

<210> SEQ ID NO 72
<211> LENGTH: 19
<212> TYPE: DNA
<213> ORGANISM: Artificial Sequence
<220> FEATURE:
<223> OTHER INFORMATION: TGFBR1 Forward

<400> SEQUENCE: 72
tcgtctgcat ctcactcat                                           19

<210> SEQ ID NO 73
<211> LENGTH: 19
<212> TYPE: DNA
<213> ORGANISM: Artificial Sequence
<220> FEATURE:
<223> OTHER INFORMATION: TGFBR1 Reverse

<400> SEQUENCE: 73
gataaatctc tgcctcacg                                           19

<210> SEQ ID NO 74
<211> LENGTH: 19
<212> TYPE: DNA
<213> ORGANISM: Artificial Sequence
<220> FEATURE:
<223> OTHER INFORMATION: TGFBR2 Forward

<400> SEQUENCE: 74
```
gcgggagcac ccctgtgtc                                              19

<210> SEQ ID NO 75
<211> LENGTH: 21
<212> TYPE: DNA
<213> ORGANISM: Artificial Sequence
<220> FEATURE:
<223> OTHER INFORMATION: TGFBR2 Reverse

<400> SEQUENCE: 75
cccgagagcc tgtccagatg c                                           21

<210> SEQ ID NO 76
<211> LENGTH: 20
<212> TYPE: DNA
<213> ORGANISM: Artificial Sequence
<220> FEATURE:
<223> OTHER INFORMATION: TGFB1 Forward

<400> SEQUENCE: 76
accaactatt gcttcagctc                                             20

<210> SEQ ID NO 77
<211> LENGTH: 18
<212> TYPE: DNA
<213> ORGANISM: Artificial Sequence
<220> FEATURE:
<223> OTHER INFORMATION: TGFB1 Reverse

<400> SEQUENCE: 77
ttatgctggt tgtacagg                                               18

<210> SEQ ID NO 78
<211> LENGTH: 20
<212> TYPE: DNA
<213> ORGANISM: Artificial Sequence
<220> FEATURE:
<223> OTHER INFORMATION: TGFB3 Forward

<400> SEQUENCE: 78
cctttcagcc caatggagat                                             20

<210> SEQ ID NO 79
<211> LENGTH: 20
<212> TYPE: DNA
<213> ORGANISM: Artificial Sequence
<220> FEATURE:
<223> OTHER INFORMATION: TGFB3 Reverse

<400> SEQUENCE: 79
acacagcagt tctcctccaa                                             20

<210> SEQ ID NO 80
<211> LENGTH: 22
<212> TYPE: DNA
<213> ORGANISM: Artificial Sequence
<220> FEATURE:
<223> OTHER INFORMATION: FGFR2 Forward

<400> SEQUENCE: 80
cgctggtgag gataacaaca cg                                          22

<210> SEQ ID NO 81
<211> LENGTH: 23
<212> TYPE: DNA
<213> ORGANISM: Artificial Sequence
<220> FEATURE:
<223> OTHER INFORMATION: FGFR2 Reverse

<400> SEQUENCE: 81
tggaagttca tactcggaga ccc                                    23

<210> SEQ ID NO 82
<211> LENGTH: 60
<212> TYPE: DNA
<213> ORGANISM: Artificial Sequence
<220> FEATURE:
<223> OTHER INFORMATION: sh-PIWIL4-1 Forward

<400> SEQUENCE: 82
gatcccccca gtaccatgtg acatatttca agagaatatg tcacatggta ctggttttta    60

<210> SEQ ID NO 83
<211> LENGTH: 60
<212> TYPE: DNA
<213> ORGANISM: Artificial Sequence
<220> FEATURE:
<223> OTHER INFORMATION: sh-PIWIL4-1 Reverse

<400> SEQUENCE: 83
agcttaaaaa ccagtaccat gtgacatatt ctcttgaaat atgtcacatg gtactggggg    60

<210> SEQ ID NO 84
<211> LENGTH: 60
<212> TYPE: DNA
<213> ORGANISM: Artificial Sequence
<220> FEATURE:
<223> OTHER INFORMATION: sh-PIWIL4-2

<400> SEQUENCE: 84
gatccccctg tatcggacct gaatcattca agagatgatt caggtccgat acagttttta    60

<210> SEQ ID NO 85
<211> LENGTH: 60
<212> TYPE: DNA
<213> ORGANISM: Artificial Sequence
<220> FEATURE:
<223> OTHER INFORMATION: sh-PIWIL4-2

<400> SEQUENCE: 85
agcttaaaaa ctgtatcgga cctgaatcat ctcttgaatg attcaggtcc gatacagggg    60

<210> SEQ ID NO 86
<211> LENGTH: 60
<212> TYPE: DNA
<213> ORGANISM: Artificial Sequence
<220> FEATURE:
<223> OTHER INFORMATION: sh-PIWIL4-3 Forward

<400> SEQUENCE: 86
gatcccccac gtaacgaatg gtatgattca agagatcata ccattcgtta cgtgttttta    60

<210> SEQ ID NO 87
<211> LENGTH: 60
<212> TYPE: DNA
<213> ORGANISM: Artificial Sequence
<220> FEATURE:
<223> OTHER INFORMATION: sh-PIWIL4-3

<400> SEQUENCE: 87
agcttaaaaa cacgtaacga atggtatgat ctcttgaatc ataccattcg ttacgtgggg    60

```
<210> SEQ ID NO 88
<211> LENGTH: 26
<212> TYPE: DNA
<213> ORGANISM: Artificial Sequence
<220> FEATURE:
<223> OTHER INFORMATION: PIWL4 cDNA Forward

<400> SEQUENCE: 88
cgcggatcca tgagtggaag agcccg                                          26

<210> SEQ ID NO 89
<211> LENGTH: 28
<212> TYPE: DNA
<213> ORGANISM: Artificial Sequence
<220> FEATURE:
<223> OTHER INFORMATION: PIWL4 cDNA Reverse

<400> SEQUENCE: 89
cgcggatcct cacaggtaga agagatgg                                        28
```

COMPOSITIONS AND METHODS FOR TREATING CANCER BY INHIBITING PIWIL4

CROSS REFERENCE TO RELATED APPLICATIONS

This application is a national stage entry, filed under 35 U.S.C. § 371, of International Application No. PCT/CN2016/109858, filed on Dec. 14, 2016, the content of which is hereby incorporated by reference in its entirety.

FIELD OF THE INVENTION

The present invention relates to compositions and methods for treating cancer by inhibiting PIWIL4.

BACKGROUND OF THE INVENTION

PIWI proteins represent a subfamily of the Argonaute (Ago) protein family and are highly conserved among eukaryotes and archaea. PIWI proteins bind to a class of non-coding small RNAs called PIWI-interacting RNAs (piRNAs) (Aravin, A., et al. (2006) *Nature* 442, 203-207, Girard, A., et al (2006) *Nature* 442, 199-202, Grivna, S. T., et al (2006) *Genes Dev.* 20, 1709-1714, and Juliano, C et al (2011) *Annu. Rev. Genet.* 45, 447-469). The PIWI-piRNA complex regulates gene expression at epigenetic and post-transcriptional levels (Yan, H., et al (2015) *Leukemia* 29, 196-206, Watanabe, T., and Lin, H. (2014) *Mol. Cell* 56, 18-27, Sytnikova, Y. A., et al (2014) *Genome Res.* 24, 1977-1990, and Yin, H., and Lin, H. (2007) *Nature* 450, 304-308). PIWI proteins and piRNAs are mostly expressed in the germ line, where PIWI proteins have been demonstrated to be essential for germ line development, stem cell self-renewal, and gametogenesis in diverse organisms (Juliano, C et al (2011) *Annu. Rev. Genet.* 45, 447-469, Lin, H., and Spradling, A. C. (1997) *Development* 124, 2463-2476, Cox, et al (2000) *Development* 127, 503-514, Deng, W., and Lin, H. (2002) *Dev. Cell* 2, 819-830, Kuramochi-Miyagawa, S., et al (2004) *Development* 131, 839-849, Carmell, M. A., et al (2007) *Dev. Cell* 12, 503-514, and Gonzalez, J., et al (2015) *Cell Rep.* 12, 150-161). In addition, there is increasing evidence for somatic expression of PIWI proteins in *Drosophila* and mouse tissues (Gonzalez, J., et al (2015) *Cell Rep.* 12, 150-161, Cox, D. N., et al (1998) *Genes Dev.* 12, 3715-3727, and Lee, E. J., et al (2011) *RNA* 17, 1090-1099). Furthermore, it has been reported that PIWI proteins have aberrant and ectopic expression in a wide spectrum of cancers (Kwon, C., et al (2014) *Biochem. Biophys. Res. Commun.* 446, 218-223, Chen, C., et al (2013) *Cancer Biomark.* 13, 315-321, Suzuki, R., et al (2012) *Front. Genet.* 3, 204, Wang, Y. et al (2012) *Int. J. Clin. Exp. Pathol.* 5, 315-325, Siddiqi, S., and Matushansky, I. (2012) *J. Cell. Biochem.* 113, 373-380, Qiao, D., et al (2002) *Oncogene* 21, 3988-3999, and Ross, R. J. et al (2014) *Nature* 505, 353-359). For example, PIWI2 is highly expressed in breast cancer (Ye, Y., et al (2010) *PloS ONE* 5, e13406). Hence, PIWI might be involved in cancer formation and/or progression.

Breast cancer comprises four subtypes based on the expression of estrogen receptor, progesterone receptor, and human epidermal growth factor receptor (HER2). Triple-negative breast cancer (TNBC) lacks estrogen receptor, progesterone receptor, and HER2 expression (Linn, S. C., and Van't Veer, L. J. (2009) *Eur. J. Cancer* 45, 11-26, Rakha, E. A., and Ellis, I. O. (2009) *Pathology* 41, 40-47, and Rakha, E. A., et al (2009) *Clin. Cancer Res.* 15, 2302-2310), represents 10-25% of all breast cancers, and is a clinical therapy hot spot because of the vulnerability of younger women to this subtype of breast cancer (Liedtke, C., et al (2008) *J. Clin. Oncol.* 26, 1275-1281). Furthermore, TNBC patients do not benefit from targeted treatments such as endocrine therapy or trastuzumab because this subtype of cancer lacks the appropriate targets for these drugs. These challenges point to the pressing need to identify pathogenic pathways in TNBC. Recent studies have identified genetic alterations and gene expression profiles associated with subtypes of TNBC, including the implication of the PI3K/Akt/mTOR (mechanistic target of rapamycin) pathway in TNBC (Banerji, S. et al. (2012) *Nature* 486, 405-409, and Koboldt, D. C. et al. (2012) *Nature* 490, 61-70, Lehmann, B. D., et al (2011) *H. Clin. Invest.* 121, 2750-2767, and Shah, S. P., et al. (2009) *Nature* 461, 809-U867). However, therapeutic blockade of this pathway with the PI3K/Akt/mechanistic target of rapamycin inhibitor has not been effective, indicating the existence of other mechanisms that are determinative in inducing TNBC.

SUMMARY OF THE INVENTION

The present invention is based in part on the surprising discovery that PIWIL4 is widely expressed in breast cancer samples and several cell lines derived from TNBC. As described infra, reducing PIWIL4 expression significantly compromised cell migration, increased apoptosis, and reduced proliferation of the breast cancer cells. These effects may be achieved at least in part by activating TGF-β, MAPK/ERK, and FGF signaling. In addition, PIWIL4 repressed MHC class II expression, which helps cancer cells to avoid immune recognition and reaction. Therefore reducing PIWIL4 expression may also facilitate immune recognition and clearance of cancer cells.

In embodiments, the disclosure provides a method for treating a cancer in a subject in need thereof, the method comprising reducing PIWIL4 expression and/or activity in the cells of the cancer. In embodiments, the disclosure provides a method for treating a cancer in a subject in need thereof, the method comprising administering to the subject an anti-PIWIL4 agent in an amount effective to reduce the expression and/or activity of PIWIL4 in the cells of the cancer.

In embodiments, the anti-PIWIL4 agent is selected from the group consisting of an inhibitory nucleic acid, an antibody or fragment thereof, a peptide, a polypeptide or fragment thereof, and a small molecule. In embodiments, the anti-PIWIL4 agent is an inhibitory nucleic acid. In embodiments, the inhibitory nucleic acid is an RNAi molecule.

In embodiments, the subject is a human cancer patient. In embodiments, the cancer is a breast cancer. In embodiments, the breast cancer is an estrogen receptor-negative breast cancer, a progesterone receptor-negative breast cancer, or a human epidermal growth factor receptor 2 (HER2)-negative breast cancer. In embodiments, the breast cancer is negative for all three of estrogen receptor, progesterone receptor, and HER2, also referred to herein as "triple-negative breast cancer" or "TNBC". In embodiments, the breast cancer is triple-negative breast cancer.

In embodiments, the disclosure provides a method for diagnosing breast cancer, the method comprising detecting the expression or activity of PIWIL4 in a biological sample of the cancer. Overexpression of PIWIL4 in the breast tissue can be used as a diagnosis and prognosis of breast cancer. The diagnosis methods/criteria include DNA amplification, deletion, and missense mutation in the PIWIL4 locus as detected by DNA sequencing, restriction enzyme mapping, microarray analyses, or tissue in situ RNA hybridization; the overexpression of the PIWIL4 mRNA as detected by quantitative reverse PCR, Northern blot, dot blot, and RNA deep sequencing analyses; and the overexpression of the PIWIL4 protein as detected by western blot, ELISA, mass spectrometry, immnuo-precipitation, immune-staining, or immuno-fluorescence microscopy of the breast tissue. Normally PIWIL4 is not detectably expressed in breast cells by the above methods. Any detectable expression is indicative of the malignant state of the breast cells/tissue under-examination; and the strength of the PIWIL4 expression is positively correlated to the degree of malignancy and prognosis.

In embodiments, the disclosure provides a method of identifying an anti-PIWIL4 agent, the method comprising contacting a population of MDA-MB-231 cells with the agent and assaying the expression and/or activity of PIWIL4 in the cells, wherein a decrease in the expression and/or activity of PIWIL4 in the cells in the presence of the agent relative to the expression and/or activity of PIWIL4 in the cells in the absence of the agent indicates that the agent is an anti-PIWIL4 agent.

BRIEF DESCRIPTION OF THE DRAWINGS

FIG. 1A depicts a graph showing the relative expression of PIWIL1 in human breast cancer cell lines, MCF-10A, MDA-MB231, MDA-MB-435, MDA-MB-468, BT474, MCF-7, MDA-MB-453 and 4T1 cells.

FIG. 1B depicts a graph showing the relative expression of PIWIL2 in MCF-10A, MDA-MB231, MDA-MB-435, MDA-MB-468, BT474, MCF-7, MDA-MB-453 and 4T1 cells.

FIG. 1C depicts a graph showing the relative expression of PIWIL4 in MCF-10A, MDA-MB231, MDA-MB-435, MDA-MB-468, BT474, MCF-7, MDA-MB-453 and 4T1 cells. PIWIL4 was expressed at very high levels in five of six cancer cell lines, much higher than both PIWIL1 and PIWIL2.

FIG. 1D depicts a graph showing that PIWIL1 was expressed at significantly higher levels compared with the normal tissue controls in two of 20 breast cancer samples.

FIG. 1E depicts a graph showing that PIWIL2 was more highly four of 20 breast cancer samples.

FIG. 1F depicts a graph showing that PIWIL4 was significantly expressed in nine of 20 breast cancer samples, with five samples displaying a more than 50-fold upregulation.

FIG. 4G depicts images showing results of the in vitro wound healing assay (i.e. the scratch assay) conducted on MDA-MB-231 cells. Knocking down PIWIL4 with each of the three anti-PIWIL4 shRNAs significantly inhibited the migration ability of these cells by the scratch assay.

FIG. 4H depicts images showing the results of the transwell migration assay conducted on MDA-MB-231 cells. Knocking down PIWIL4 with each of the three anti-PIWIL4 shRNAs significantly inhibited the migration ability of these cells by the transwell assay.

FIG. 5B depicts a heatmap of the 60 most up- and down-regulated genes (38 up-regulated and 22 downregulated).

FIG. 5E depicts a graph showing the pathways enriched among proteins without shPIWIL4.

FIG. 6D depicts a graph showing that small RNA (remaining 24- to 32-nucleotide small RNAs) did not show the enrichment at either the 5' first position for U that was a signature of primary piRNA or at the 5' 10th position for A that was a signature of secondary piRNA.

DETAILED DESCRIPTION OF THE INVENTION

Figure 2A:
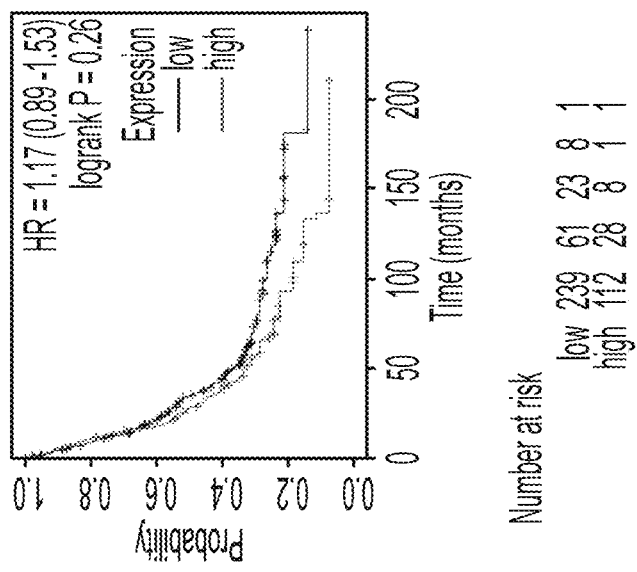
FIG. 2A depicts a graph showing a Kaplan-Meir survival analysis of PIWIL1 overall survival.
Figure 2B:
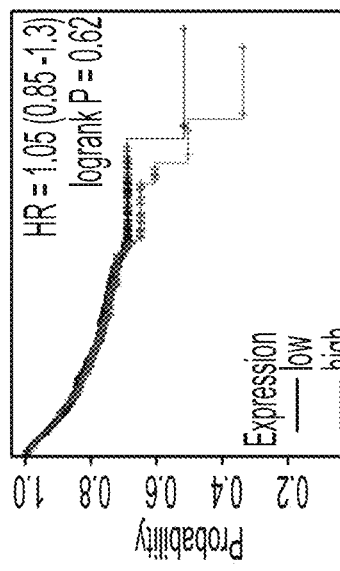
FIG. 2B depicts a graph showing a Kaplan-Meir survival analysis of PIWIL1 distance metastasis free survival.
Figure 2C:
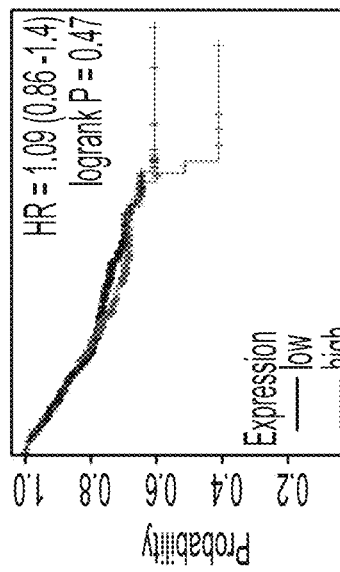
FIG. 2C depicts a graph showing a Kaplan-Meir survival analysis of PIWIL1 post progression survival.
Figure 2D:
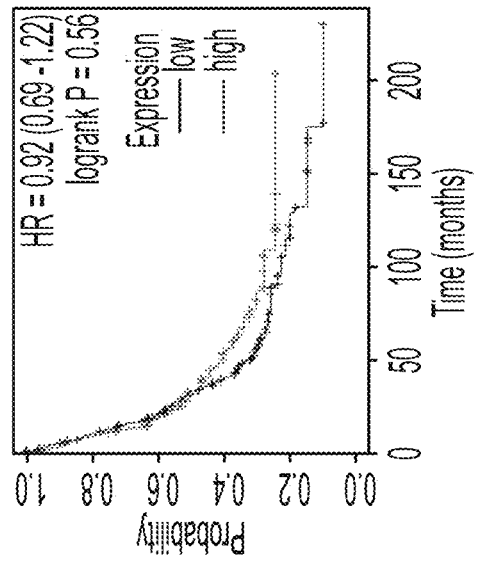
FIG. 2D depicts a graph showing a Kaplan-Meir survival analysis of PIWIL2 overall survival.
Figure 2E:
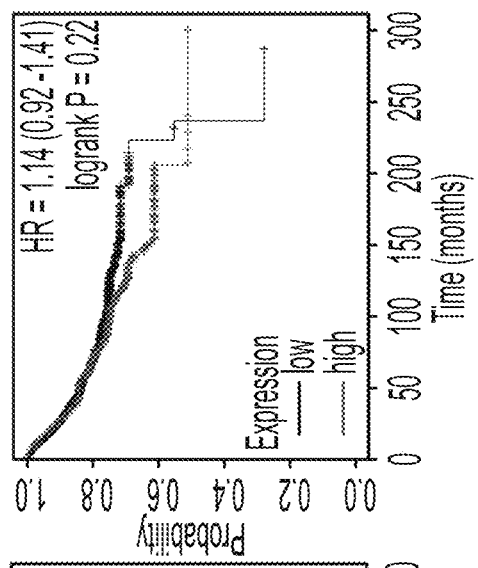
FIG. 2E depicts a graph showing a Kaplan-Meir survival analysis of PIWIL2 distance metastasis free survival.
Figure 2F:
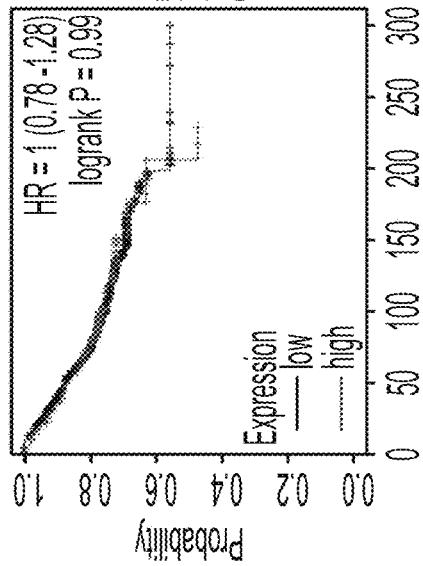
FIG. 2F depicts a graph showing a Kaplan-Meir survival analysis of PIWIL2 post progression survival.
Figure 2I:
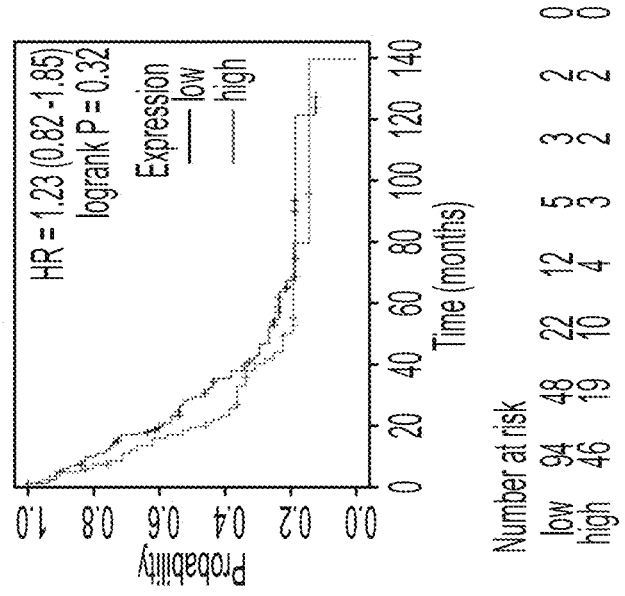
FIG. 2I depicts a graph showing a Kaplan-Meir survival analysis of PIWIL4 post progression survival.
Figure 2H:
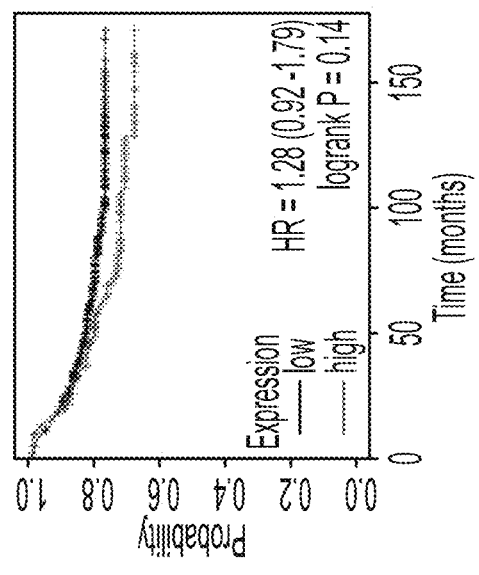
FIG. 2H depicts a graph showing a Kaplan-Meir survival analysis of PIWIL4 distance metastasis free survival.
Figure 2G:
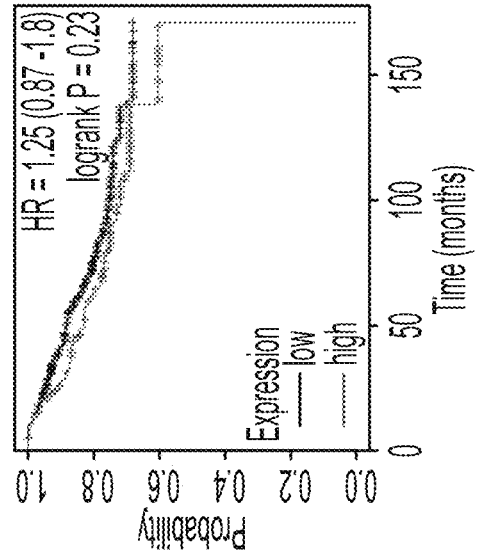
FIG. 2G depicts a graph showing a Kaplan-Meir survival analysis of PIWIL4 overall survival.

The disclosure provides compositions and methods for treating cancer in a subject, preferably a human subject, in need of such treatment. In embodiments, the methods for treating cancer comprise inhibiting the expression or activity of PIWIL4. The expression or activity of PIWIL4 is inhibited, for example, by contacting the cells of the cancer with an anti-PIWIL4 agent in an amount effective to decreases the amount of PIWIL4 expressed by the cancer cells and/or in an amount effective to reduce the intracellular signaling activity of PIWIL4. In embodiments, the anti-PIWIL4 agent is selected from the group consisting of an inhibitory nucleic acid, an antibody or binding fragment thereof, a peptide, a polypeptide or fragment thereof, and a small molecule.

The term "PIWIL4" refers to Piwi (P-element induced wimpy testis)-like protein 4. The complete human PIWIL4 amino acid sequence can be found under GENBANK® Accession No. Q7Z3Z4.2 (GI: 116242716) (SEQ ID NO: 1). The complete human PIWIL4 nucleic acid sequence can be found under GENBANK® Accession No. NM 152431.2 (GI: 221316710) (SEQ ID NO: 2).

In embodiments, the anti-PIWI4 agent is an inhibitory nucleic acid. In embodiments, the inhibitory nucleic acid is an RNA interfering agent. An RNA interfering agent is any agent that interferes with or inhibits expression of a target gene by RNA interference (RNAi). Such RNA interfering agents include, but are not limited to, peptides, proteins, antisense molecules, ribozymes, small inhibitory nucleic acid sequences, for example but not limited to guide RNAs, small interfering RNA (siRNA), short hairpin RNA or small hairpin RNA (snRNA), a microRNA (miRNA), post-transcriptional gene silencing RNA (ptgsRNA), short interfering oligonucleotides, antisense nucleotides, aptamers, CRISPR RNAs, nucleic acid molecules including RNA molecules which are homologous to the target gene, e.g., a marker of the presently disclosed subject matter, or a fragment thereof, and any molecule which interferes with or inhibit expression of a target gene by RNA interference (RNAi). In some embodiments, the agent is an RNA interfering agent. In some embodiments, the RNA is small hairpin RNA (snRNA).

In embodiments, the inhibitory nucleic acid is a double-stranded RNA, siRNA, snRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

In embodiments, the inhibitory nucleic acid is an siRNA. In embodiments, the siRNA is a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

In embodiments, the inhibitory nucleic acid is a small hairpin (also called stem loop) RNA (snRNA). In embodiments, the snRNA is composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart et al. (2003) *RNA* 9:493-501).

In embodiments, the anti-PIWIL4 agent is an agent that acts at the transcriptional level. In embodiments, the anti-PIWIL4 agent is a transcriptional repressor, a nucleic acid sequence that encodes a transcriptional repressor, or an interfering agent involved in the CRISPR (clustered regularly interspaced palindromic repeats) pathway, such as a guide RNA or a CRISPR RNA.

In embodiments, the anti-PIWIL4 agent is an antibody. In embodiments, the antibody is an antagonist antibody or a blocking antibody effective to inhibits or reduce the expression or activity of PIWIL4, either directly or indirectly through a regulatory pathway, such as a signal transduction pathway, that regulates PIWIL4 expression at transcriptional or post-transcriptional levels. In embodiments, the antibody is a binding fragment produced by the modification of whole antibodies or synthesized de novo using recombinant DNA methodologies. Such fragments and methods for making them are described for example, in texts such as Fundamental Immunology, W. E. Paul, ed., Raven Press, N.Y. (1993). While various antibody fragments are defined in terms of the digestion of an intact antibody, one of skill will appreciate that such Fab' fragments may be synthesized de novo either chemically or by utilizing recombinant DNA methodology. In embodiments, the antibody is a single chain antibody, preferably a single chain Fv antibody (sFv or scFv) in which a variable heavy and a variable light chain are joined together (directly or through a peptide linker) to form a continuous polypeptide. Generally, a single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, F light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778).

In embodiments, the antibody is a recombinant antibody with an artificial sequence of amino acid residues. This antibody is screened from a combinatorial antibody library, such as recombinant antibodies selected from intracellular combinatorial libraries that prevent cell death (Xie et al. *Chem Biol.* 2014 Feb. 20; 21(2):274-83, incorporated herein by reference in its entirety).

In embodiments, the antibody has the catalytic activity to destroy PIWIL4 or its regulators, interacting partners, or target proteins. Such an catalytic antibody has been reported by Wentworth et al. in *Proc Natl Acad Sci USA*. 2000 Sep. 26; 97(20):10930-5, incorporated herein by reference in its entirety.

In embodiments, the antibody is a monoclonal antibody. In embodiments, the monoclonal antibody is a human or humanized antibody.

In embodiments, the anti-PIWIL4 agent is a PIWIL4 peptide.

In embodiments, the anti-PIWIL4 agent is a small molecule. The term small molecule in this context is meant to include organic or inorganic compounds (i.e., including heteroorganic and organometallic compounds) having a molecular weight less than about 10,000 grams per mole, or less than about 5,000 grams per mole, or less than about 1,000 grams per mole. In embodiments, a small molecule is an organic or inorganic compound having a molecular weight less than about 500 grams per mole, or less than about 100 grams per mole. Salts, esters, and other pharmaceutically acceptable forms of such compounds are also encompassed.

Methods of Treatment

The disclosure provides methods for the treatment of cancer in a subject in need thereof. In embodiments, the methods comprise reducing PIWIL4 expression and/or activity in the cells of the cancer. In embodiments, the methods comprise administering to the subject an anti-PIWIL4 agent in an amount effective to reduce the expression and/or activity of PIWIL4 in the cells of the cancer.

In embodiments, the anti-PIWIL4 agent is selected from the group consisting of an inhibitory nucleic acid, an antibody or fragment thereof, a peptide, a polypeptide or fragment thereof, and a small molecule. In embodiments, the anti-PIWIL4 agent is an inhibitory nucleic acid. In embodiments, the inhibitory nucleic acid is an RNAi molecule or a small hairpin RNA (snRNA).

As used herein, a "subject in need thereof" is a subject having a disease, disorder or condition, or a subject having an increased risk of developing a disease, disorder or condition relative to the population at large. In a preferred aspect, the subject in need thereof is a subject having cancer or having an increased risk of developing cancer relative to the population at large. In embodiments, the subject is a human cancer patient.

A "subject" includes a mammal. The mammal can be e.g., any mammal, e.g., a human, primate, mouse, rat, fowl, dog, cat, cow, horse, goat, camel, sheep or a pig. The terms "subject" and "patient" are used interchangeably herein. In embodiments, the subject is an animal, such as a domestic pet.

In embodiments, the cancer is a breast cancer. In embodiments, the breast cancer is an estrogen receptor-negative breast cancer, a progesterone receptor-negative breast cancer, or a human epidermal growth factor receptor 2 (HER2)-negative breast cancer. In embodiments, the breast cancer is negative for all three of estrogen receptor, progesterone receptor, and HER2, also referred to herein as "triple-negative breast cancer" or "TNBC". In embodiments, the breast cancer is triple-negative breast cancer.

In embodiments, the cancer is a melanoma, a central nervous system (CNS) cancer, a CNS germ cell tumor, a lung cancer, leukemia, multiple myeloma, a renal cancer, a malignant glioma, a medulloblatoma, a breast cancer, an ovarian cancer, a prostate cancer, a bladder cancer, a fibrosarcoma, a pancreatic cancer, a gastric cancer, a head and neck cancer, a skin cancer, or a colorectal cancer. For example, a cancer cell is derived from a solid cancer or hematological cancer. The hematological cancer is, e.g., a leukemia or a lymphoma. A leukemia is acute lymphoblastic leukemia (ALL), acute myelogenous leukemia (AML), chronic lymphocytic leukemia (CLL), small lymphocytic lymphoma (SLL), chronic myelogenous leukemia (CML), or acute monocytic leukemia (AMoL). A lymphoma is follicular lymphoma, Hodgkin's lymphoma (e.g., Nodular sclerosing subtype, mixed-cellularity subtype, lymphocyte-rich subtype, or lymphocyte depleted subtype), or Non-Hodgkin's lymphoma. Exemplary solid cancers include but are not limited to melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), and lung cancer (e.g., non-small cell lung cancer).

Combination Therapy

The disclosure also provides methods comprising combination therapy of an anti-PIWIL4 agent and at least one additional active agent. In embodiments, the at least one additional active agent is a therapeutic agent.

As used herein, "combination therapy" or "co-therapy" includes the administration of a therapeutically effective amount of an agent described herein with at least one additional active agent, as part of a specific treatment regimen intended to provide a beneficial effect from the co-action of the agent and the additional active agent. The beneficial effect of the combination includes, but is not limited to, pharmacokinetic or pharmacodynamic co-action resulting from the combination of therapeutically active compounds. "Combination therapy" is not intended to encompass the administration of two or more therapeutic compounds as part of separate monotherapy regimens that incidentally and arbitrarily result in a beneficial effect that was not intended or predicted.

Preferably, the combination therapy provides a synergistic response in the subject being treated. In this context, the term "synergistic" refers to the efficacy of the combination being more effective than the additive effects of either single therapy alone. The synergistic effect of a combination therapy according to the invention can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the agent that inhibits or reduces the biological activity and/or expression of a target protein (e.g., PIWIL4) of the present invention in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

The non-drug treatment can be selected from chemotherapy, radiation therapy, hormonal therapy, anti-estrogen therapy, gene therapy, and surgery.

In the context of the methods described herein, the amount of an agent administered to the subject is a therapeutically effective amount. The term "therapeutically effective amount" refers to an amount sufficient to treat, ameliorate a symptom of, reduce the severity of, or reduce the duration of the cancer being treated, or enhance or improve the therapeutic effect of another therapy, or sufficient to exhibit a detectable therapeutic effect in the subject. In one embodiment, the therapeutically effective amount of agent is the amount effective in reducing PIWIL4 expression and/or activity in the cells of the cancer.

In embodiments, the administration of an anti-PIWIL4 agent according to the methods described here leads to the elimination of a symptom or complication of the cancer being treated; however, elimination is not required. In one embodiment, the severity of the symptom or complication is decreased. In the context of cancer, such symptoms may include clinical markers of severity or progression including the degree to which a tumor secrets growth factors, degrades the extracellular matrix, becomes vascularized, loses adhesion to juxtaposed tissues, or metastasizes, as well as the number of metastases. Complications may include, for example, deleterious effects of the metastases on tissues and organs in which they appear.

In embodiments, the administration of an anti-PIWIL4 agent according to the methods described here results in a reduction in the size or volume of a tumor, preferably a metastasis. A reduction in size of a primary tumor or tumor metastasis may also be referred to as "tumor regression". In embodiments, the administration of an anti-PIWIL4 agent according to the methods described here results in a decrease in number of tumor metastases.

Pharmaceutical Compositions and Formulations

The anti-PIWIL4 agents for use in the methods described here are preferably in the form of pharmaceutically acceptable compositions suitable for use in humans or animals. In this context, the compositions may further comprise at least one pharmaceutically acceptable excipient or carrier.

The phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. "Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The disclosure also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use, one or more syringes, one or more applicators, or a sterile solution suitable for reconstituting the composition.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

More detail concerning the following examples can be found in *J. Biol. Chem.* 291 (20): 10646-10658, published May 13, 2016, e-published Mar. 8, 2016, the contents of which are hereby incorporated by reference in their entirety.

EXAMPLES

Example 1: The PIWIL4 Gene was Highly Expressed in Both Breast Cell Lines and Breast Cancer Samples PIWI proteins have been reported to have aberrant and ectopic expression in cancers, such as the expression of PIWIL2 in breast cancer (Kwon, C., et al (2014) *Biochem. Biophys. Res. Commun.* 446, 218-223, Chen, C., et al (2013) *Cancer Biomark.* 13, 315-321, Suzuki, R., et al (2012) *Front. Genet.* 3, 204, Wang, Y. et al (2012) *Int. J. Clin. Exp. Pathol.* 5, 315-325, Siddiqi, S., and Matushansky, I. (2012) *J. Cell. Biochem.* 113, 373-380, Qiao, D., et al (2002) *Oncogene* 21, 3988-3999, and Lee, J. H., et al (2010) *Cancer Res.* 70, 4569-4579).

Because all PIWI proteins are necessary for germ line development and stem cell self-renewal, the expression of three known active PIWI genes in humans (piwil1, piwil2, and piwil4), in six different types of human breast cancer cell lines and 20 pairs of normal and breast cancer samples from 20 patients were examined by quantitative RT-PCR (FIGS. 1A-1F). PIWI genes, piwil1 and piwil2, were expressed in four and two cell lines, respectively, at significantly higher levels than in a normal breast cell line (MCF-10A, a physiologically negative control) or a mouse breast cancer line (4T1), (FIGS. 1A and 1B), consistent with a previous report of PIWIL2 expression in breast cancer cells (Lee, J. H., et al (2010*Cancer Res.* 70, 4569-4579). Additionally, PIWIL1 was expressed at significantly higher levels compared with the normal tissue controls in two of 20 breast cancer samples (FIG. 1D). PIWIL2 was more highly expressed than PIWIL1 in one cancer cell line, MDA-MB-231 (FIG. 1B), and four of 20 breast cancer samples (FIG. 1E). Remarkably, PIWIL4 was expressed at very high levels in five of six cancer cell lines, much higher than both PIWIL1 and PIWIL2 (FIG. 1C). Furthermore, PIWIL4 was significantly expressed in nine of 20 breast cancer samples, with five samples displaying a more than 50-fold upregulation (FIG. 1F). These data indicated that, among the three PIWI genes known to be active, PIWIL4 showed the best correlation with breast cancer.

Figure 8:
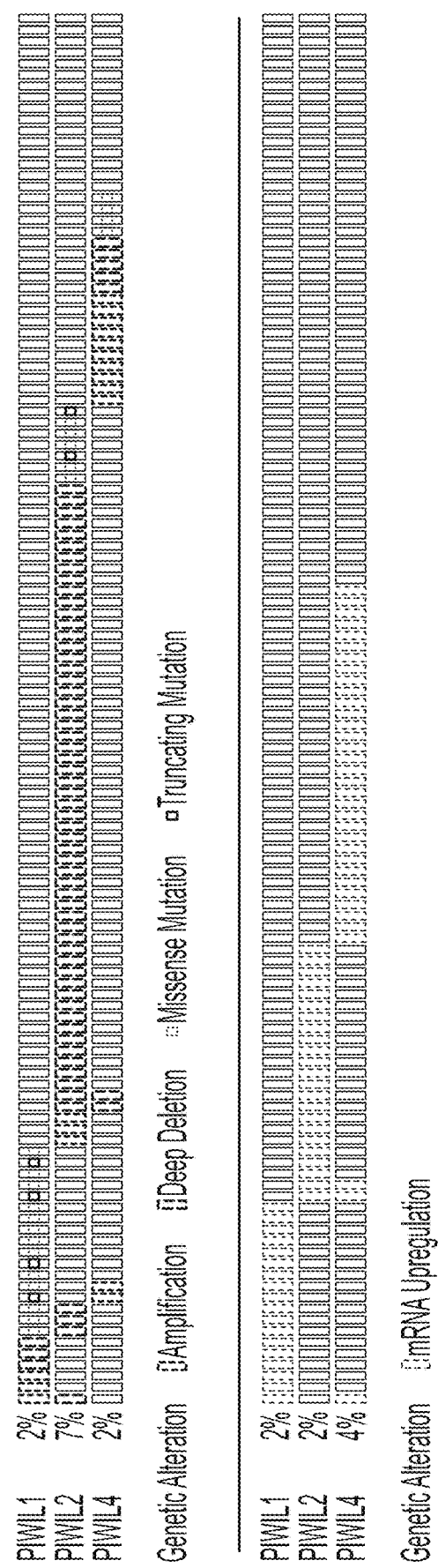
FIG. 8 depicts a graph showing that all three human PIWI genes had genetic alterations in breast cancer. It was found that 2%, 7%, and 2% of breast patients cancer patients had amplification, deletion, missense mutation, and truncation of PIWIL1, PIWIL2, and PIWIL4, respectively.

To further establish a functional correlation between the expression of PIWI proteins and breast cancer, a cancer genomics data bank, cBioPortal, was analyzed (Cerami, E., et al (2012) *Cancer Discov.* 2, 401-404, and Gao, J., et al (2013) *Sci. Signal.* 6, p11). The analysis showed that all three human PIWI genes had genetic alterations in breast cancer. It was found that 2%, 7%, and 2% of breast patients cancer patients had amplification, deletion, missense mutation, and truncation of PIWIL1, PIWIL2, and PIWIL4, respectively (FIG. 8). Moreover, 2%, 2%, and 4% of PIWIL1, PIWL2, and PIWIL4 patients had mRNA up-regulation (FIG. 8). When only considering TNBC patients, the percentage was increased to 11% (n=82). The 4% of PIWIL4-positive patients was apparently lower than the 9% of 20 patients who were examined directly. This may be due to inherently lower sensitivity associated with surveying the expression of many genes in more than 5000 tumor samples from 20 cancer studies. Alternatively, it may also reflect that 20 patients is a small sample size.

To investigate further correlation between PIWIL4 and breast cancer, a Kaplan-Meier survival analysis was conducted based on clinical data from a bioinformatics website, including 351-1616 patients for each analysis. Patients who had the upper tertile level of PIWIL4 expression also showed lower overall survival, distance metastasis-free survival, and post-progression survival than patients with the lower 67% of PIWIL4 expression (FIGS. 2A-2I). This analysis further correlated PIWIL4 to breast cancer.

Figure 3A:
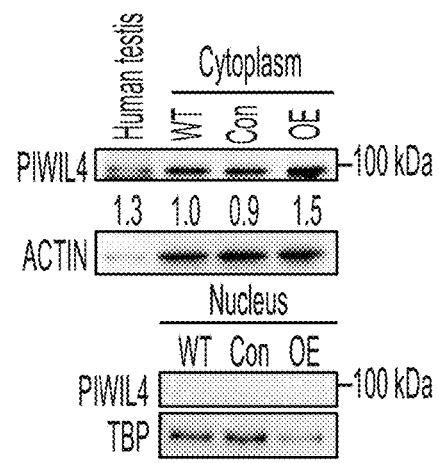
FIG. 3A depicts a Western blot indicating that PIWIL4 was present in the cytoplasm.

Example 2: The PIWIL4 Protein was Localized in the Cytoplasm and Exists in Multiple Isoforms in MDA-MB-231 Cells To further investigate the role of PIWIL4 in breast cancer, its expression and subcellular localization in MDA-MB-231 cells was examined. The cytoplasmic and nuclear fractions of the cell lysate were separated from MDA-MB-231 cells (WT), MDA-MB-231 cells transfected with an empty plasmid vector (Con), and MDAMB-231 cells transfected with a PIWIL4-overexpressing construct in the vector (OE) by centrifugation, followed by Western blotting, which revealed that PIWIL4 was present in the cytoplasm (FIG. 3A).

Figure 3B:
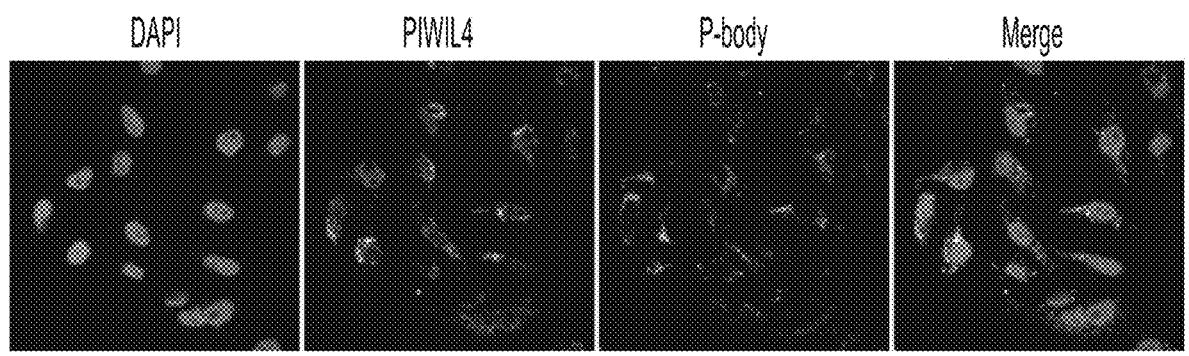
FIG. 3B depicts immunofluorescence microscopy results which indicated that PIWIL4 was present in the cytoplasm and further showed that it was not co-localized with the P body.

Immunofluorescence microscopy results confirmed that PIWIL4 was present in the cytoplasm and further showed that it is not co-localized with the P body (FIG. 3B). Surprisingly, not all MDA-MB-231 cells showed a PIWIL4 signal when stained with anti-PIWIL4 antibody against 639-839 amino acid residues (in exons 15-20) of PIWIL4

Figure 3C:
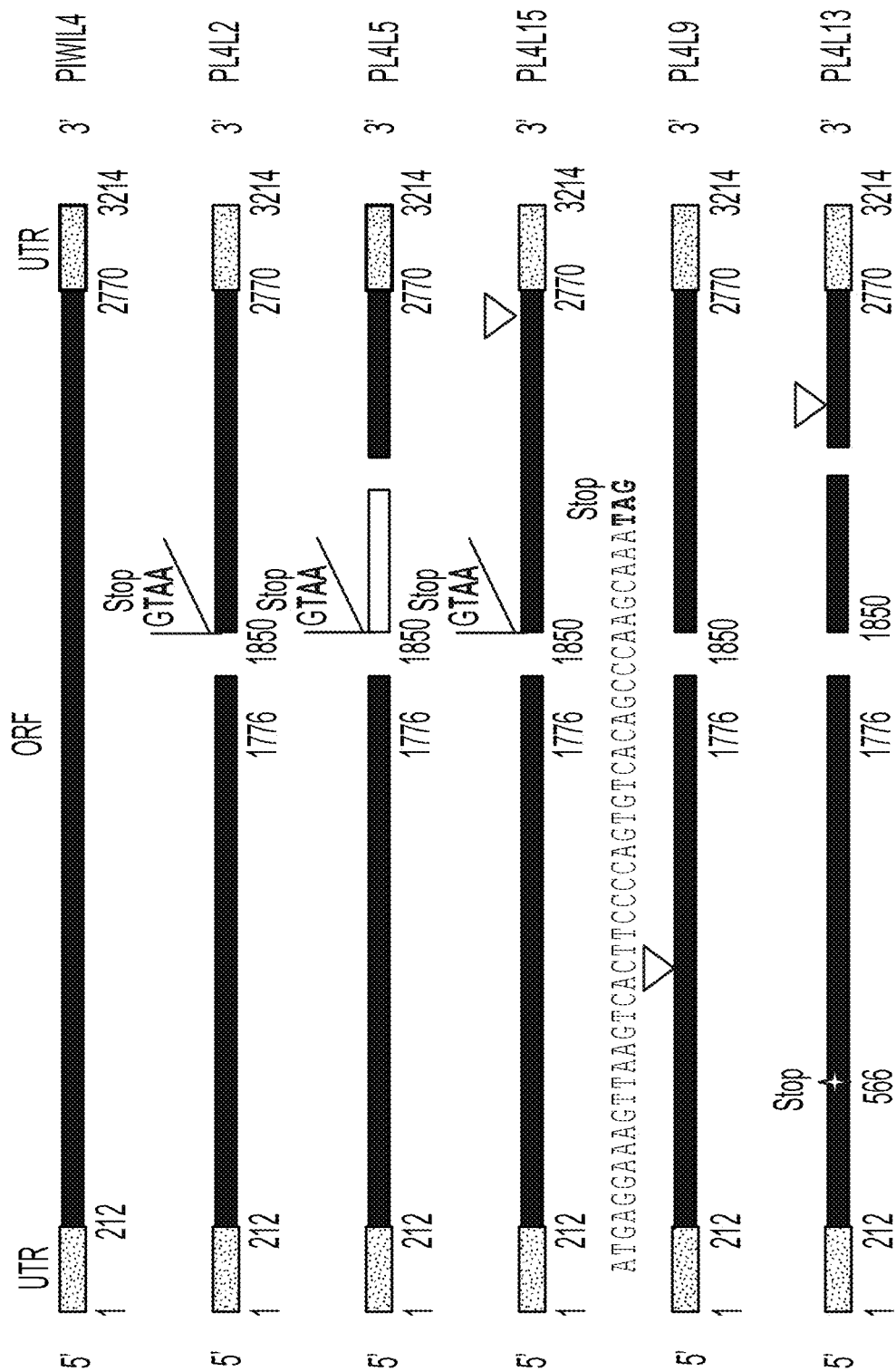
FIG. 3C depicts sequence analysis of cDNAs from PIWIL4 mRNAs isolated from MDA-MB-231 cells that were reverse-transcribed. These analyses revealed that there were five variants of PIWIL4 transcripts in MDA-MB-231 cells.
Figure 3D:
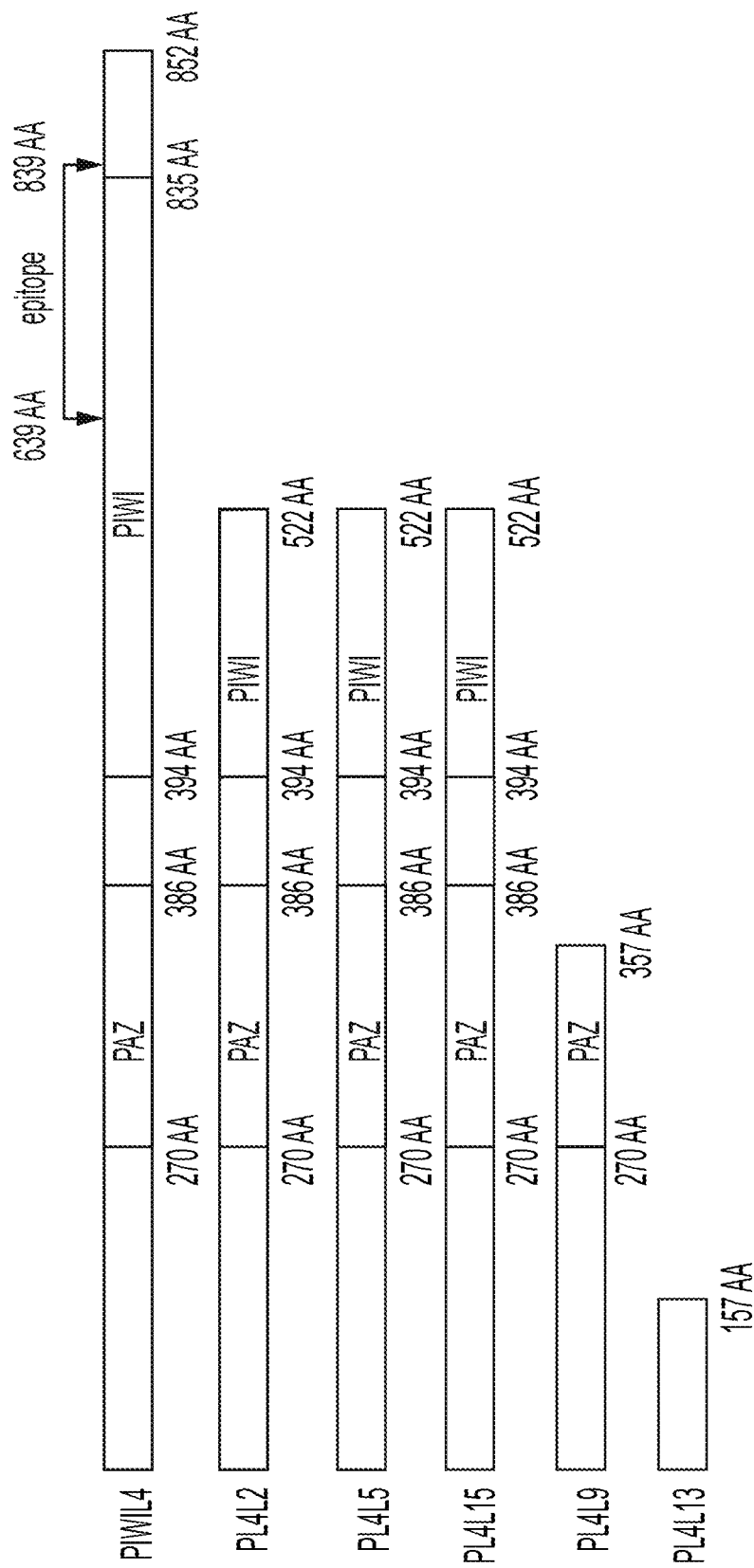
FIG. 3D depicts data indicating that all of the variants had deletions or insertions that caused premature termination before the 639-839 amino acid residues of PIWIL4. The inserted sequences in PL4L9, PL4L13, and PL4L15 were all intron sequences of the PIWIL4 gene. Correspondingly, there were three aberrant PIWIL4 protein isoforms.
Figure 9:
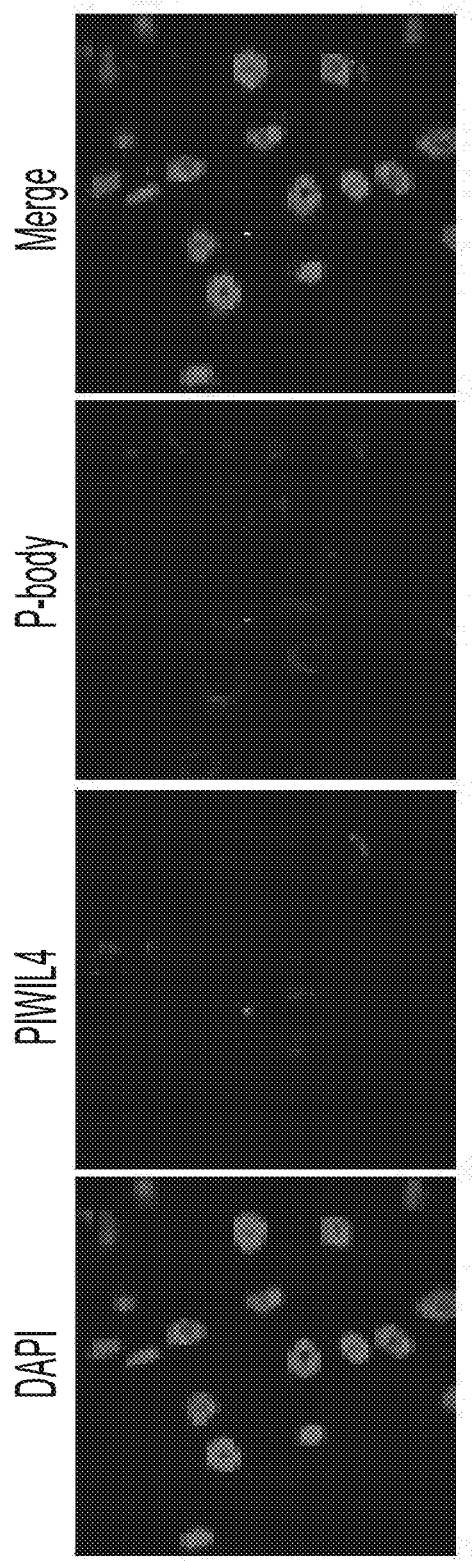
FIG. 9 depicts images showing that not all MDA-MB-231 cells showed a PIWIL4 signal when stained with anti-PIWIL4 antibody against 639-839 amino acid residues (in exons 15-20) of PIWIL4.

(FIGS. 3B and 3D, and FIG. 9). This indicated that these cells either did not express PIWIL4, or that they express aberrant PIWIL4 isoforms that lack 639-839 amino acid residues. To discriminate between these two possibilities, PIWIL4 mRNAs isolated from MDA-MB-231 cells were reverse-transcribed and the resulting cDNAs were sequenced. These analyses revealed that there were five variants of PIWIL4 transcripts in MDA-MB-231 cells (FIG. 3C). All of the variants had deletions or insertions that caused premature termination before the 639-839 amino acid residues of PIWIL4 (FIG. 3D). The inserted sequences in PL4L9, PL4L13, and PL4L15 were all intron sequences of the PIWIL4 gene. Correspondingly, there were three aberrant PIWIL4 protein isoforms (FIG. 3D). These observations indicated the instability of the MDA-MB-231 genome, which was a typical situation in many cancer cell lines.

Example 3: PIWIL Inhibited MDA-MB-231 Cell Apoptosis and Promoted Migration

Figure 4A:
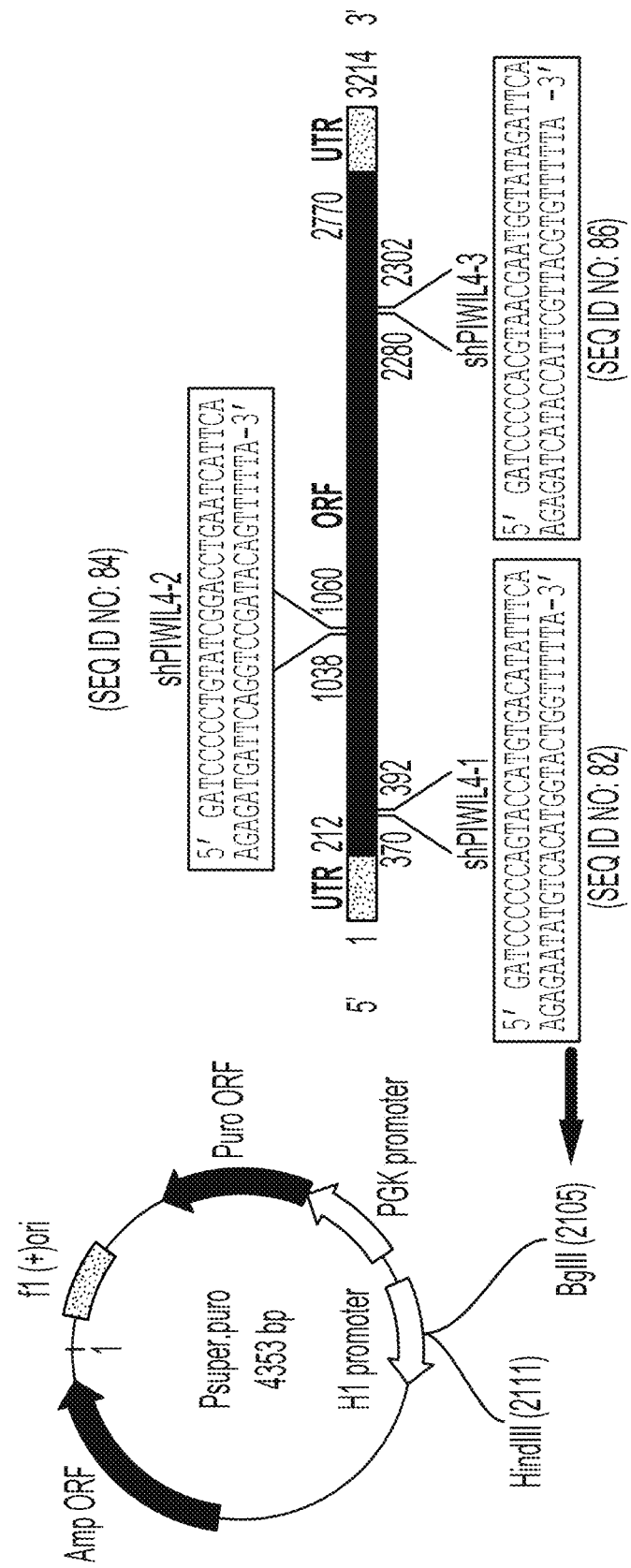
FIG. 4A depicts a diagram indicating three shRNA-corresponding regions in PIWIL4 mRNA (at exon 2-exon 3 junction, exon 7, and exon 17, respectively). The oligo sequences labeled shPIWIL4-1, shPIWIL4-2 and shPIWIL4-3 correspond to SEQ ID NO: 82, SEQ ID NO: 84 and SEQ ID NO: 86, respectively.
Figure 4B:
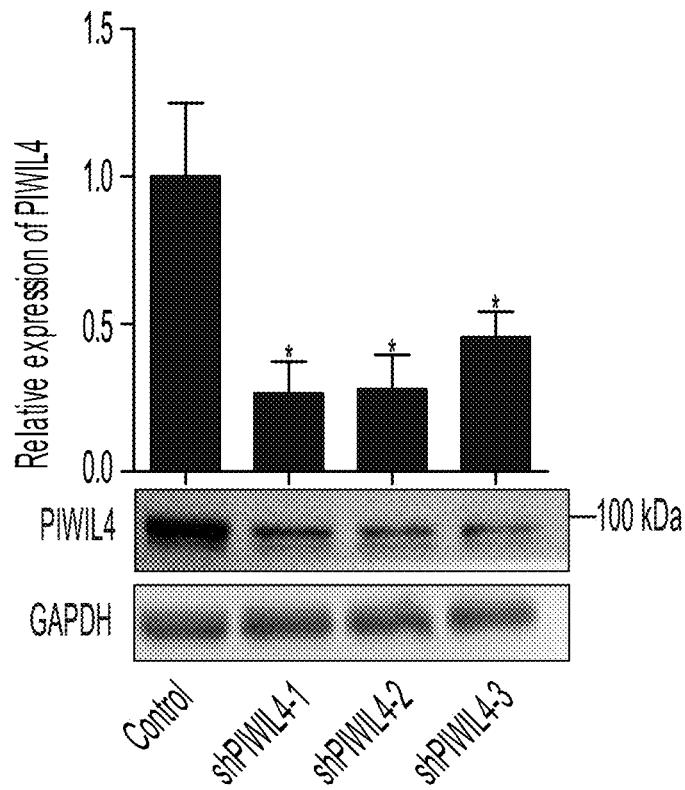
FIG. 4B depicts a graph and a Western blot indicating that three shRNAs effectively reduced both PIWIL4 mRNA and PIWIL4 protein levels.
Figure 4C:
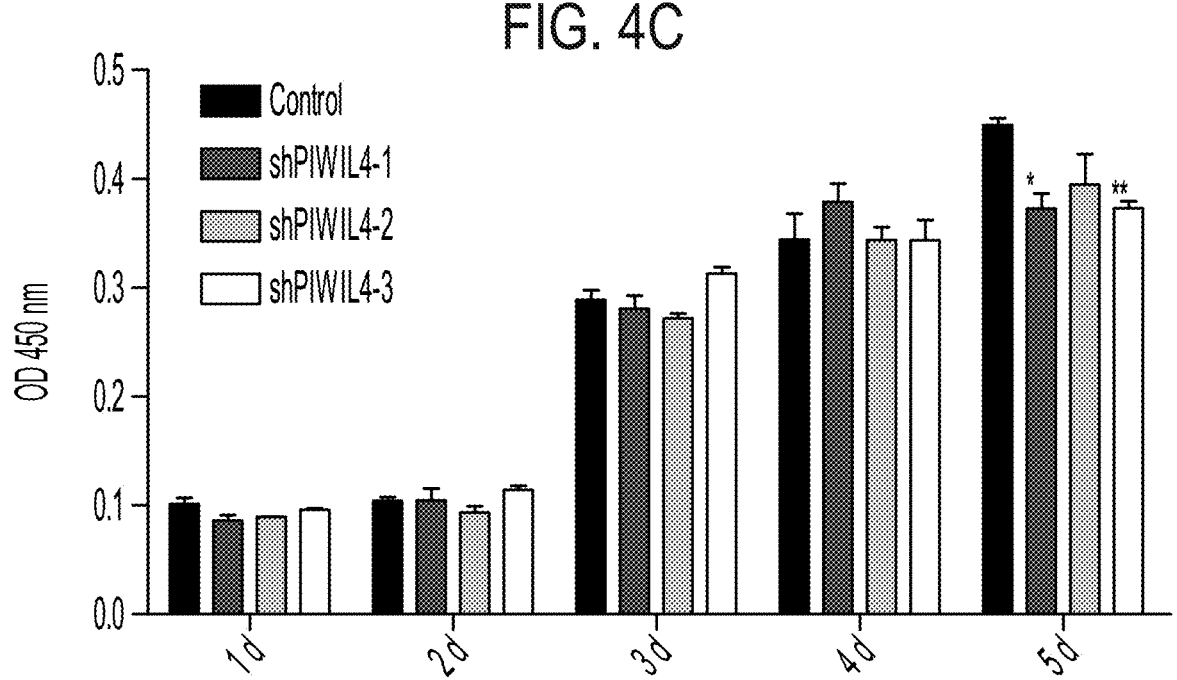
FIG. 4C depicts a graph showing that the reduction of PIWIL4 weakly inhibited cell proliferation.
Figure 4D:
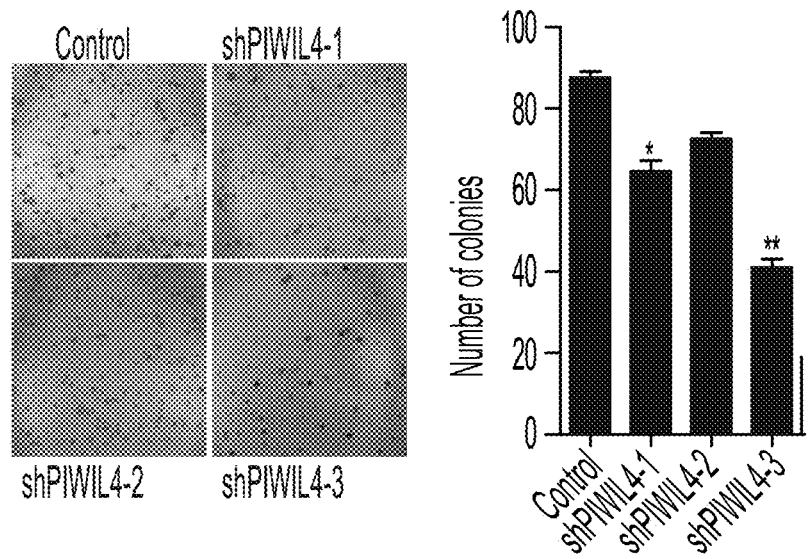
FIG. 4D depicts images showing that reduction of PIWIL4 weakly inhibited colony formation.
Figure 4E:
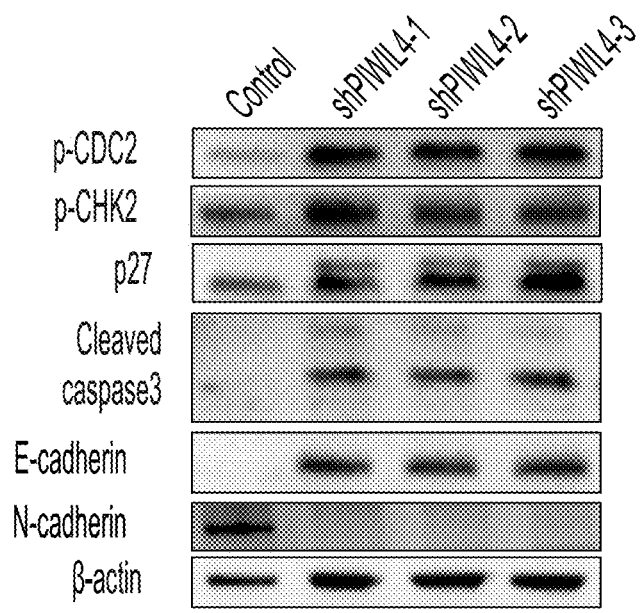
FIG. 4E depicts a Western blot indicating that PIWIL4 knockdown increased the levels of phosphorylated CHK2 and phosphorylated CDC2 (two G2 phase checkpoint markers) and p27 (a cell proliferation marker) and drastically increased the level of cleaved caspase 3, an indicator of the activation of the caspase 3 pathway. Additionally, the expression of E-cadherin, N-cadherin, in MDA-MB-231 cells was examined by Western blotting analysis. Knocking down PIWIL4 abolished N-cadherin expression but induced strong expression of E-cadherin.
Figure 4F:
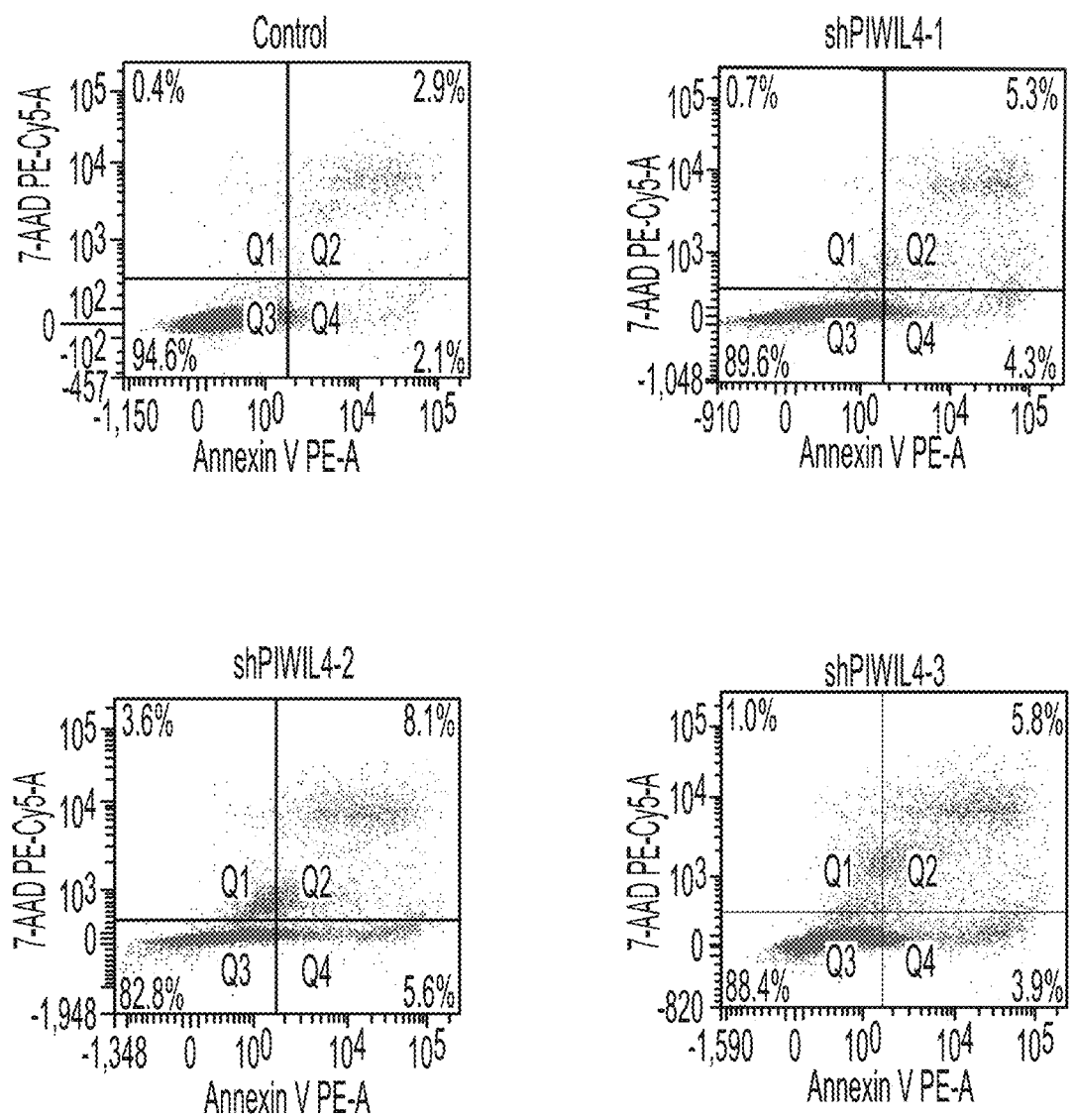
FIG. 4F depicts flow cytometry data indicating that reduction of PIWIL4 significantly increased apoptosis.

To reveal the effect of ectopic PIWIL4 expression in cancer cells, PIWIL4 expression was knocked down using the pSuper-shRNA knockdown system with three different shRNA sequences against PIWIL4 mRNA. The effect of the knockdowns on the function of MDA-MB-231 cells was analyzed. FIG. 4A indicates the three shRNA-corresponding regions in PIWIL4 mRNA (i.e. at the exon 2-exon 3 junction (shPIWIL4-1 (SEQ ID NO: 82)), exon 7 (shPIWIL4-2 (SEQ ID NO: 84)), and exon 17 (shPIWIL4-3 (SEQ ID NO: 86))). All three of these shRNAs effectively reduced both PIWIL4 mRNA and PIWIL4 protein levels (FIG. 4B). Reduction of PIWIL4 weakly inhibited cell proliferation (FIG. 4C) and colony formation ability (FIG. 4D) but caused significantly increased apoptosis (FIG. 4F). Correspondingly, PIWIL4 knockdown increased the levels of phosphorylated CHK2 and phosphorylated CDC2 (two G2 phase checkpoint markers) and p27 (a cell proliferation marker) and drastically increased the level of cleaved caspase 3, an indicator of the activation of the caspase 3 pathway (FIG. 4E). These results validated the negative impact of PIWIL4 knockdown on cancer cell survival.

To explore whether PIWIL4 also had a role in the migration and metastasis of cancer cells, the in vitro wound healing assay (i.e. the scratch assay) and the transwell migration assay were conducted on MDA-MB-231 cells. Knocking down PIWIL4 with each of the three anti-PIWIL4 shRNAs significantly inhibited the migration ability of these cells by either the scratch assay (FIG. 4G) or the transwell assay (FIG. 4H). These results indicated that PIWIL4 promoted the migratory ability of MDA-MB-231 cells.

To further investigate whether the PIWIL4-dependent migratory ability of MDA-MB-231 cells reflected their epithelial to-mesenchymal transition, the expression of a key epithelial marker, E-cadherin, and a key mesenchymal marker, N-cadherin, in MDA-MB-231 cells were examined by Western blotting analysis. These cells normally express only N-cadherin but not E-cadherin (FIG. 4E), indicating that these cancer cells acquired the mesenchymal fate. Remarkably, knocking down PIWIL4 abolished N-cadherin expression but induced strong expression of E-cadherin (FIG. 4E). These data indicated that the PIWIL4-deficient MDA-MB-231 cells had abandoned the mesenchymal fate and had reacquired key features of the epithelial fate. Therefore, PIWIL4 was required for the epithelial-tomesenchymal transition and acquisition of the migratory ability of MDA-MB-231 cells.

Example 4: PIWIL4 Activated TGF-β and FGF Signaling in MDA-MB-231 Cells

Figure 5A:
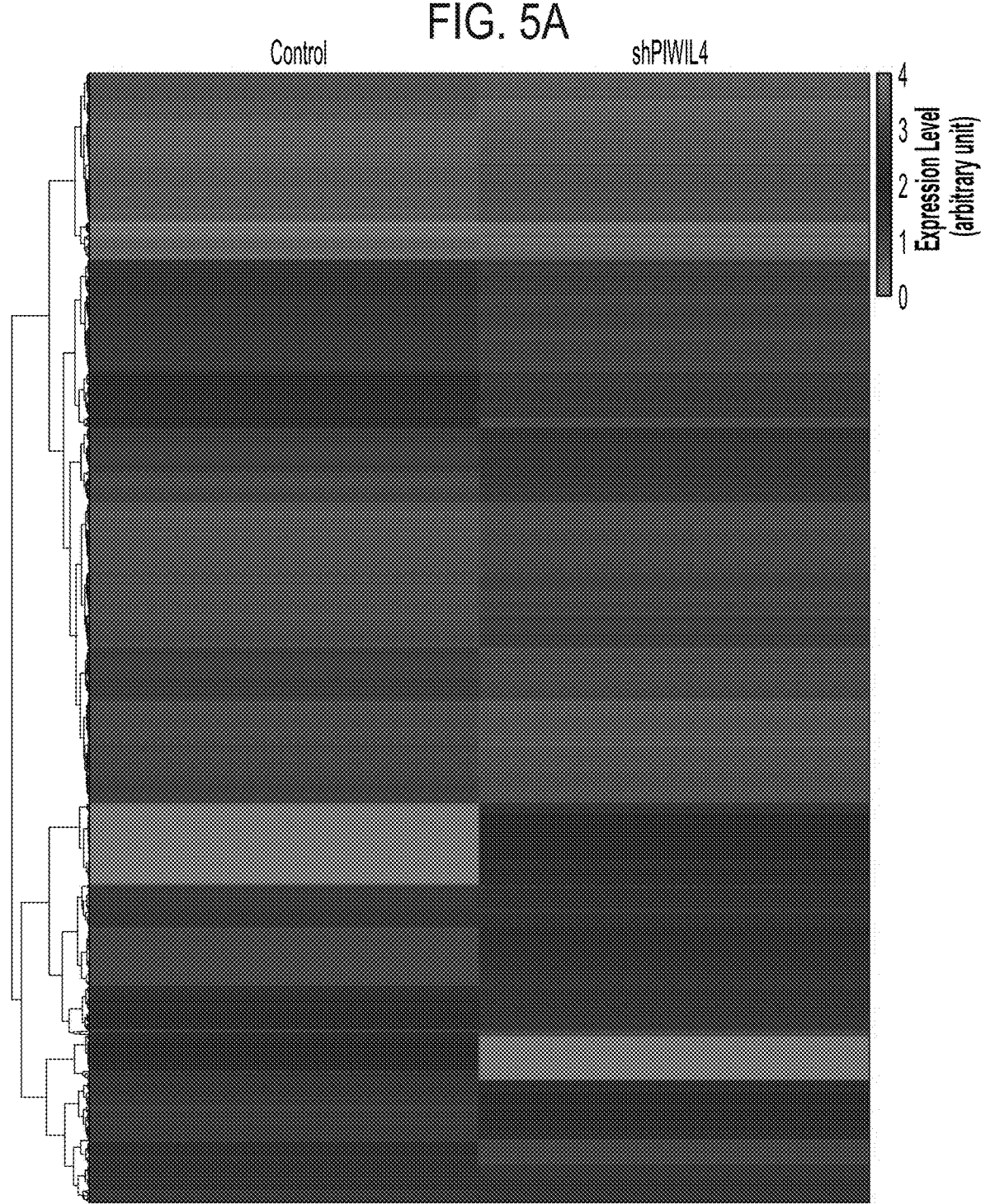
FIG. 5A depicts a heatmap depicting the transcriptome and proteome of MDA-MB-231 cells with and without shPIWIL4-3 knockdown was examined by deep sequencing of mRNAs and mass spectrometry of total cellular lysate. Among 26,057 mRNAs that were detected by at least one read in MDA-MB-231 cells via deep sequencing, 332 mRNAs were significantly down-regulated but 400 mRNAs were up-regulated when PIWIL4 was knocked down.

To investigate the molecular mechanism underlying PIWIL4 function in MDA-MB-231 cancer cells, the transcriptome and proteome of MDA-MB-231 cells with and without shPIWIL4-3 knockdown was examined by deep sequencing of mRNAs and mass spectrometry of total cellular lysate, respectively. Among 26,057 mRNAs that were detected by at least one read in MDA-MB-231 cells via deep sequencing, 332 mRNAs were significantly down-regulated but 400 mRNAs were up-regulated when PIWIL4 was knocked down, as summarized in the heat map in FIG. 5A. The 60 most up- and down-regulated genes (38 up-regulated and 22 downregulated) are shown with names in FIG. 5B.

Figure 5C:
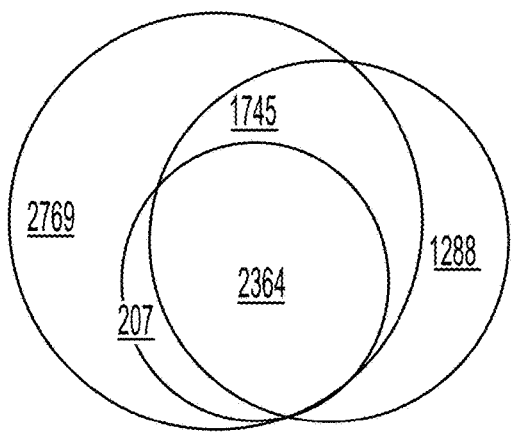
FIG. 5C depicts a diagram showing that the three PIWIL4 knockdown samples showed overlapping protein profiles (49.74% overlap between shPIWIL4-1 and shPIWIL4-2, 50.41% overlap between shPIWIL4-1 and shPIWIL4-3, 50.98% overlap between shPIWIL4-2 and shPIWIL4-3, and 36.47% were found in all three samples), with 2571 proteins detected in all three PIWIL4 knockdown samples.

To detect the impact of PIWIL4 knockdown on the cellular protein profile, mass spectrometry analyses was performed of MDA-MB-231 cells and MDA-MB-231 cells with PIWIL4 knocked down by the three different shRNAs. The three PIWIL4 knockdown samples showed nicely overlapping protein profiles (49.74% overlap between shPIWIL4-1 and shPIWIL4-2, 50.41% overlap between shPIWIL4-1 and shPIWIL4-3, 50.98% overlap between shPIWIL4-2 and shPIWIL4-3, and 36.47% were found in all three samples), with 2571 proteins detected in all three PIWIL4 knockdown samples (FIG. 5C). Of the 2571 proteins, 2364 proteins were also present in MDA-MB-231 cells without PIWIL4 knockdown. Only 207 proteins were not detected in normal cancer cells. This suggested that reducing PIWIL4 expression did not significantly activate the expression of new proteins. However, 1288 proteins were not detectable in any of the three PIWIL4 knockdown samples. This indicated that PIWIL4 promoted the expression of many proteins in MDA-MB-231 cancer cells.

Figure 11A:
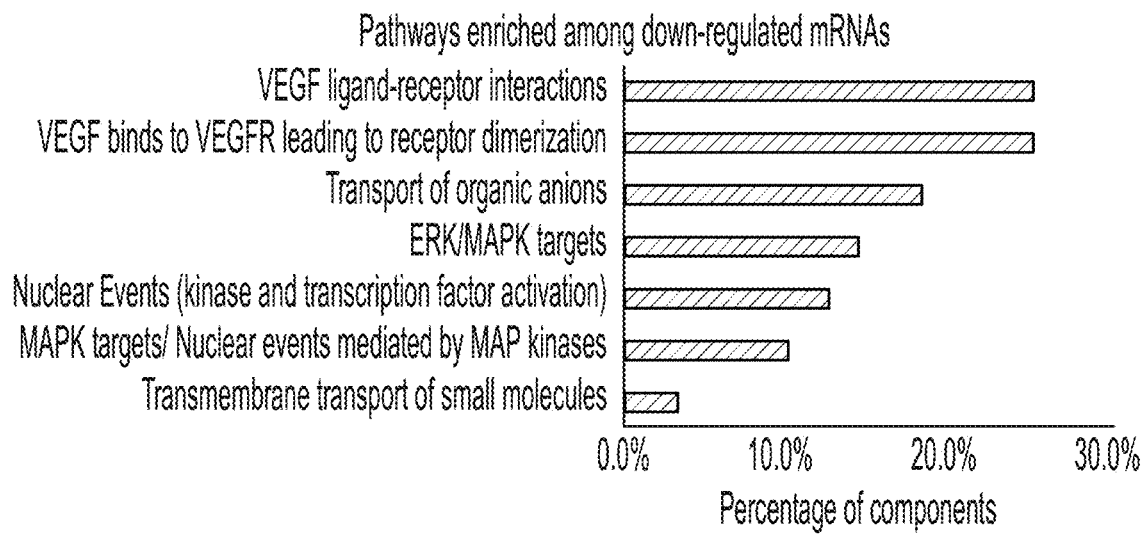
FIG. 11A depicts a graph showing the pathway enrichment analysis results of the pathways enriched among down-regulated mRNAs.

To investigate which mRNAs were down-regulated and which proteins became undetected under the PIWIL4 deficiency condition, a pathway enrichment analysis was conducted of the 332 most down-regulated mRNAs and the 1288 proteins that are only detected in MDA-MB-231 cancer cells without PIWIL4 knockdown. These analyses showed that MAPK-ERK, TGF-β, and FGF were the most enriched pathways (FIG. 5E and FIG. 11A). Full lists are shown in Tables 2 and 3 below and include TGFβR1, TGFβR2, FGFR2, TGFβ1, and TGFβ3, which are no longer detectable in the three PIWIL4 knockdown samples.

TABLE 2

Pathway analysis of 332 shPIWIL4-down-regulated mRNAs

| Pathway name | Set size | candidates contained | candidates contained (%) | p-value | q-value | pathway source |
|---|---|---|---|---|---|---|
| Histidine metabolism | 35 | 5 | 14.30% | 0.00012 | 0.0674 | EHMN |
| VEGF binds to VEGFR leading to receptor dimerization | 8 | 2 | 25.00% | 0.00518 | 0.109 | Reactome |

TABLE 2-continued

Pathway analysis of 332 shPIWIL4-down-regulated mRNAs

| Pathway name | Set size | candidates contained | candidates contained (%) | p-value | q-value | pathway source |
|---|---|---|---|---|---|---|
| Folate biosynthesis - *Homo sapiens* (human) | 14 | 3 | 21.40% | 0.00088 | 0.109 | KEGG |
| Mycophenolic Acid Metabolism Pathway | 16 | 3 | 18.80% | 0.00132 | 0.109 | SMPDB |
| Rheumatoid arthritis - *Homo sapiens* (human) | 89 | 6 | 6.70% | 0.00154 | 0.109 | KEGG |
| Melatonin metabolism and effects | 17 | 3 | 17.60% | 0.00159 | 0.109 | Wikipathways |
| Mycophenolic acid Pathway, Pharmacokinetics | 17 | 3 | 17.60% | 0.00159 | 0.109 | PharmGKB |
| Statin Pathway - Generalized, Pharmacokinetics | 20 | 3 | 15.00% | 0.00259 | 0.109 | PharmGKB |
| Rap1 signaling pathway - *Homo sapiens* (human) | 211 | 9 | 4.30% | 0.00289 | 0.109 | KEGG |
| VEGF ligand-receptor interactions | 8 | 2 | 25.00% | 0.00518 | 0.109 | Reactome |
| Tyrosine metabolism | 106 | 6 | 5.70% | 0.00372 | 0.109 | EHMN |
| Paclitaxel Action Pathway | 7 | 2 | 28.60% | 0.00392 | 0.109 | SMPDB |
| Docetaxel Action Pathway | 7 | 2 | 28.60% | 0.00392 | 0.109 | SMPDB |
| Vitamin D Receptor Pathway | 184 | 8 | 4.40% | 0.00423 | 0.109 | Wikipathways |
| Transport of organic anions | 11 | 2 | 18.20% | 0.00989 | 0.109 | Reactome |
| ERK/MAPK targets | 21 | 3 | 14.30% | 0.00299 | 0.109 | Reactome |
| Nuclear Events (kinase and transcription factor activation) | 24 | 3 | 12.50% | 0.00441 | 0.109 | Reactome |
| Vitamin A (retinol) metabolism | 26 | 3 | 11.50% | 0.00555 | 0.109 | EHMN |
| Leukocyte transendothelial migration - *Homo sapiens* (human) | 118 | 6 | 5.10% | 0.00627 | 0.109 | KEGG |
| Bile acid biosynthesis | 53 | 4 | 7.50% | 0.00639 | 0.109 | EHMN |
| Pravastatin Pathway, Pharmacokinetics | 9 | 2 | 22.20% | 0.00659 | 0.109 | PharmGKB |
| VEGF and VEGFR signaling network | 10 | 2 | 20.00% | 0.00817 | 0.109 | PID |
| putrescine degradation III | 10 | 2 | 20.00% | 0.00817 | 0.109 | HumanCyc |
| Nicotine Pathway, Pharmacokinetics | 10 | 2 | 20.00% | 0.00817 | 0.109 | PharmGKB |
| MAPK targets/ Nuclear events mediated by MAP kinases | 30 | 3 | 10.00% | 0.00832 | 0.109 | Reactome |
| Transmembrane transport of small molecules | 579 | 19 | 3.30% | 0.00046 | 0.109 | Reactome |

TABLE 3

Pathway analysis of 1288 proteins detectable only in control MDA-MB-231 cells.

| Pathway name | set size | candidates contained | p-value | q-value | pathway source |
|---|---|---|---|---|---|
| Starch and sucrose metabolism - *Homo sapiens* (human) | 56 | 21 (37.5%) | 9.78E−07 | 0.00231 | KEGG |
| Drug metabolism - cytochrome P450 - *Homo sapiens* (human) | 68 | 22 (32.4%) | 9.20E−06 | 0.0109 | KEGG |
| Vitamin A (retinol) metabolism | 26 | 12 (46.2%) | 1.81E−05 | 0.0143 | EHMN |
| Glucuronidation | 20 | 10 (50.0%) | 3.88E−05 | 0.0207 | Reactome |
| Retinol metabolism - *Homo sapiens* (human) | 65 | 20 (30.8%) | 5.26E−05 | 0.0207 | KEGG |
| Drug metabolism - other enzymes - *Homo sapiens* (human) | 46 | 16 (34.8%) | 5.61E−05 | 0.0207 | KEGG |
| Chemical carcinogenesis - *Homo sapiens* (human) | 81 | 23 (28.4%) | 6.12E−05 | 0.0207 | KEGG |
| Porphyrin metabolism | 34 | 13 (38.2%) | 9.13E−05 | 0.027 | EHMN |
| Glucuronidation | 26 | 11 (42.3%) | 0.000109 | 0.0285 | Wikipathways |
| Endohydrolysis of 1,4-alpha-D-glucosidic linkages in polysaccharides by alpha-amylase | 6 | 5 (83.3%) | 0.00014 | 0.0332 | EHMN |
| Ascorbate and aldarate metabolism - *Homo sapiens* (human) | 27 | 11 (40.7%) | 0.000163 | 0.0351 | KEGG |
| Biological oxidations | 185 | 39 (21.7%) | 0.000193 | 0.038 | Reactome |
| Aryl Hydrocarbon Receptor Pathway | 46 | 15 (32.6%) | 0.000218 | 0.038 | Wikipathways |
| Xenobiotics metabolism | 51 | 16 (31.4%) | 0.000225 | 0.038 | EHMN |
| Regulation of RhoA activity | 48 | 15 (31.9%) | 0.000285 | 0.0449 | PID |
| Regulation of RAC1 activity | 39 | 13 (34.2%) | 0.000334 | 0.0494 | PID |
| Metabolism of xenobiotics by cytochrome P450 - *Homo sapiens* (human) | 74 | 20 (27.0%) | 0.000374 | 0.0521 | KEGG |
| Transcriptional regulation of white adipocyte differentiation | 44 | 14 (31.8%) | 0.000467 | 0.0614 | Reactome |
| Irinotecan Pathway, Pharmacodynamics | 14 | 7 (50.0%) | 0.0006 | 0.0746 | PharmGKB |
| Phase II conjugation | 99 | 23 (24.5%) | 0.000671 | 0.0793 | Reactome |
| Pentose and glucuronate interconversions - *Homo sapiens* (human) | 36 | 12 (33.3%) | 0.000736 | 0.0829 | KEGG |
| Porphyrin and chlorophyll metabolism - *Homo sapiens* (human) | 42 | 13 (31.0%) | 0.00099 | 0.106 | KEGG |
| Steroid hormone biosynthesis - *Homo sapiens* (human) | 58 | 16 (27.6%) | 0.0011 | 0.113 | KEGG |
| EPHA forward signaling | 33 | 11 (33.3%) | 0.00122 | 0.115 | PID |
| Collagen biosynthesis and modifying enzymes | 64 | 17 (26.6%) | 0.00124 | 0.115 | Reactome |
| Internalization of ErbB1 | 38 | 12 (31.6%) | 0.00126 | 0.115 | PID |
| 3-phosphoinositide degradation | 20 | 8 (40.0%) | 0.0015 | 0.124 | HumanCyc |
| nfkb activation by nontypeable *hemophilus influenzae* | 29 | 10 (34.5%) | 0.00151 | 0.124 | BioCarta |
| Scavenging of heme from plasma | 12 | 6 (50.0%) | 0.00151 | 0.124 | Reactome |
| EPH-ephrin mediated repulsion of cells | 30 | 10 (33.3%) | 0.00202 | 0.159 | Reactome |
| Digestion of dietary carbohydrate | 9 | 5 (55.6%) | 0.00215 | 0.164 | Reactome |
| D-myo-inositol (1,4,5)-trisphosphate degradation | 13 | 6 (46.2%) | 0.00253 | 0.178 | HumanCyc |
| SMAD2/3 Phosphorylation Motif Mutants in Cancer | 6 | 4 (66.7%) | 0.00264 | 0.178 | Reactome |
| SMAD2/3 MH2 Domain Mutants in Cancer | 6 | 4 (66.7%) | 0.00264 | 0.178 | Reactome |
| Loss of Function of SMAD2/3 in Cancer | 6 | 4 (66.7%) | 0.00264 | 0.178 | Reactome |

TABLE 3-continued

Pathway analysis of 1288 proteins detectable only in control MDA-MB-231 cells.

| Pathway name | set size | candidates contained | p-value | q-value | pathway source |
|---|---|---|---|---|---|
| ECM-receptor interaction - Homo sapiens (human) | 87 | 20 (23.0%) | 0.00324 | 0.213 | KEGG |
| Synthesis of PIPs at the plasma membrane | 33 | 10 (30.3%) | 0.00443 | 0.276 | Reactome |
| Pregnane X Receptor pathway | 33 | 10 (30.3%) | 0.00443 | 0.276 | Wikipathways |
| Anchoring of the basal body to the plasma membrane | 90 | 20 (22.2%) | 0.00488 | 0.287 | Reactome |
| Glutamatergic synapse - Homo sapiens (human) | 116 | 24 (20.9%) | 0.00512 | 0.287 | KEGG |
| Signaling by TGF-beta Receptor Complex in Cancer | 7 | 4 (57.1%) | 0.00556 | 0.287 | Reactome |
| Fanconi Anemia pathway | 24 | 8 (33.3%) | 0.00562 | 0.287 | Reactome |
| glutathione-mediated detoxification | 24 | 8 (33.3%) | 0.00562 | 0.287 | HumanCyc |
| Mitotic Prometaphase | 110 | 23 (20.9%) | 0.00591 | 0.287 | Reactome |
| Recruitment of NuMA to mitotic centrosomes | 11 | 5 (45.5%) | 0.00639 | 0.287 | Reactome |
| TGFBR2 Kinase Domain Mutants in Cancer | 4 | 3 (75.0%) | 0.00647 | 0.287 | Reactome |
| Loss of Function of TGFBR2 in Cancer | 4 | 3 (75.0%) | 0.00647 | 0.287 | Reactome |
| TGFBR1 KD Mutants in Cancer | 4 | 3 (75.0%) | 0.00647 | 0.287 | Reactome |
| Loss of Function of TGFBR1 in Cancer | 4 | 3 (75.0%) | 0.00647 | 0.287 | Reactome |
| Astrocytic Glutamate-Glutamine Uptake And Metabolism | 4 | 3 (75.0%) | 0.00647 | 0.287 | Reactome |
| Neurotransmitter uptake and Metabolism In Glial Cells | 4 | 3 (75.0%) | 0.00647 | 0.287 | Reactome |
| Binding and Uptake of Ligands by Scavenger Receptors | 40 | 11 (27.5%) | 0.00655 | 0.287 | Reactome |
| Glutathione metabolism - Homo sapiens (human) | 51 | 13 (25.5%) | 0.00655 | 0.287 | KEGG |
| PI Metabolism | 51 | 13 (25.5%) | 0.00655 | 0.287 | Reactome |
| Glutathione conjugation | 37 | 10 (28.6%) | 0.00701 | 0.289 | Reactome |
| superpathway of D-myo-inositol (1,4,5)-trisphosphate metabolism | 20 | 7 (35.0%) | 0.00702 | 0.289 | HumanCyc |
| Phenytoin Pathway, Pharmacokinetics | 20 | 7 (35.0%) | 0.00702 | 0.289 | PharmGKB |
| Endocytosis - Homo sapiens (human) | 258 | 45 (17.4%) | 0.00724 | 0.289 | KEGG |
| Androgen and estrogen biosynthesis and metabolism | 87 | 19 (21.8%) | 0.00728 | 0.289 | EHMN |
| Regulation of CDC42 activity | 30 | 9 (30.0%) | 0.00733 | 0.289 | ND |
| Ibuprofen Pathway, Pharmacokinetics | 16 | 6 (37.5%) | 0.00855 | 0.332 | PharmGKB |
| Resolution of Sister Chromatid Cohesion | 101 | 21 (20.8%) | 0.00884 | 0.335 | Reactome |
| Fanconi anemia pathway - Homo sapiens (human) | 53 | 13 (24.5%) | 0.0092 | 0.335 | KEGG |
| TGF_beta_Receptor | 174 | 32 (18.5%) | 0.00932 | 0.335 | NetPath |
| Valproic Acid Pathway, Pharmacokinetics | 21 | 7 (33.3%) | 0.00945 | 0.335 | PharmGKB |
| EPH-Ephrin signaling | 77 | 17 (22.1%) | 0.00966 | 0.335 | Reactome |
| NF-kB activation through FADD/RIP-1 pathway mediated by caspase-8 and -10 | 12 | 5 (41.7%) | 0.00988 | 0.335 | Reactome |
| Iron metabolism in placenta | 12 | 5 (41.7%) | 0.00988 | 0.335 | Wikipathways |

Figure 5D:
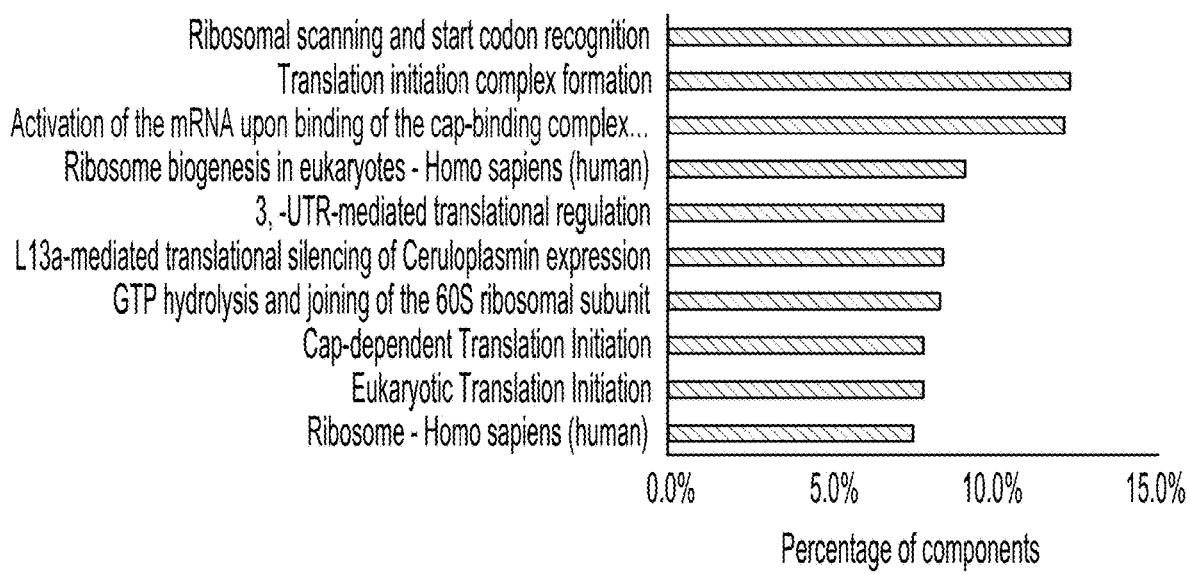
FIG. 5D depicts a graph showing the pathways enriched among proteins with shPIWIL4.
Figure 5F:
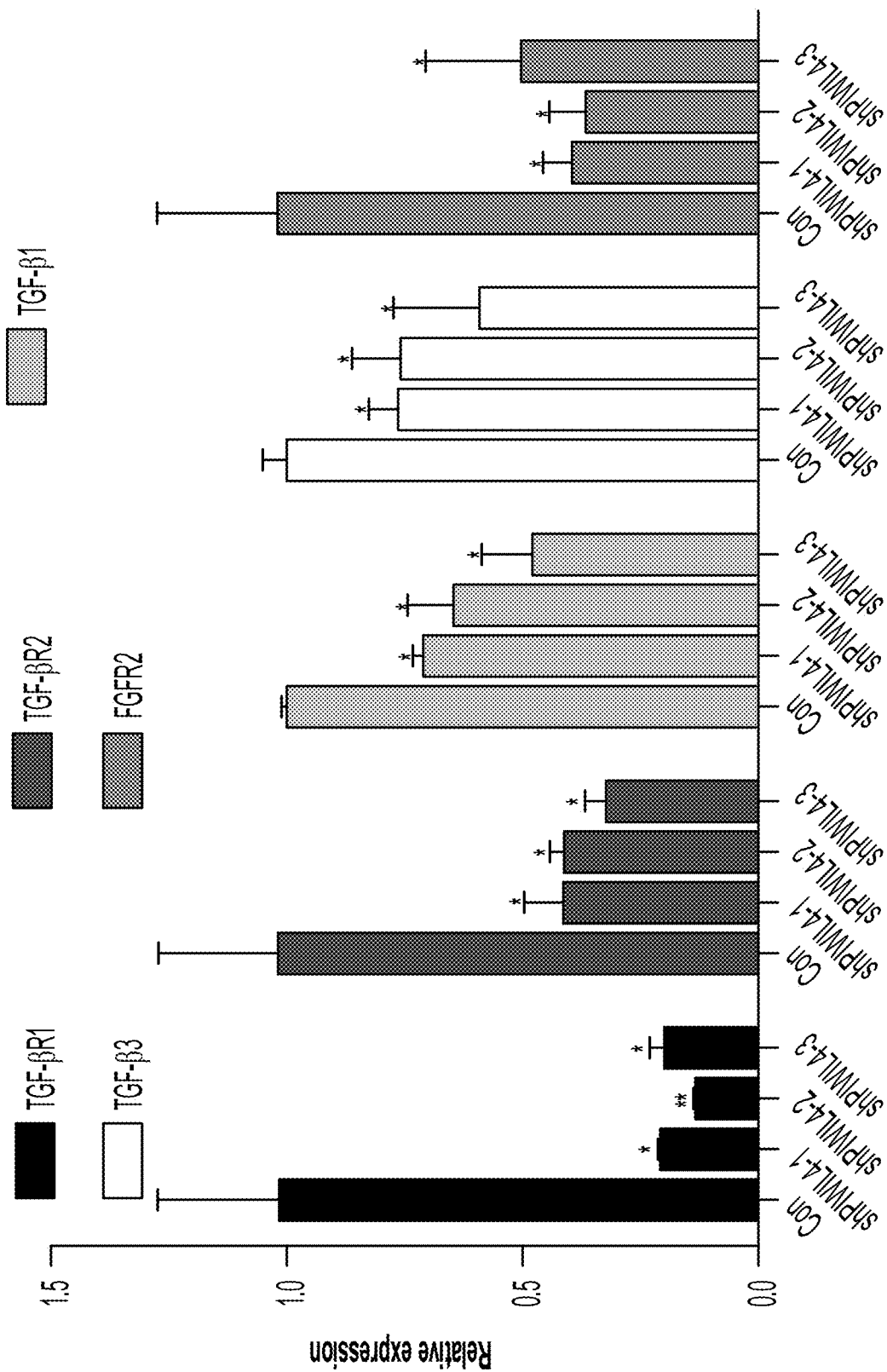
FIG. 5F depicts a graph showing the mRNA expression of TGFβR1, TGFβR2, FGFR2, TGFβ1, and TGFβ3 measured by quantitative RT-PCR. All of the five genes were down-regulated in all three different PIWIL4 knockdown cell samples.
Figure 5G:
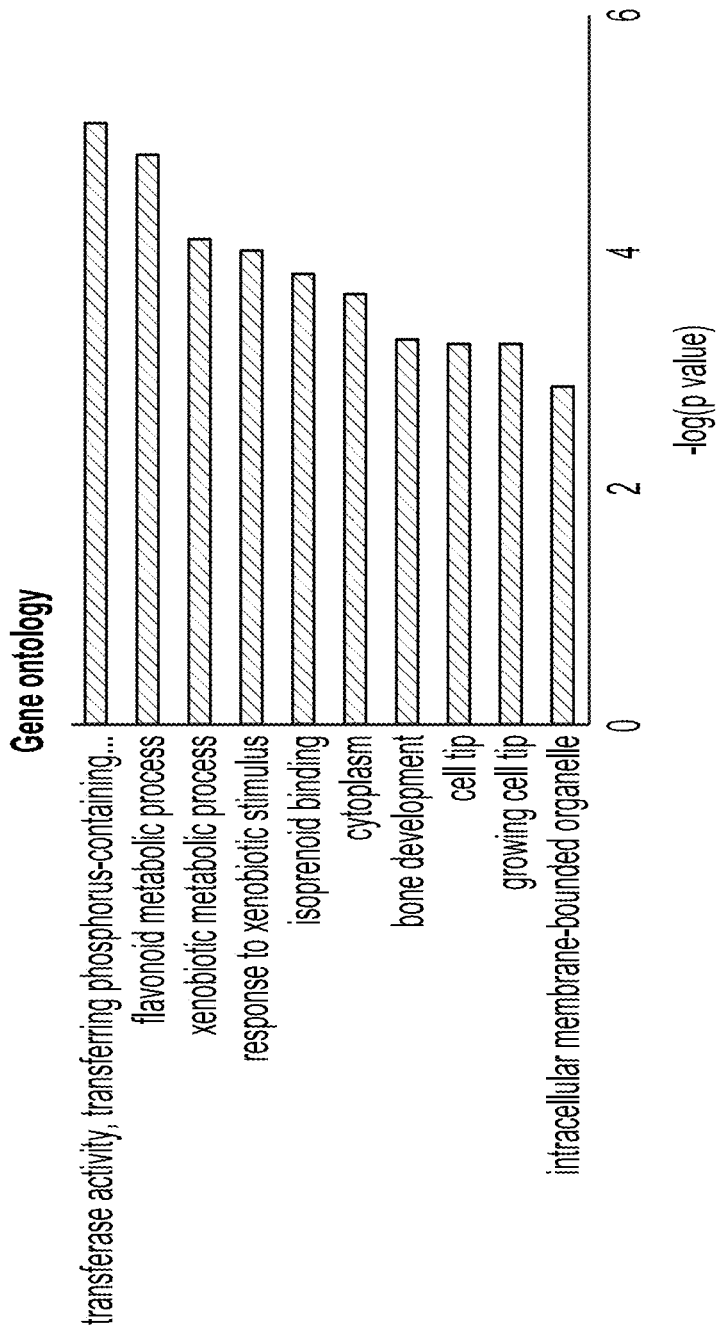
FIG. 5G depicts a graph showing the Gene Ontology analysis of 1288 proteins specifically presented in normal cancer cells and 207 proteins specifically presented in PIWIL4 knockdown cells (totally 1495 proteins), which showed that the most enriched gene ontology term was transferase activity and transferring phosphorus-containing groups.
Figure 10A:
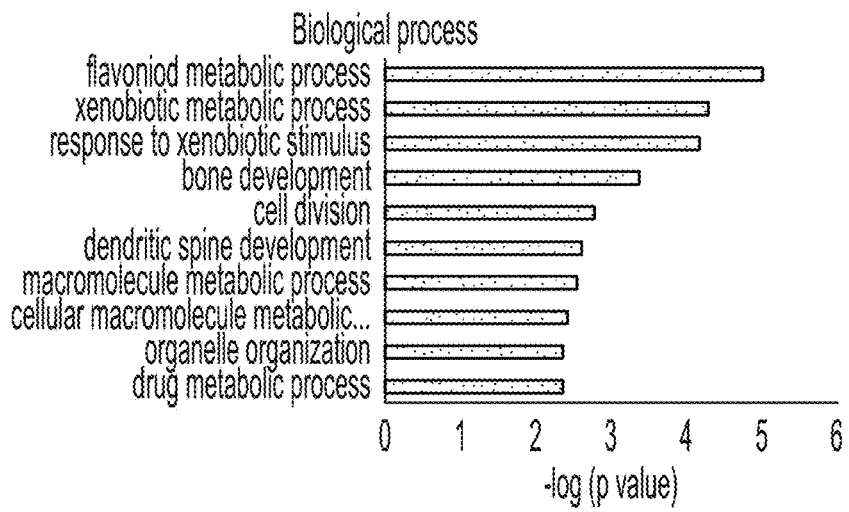
FIG. 10A depicts a graph that shows the most significantly enriched biological processes as ranked by their p values, which revealed that cell division was also an enriched biological process.
Figure 10B:
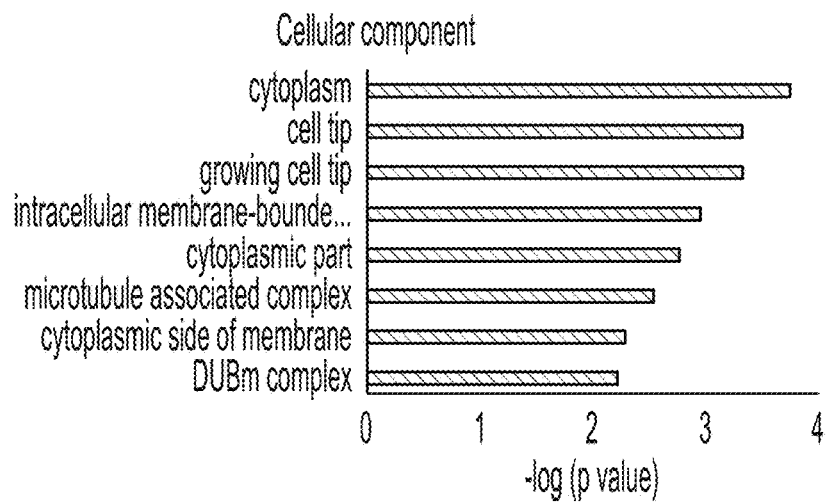
FIG. 10B depicts a graph that shows the most significantly enriched cellular components as ranked by their p values, which revealed that cell division was also an enriched biological process.
Figure 10C:
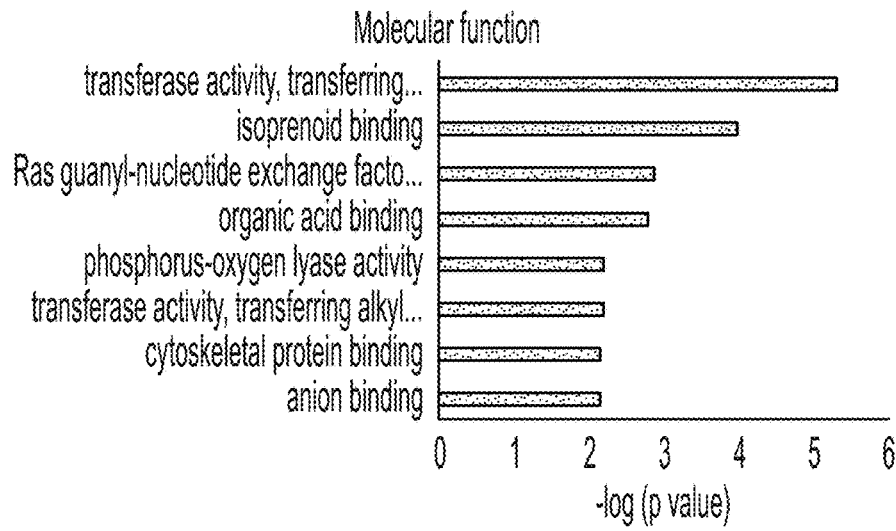
FIG. 10C depicts a graph that shows the most significantly enriched molecular functions as ranked by their p values, which revealed that cell division was also an enriched biological process.

To validate the down-regulation of the above described proteins, the mRNA expression of TGFβR1, TGFβR2, FGFR2, TGFβ1, and TGFβ3 was measured by quantitative RT-PCR. Indeed, all of the five genes were down-regulated in all three different PIWIL4 knockdown cell samples (FIG. 5F). The down-regulation of the TGF pathway components was further supported by gene ontology analysis of 1288 proteins specifically present in normal cancer cells and 207 proteins specifically present in PIWIL4 knockdown cells (totally 1495 proteins), which showed that the most enriched gene ontology term was transferase activity and transferring phosphorus-containing groups (FIG. 5G), which is frequently involved in protein activity, including the TGF-β, FGF, and MAPK-ERK signaling pathways. FIGS. 10A-10C shows the most significantly enriched biological processes, cellular components, and molecular functions as ranked by their p values, which revealed that cell division was also an enriched biological process (the full list is presented in Table 4 below). Taken together, PIWIL4 promoted MDAMB-231 epithelial-to-mesenchymal transition, migratory ability, and proliferation and inhibited apoptosis partially by activating the TGF-β and FGF signaling pathways.

TABLE 4

GO analysis of 1495 proteins differentially expressed between the control and three shPIWIL4 samples

| Select | gene ontology term | category, level | set size | candidates contained | candidates contained (%) | p-value | q-value |
|---|---|---|---|---|---|---|---|
| GO:0016772 | transferase activity, transferring phosphorus-containing groups | MF 3 | 954 | 110 | 11.50% | 4.84E-06 | 0.000707 |
| GO:2001106 | regulation of Rho guanyl-nucleotide exchange factor activity | BP 3 | 2 | 2 | 100.00% | 0.00571 | 0.231 |
| GO:0009812 | flavonoid metabolic process | BP 3 | 31 | 11 | 35.50% | 9.10E-06 | 0.00442 |
| GO:0060996 | dendritic spine development | BP 3 | 55 | 11 | 20.00% | 0.0024 | 0.194 |
| GO:0019840 | isoprenoid binding | MF 3 | 39 | 11 | 28.20% | 0.000103 | 0.00749 |
| GO:0035838 | growing cell tip | CC 3 | 3 | 3 | 100.00% | 0.000431 | 0.0236 |
| GO:0017144 | drug metabolic process | BP 3 | 51 | 10 | 19.60% | 0.00433 | 0.21 |
| GO:0071819 | DUBm complex | CC 3 | 2 | 2 | 100.00% | 0.00571 | 0.117 |
| GO:0051286 | cell tip | CC 3 | 6 | 4 | 66.70% | 0.000431 | 0.0236 |
| GO:0005875 | microtubule associated complex | CC 3 | 144 | 21 | 14.60% | 0.00273 | 0.0746 |
| GO:0005088 | Ras guanyl-nucleotide exchange factor activity | MF 3 | 127 | 20 | 15.70% | 0.00134 | 0.0552 |
| GO:0043177 | organic acid binding | MF 3 | 194 | 27 | 13.90% | 0.00151 | 0.0552 |
| GO:0098562 | cytoplasmic side of membrane | CC 3 | 171 | 23 | 13.50% | 0.00498 | 0.117 |
| GO:0055017 | cardiac muscle tissue growth | BP 3 | 57 | 10 | 17.50% | 0.0097 | 0.308 |
| GO:0006805 | xenobiotic metabolic process | BP 3 | 175 | 29 | 16.60% | 5.00E-05 | 0.0102 |
| GO:0005737 | cytoplasm | CC 3 | 10429 | 852 | 8.20% | 0.00016 | 0.0236 |
| GO:0009410 | response to xenobiotic stimulus | BP 3 | 186 | 30 | 16.10% | 6.28E-05 | 0.0102 |
| GO:0060348 | bone development | BP 3 | 178 | 27 | 15.20% | 0.000397 | 0.0482 |
| GO:0035265 | organ growth | BP 3 | 142 | 20 | 14.10% | 0.00507 | 0.224 |
| GO:0051301 | cell division | BP 3 | 627 | 68 | 10.80% | 0.00162 | 0.158 |
| GO:0044444 | cytoplasmic part | CC 3 | 7800 | 642 | 8.20% | 0.0016 | 0.0523 |
| GO:0007017 | microtubule-based process | BP 3 | 592 | 61 | 10.30% | 0.00831 | 0.308 |
| GO:0006996 | organelle organization | BP 3 | 3521 | 304 | 8.60% | 0.00421 | 0.21 |
| GO:0043231 | intracellular membrane-bounded organelle | CC 3 | 10643 | 859 | 8.10% | 0.00103 | 0.0421 |
| GO:0016849 | phosphorus-oxygen lyase activity | MF 3 | 23 | 6 | 26.10% | 0.00608 | 0.124 |
| GO:0016765 | transferase activity, transferring alkyl or aryl (other than methyl) groups | MF 3 | 62 | 11 | 17.70% | 0.00628 | 0.124 |
| GO:0043168 | anion binding | MF 3 | 2660 | 233 | 8.80% | 0.00678 | 0.124 |
| GO:0008092 | cytoskeletal protein binding | MF 3 | 804 | 80 | 10.00% | 0.00678 | 0.124 |
| GO:0006793 | phosphorus metabolic process | BP 3 | 2966 | 256 | 8.60% | 0.00953 | 0.308 |

TABLE 4-continued

GO analysis of 1495 proteins differentially expressed between the control and three shPIWIL4 samples

| Select | gene ontology term | category, level | set size | candidates contained | candidates contained (%) | p-value | q-value |
|---|---|---|---|---|---|---|---|
| GO:0043170 | macromolecule metabolic process | BP 3 | 8948 | 726 | 8.10% | 0.00282 | 0.196 |
| GO:0044260 | cellular macromolecule metabolic process | BP 3 | 8270 | 673 | 8.10% | 0.00378 | 0.21 |

Figure 11B:
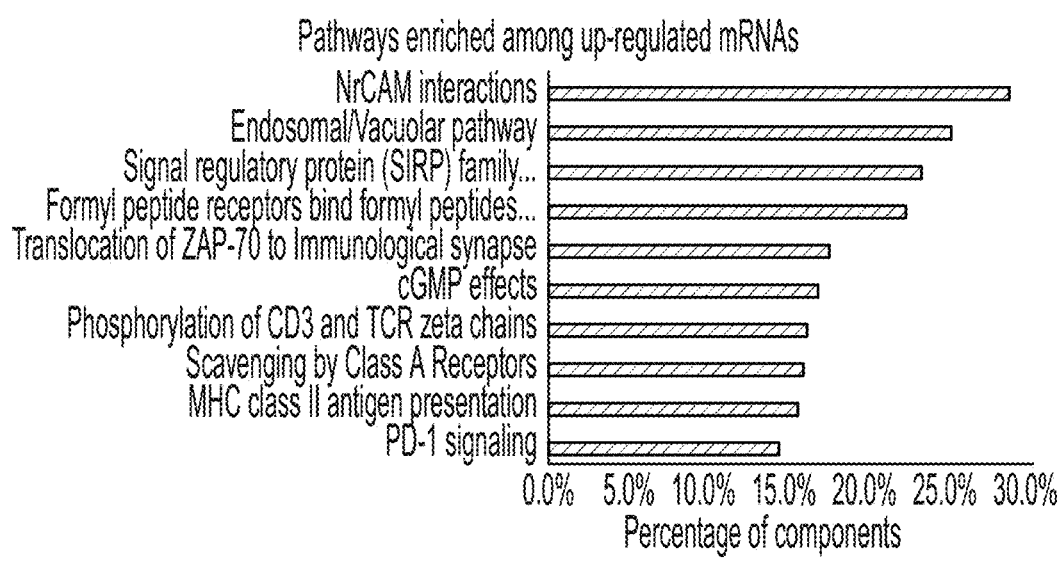
FIG. 11B depicts a graph showing the pathway enrichment analysis results of the pathways enriched among up-regulated mRNAs.
Figure 11C:
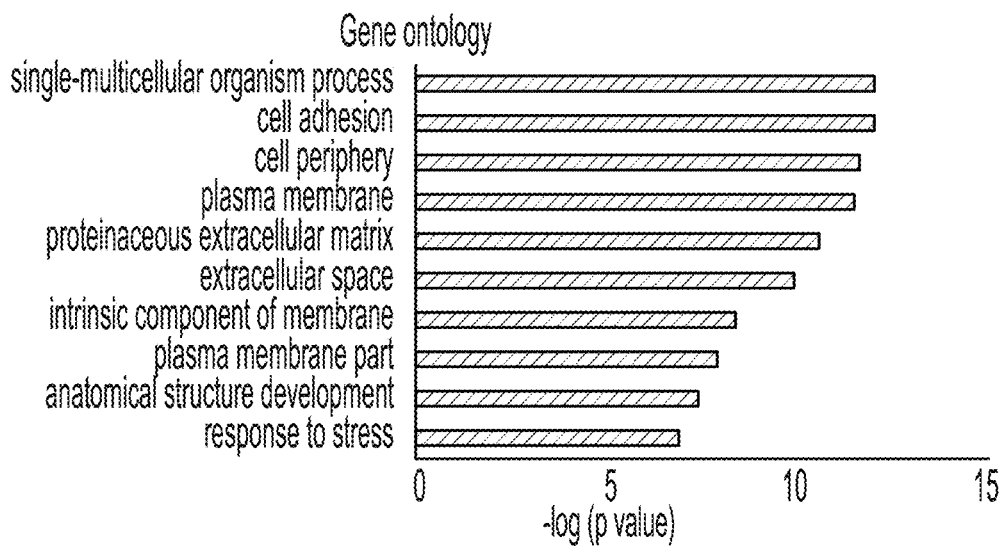
FIG. 11C depicts a graph showing the pathway enrichment analysis results of the gene ontology.
Figure 11D:
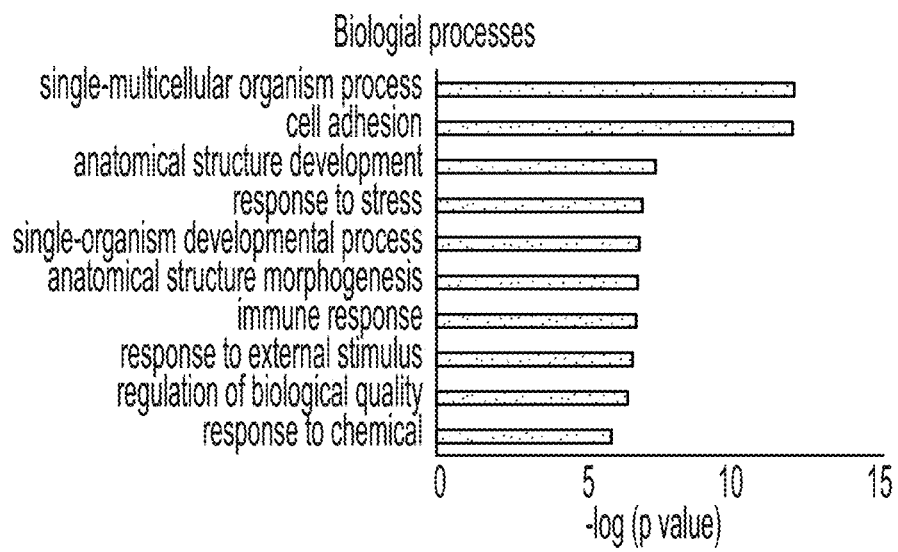
FIG. 11D depicts a graph showing the pathway enrichment analysis results of the biological processes.
Figure 11E:
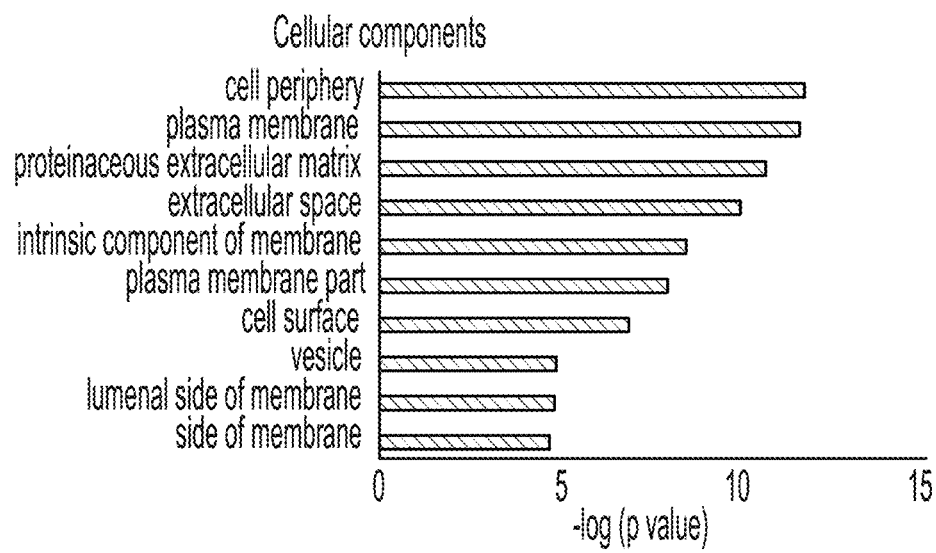
FIG. 11E depicts a graph showing the pathway enrichment analysis results of the cellular components.
Figure 11F:
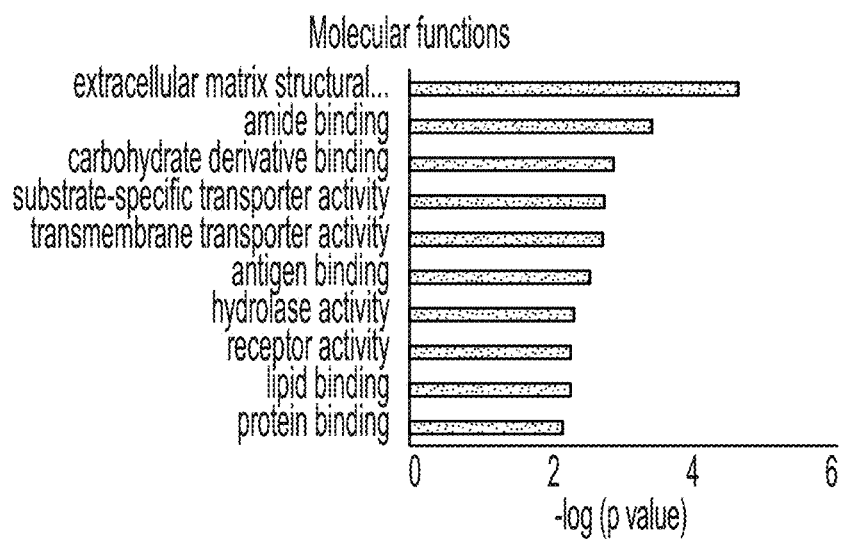
FIG. 11F depicts a graph showing the pathway enrichment analysis results of the molecular functions.

Example 5: PIWIL4 Repressed the Expression of MHC II Genes in MDAMB-231 Cells Tumorigenesis and development is a complex process involving not only cell proliferation but also tumor immune escape pathways. Combined gene ontology analysis of the 400 up-regulated mRNAs and 332 down-regulated mRNAs (total of 732 genes) revealed that genes related to tumor immune escape were enriched among the 62 gene ontology terms (Table 5, below). Especially the top 10 gene ontology terms were more related to cell adhesion, cell periphery, extracellular matrix structural constituents, single-multicellular organism cellular processes, and anatomical structure development (FIG. 11C). FIGS. 11D-11F show the top 10 most significant biological processes, cellular components, and molecular functions, respectively. Immunoresponse and cell adhesion were enriched among biological process, and the enriched molecules are mostly localized to the cell periphery, extracellular space, and cell surface, performing their roles of extracellular matrix structural constituent, antigen binding, and receptor binding. Moreover, cell proliferation and death were also in the enriched terms.

TABLE 5

Significantly enriched GO terms of mRNA significantly changed in shPIWIL4 or the control

| Gene ontology term | gene ontology term | Category, level | Set size | Candidates contained | p-value | q-value |
|---|---|---|---|---|---|---|
| GO:0044707 | single-multicellular organism process | BP2 | 6658 | 276 (4.2%) | 9.49E−13 | 4.71E−11 |
| GO:0007155 | cell adhesion | BP2 | 1421 | 91 (6.4%) | 1.08E−12 | 4.71E−11 |
| GO:0071944 | cell periphery | CC 2 | 4967 | 220 (4.4%) | 2.33E−12 | 1.17E−10 |
| GO:0005886 | plasma membrane | CC 2 | 4864 | 216 (4.5%) | 3.34E−12 | 1.17E−10 |
| GO:0005578 | proteinaceous extracellular matrix | CC 2 | 356 | 37 (10.5%) | 2.69E−11 | 6.27E−10 |
| GO:0005615 | extracellular space | CC 2 | 1338 | 82 (6.2%) | 1.27E−10 | 2.21E−09 |
| GO:0031224 | intrinsic component of membrane | CC 2 | 5523 | 225 (4.1%) | 4.05E−09 | 5.66E−08 |
| GO:0044459 | plasma membrane part | CC 2 | 2528 | 122 (4.8%) | 1.23E−08 | 1.43E−07 |
| GO:0048856 | anatomical structure development | BP2 | 5056 | 206 (4.1%) | 4.37E−08 | 1.27E−06 |
| GO:0006950 | response to stress | BP2 | 3940 | 167 (4.3%) | 1.24E−07 | 2.39E−06 |
| GO:0009986 | cell surface | CC 2 | 728 | 48 (6.6%) | 1.57E−07 | 1.57E−06 |
| GO:0044767 | single-organism developmental process | BP2 | 5607 | 221 (4.0%) | 1.59E−07 | 2.39E−06 |
| GO:0009653 | anatomical structure morphogenesis | BP2 | 2616 | 121 (4.6%) | 1.76E−07 | 2.39E−06 |
| GO:0006955 | immune response | BP2 | 1569 | 82 (5.3%) | 1.92E−07 | 2.39E−06 |
| GO:0009605 | response to external stimulus | BP2 | 2412 | 113 (4.7%) | 2.47E−07 | 2.69E−06 |
| GO:0065008 | regulation of biological quality | BP2 | 3431 | 148 (4.3%) | 3.62E−07 | 3.50E−06 |
| GO:0042221 | response to chemical | BP2 | 4132 | 169 (4.1%) | 1.31E−06 | 1.14E−05 |
| GO:0048870 | cell motility | BP2 | 1256 | 67 (5.3%) | 1.68E−06 | 1.21E−05 |
| GO:0051674 | localization of cell | BP2 | 1256 | 67 (5.3%) | 1.68E−06 | 1.21E−05 |
| GO:0050900 | leukocyte migration | BP2 | 351 | 28 (8.0%) | 1.93E−06 | 1.29E−05 |
| GO:0048646 | anatomical structure formation involved in morphogenesis | BP2 | 1156 | 62 (5.4%) | 3.66E−06 | 2.28E−05 |
| GO:0009719 | response to endogenous stimulus | BP2 | 1573 | 77 (4.9%) | 6.53E−06 | 3.79E−05 |

TABLE 5-continued

Significantly enriched GO terms of mRNA significantly changed in shPIWIL4 or the control

| Gene ontology term | gene ontology term | Category, level | Set size | Candidates contained | p-value | q-value |
|---|---|---|---|---|---|---|
| GO:0042330 | taxis | BP2 | 704 | 42 (6.0%) | 1.25E−05 | 6.59E−05 |
| GO:0044700 | single organism signaling | BP2 | 6125 | 227 (3.7%) | 1.29E−05 | 6.59E−05 |
| GO:0031982 | vesicle | CC 2 | 3633 | 147 (4.1%) | 1.43E−05 | 0.000125 |
| GO:0008283 | cell proliferation | BP2 | 1918 | 88 (4.6%) | 1.56E−05 | 7.55E−05 |
| GO:0098576 | lumenal side of membrane | CC 2 | 30 | 7 (24.1%) | 1.66E−05 | 0.000129 |
| GO:0098552 | side of membrane | CC 2 | 423 | 29 (6.9%) | 2.19E−05 | 0.000153 |
| GO:0005201 | extracellular matrix structural constituent | MF 2 | 67 | 10 (14.9%) | 2.52E−05 | 0.00106 |
| GO:0098602 | single organism cell adhesion | BP2 | 752 | 43 (5.7%) | 2.56E−05 | 0.000117 |
| GO:0051234 | establishment of localization | BP2 | 4636 | 175 (3.8%) | 9.66E−05 | 0.00042 |
| GO:1902578 | single-organism localization | BP2 | 4068 | 155 (3.8%) | 0.000197 | 0.000816 |
| GO:0048589 | developmental growth | BP2 | 551 | 32 (5.8%) | 0.000226 | 0.000895 |
| GO:0043197 | dendritic spine | CC 2 | 104 | 11 (10.6%) | 2.50E−04 | 0.00159 |
| GO:0007626 | locomotory behavior | BP2 | 201 | 16 (8.0%) | 0.000303 | 0.00115 |
| GO:0033218 | amide binding | MF 2 | 251 | 18 (7.3%) | 4.10E−04 | 0.00861 |
| GO:0045321 | leukocyte activation | BP2 | 701 | 37 (5.3%) | 0.000437 | 0.00158 |
| GO:0097458 | neuron part | CC 2 | 1179 | 55 (4.7%) | 5.04E−04 | 0.00294 |
| GO:0005583 | fibrillar collagen trimer | CC 2 | 14 | 4 (28.6%) | 5.93E−04 | 0.00319 |
| GO:0043230 | extracellular organelle | CC 2 | 2792 | 110 (4.0%) | 6.52E−04 | 0.00326 |
| GO:0044763 | single-organism cellular process | BP2 | 12248 | 395 (3.2%) | 0.000819 | 0.00285 |
| GO:0098589 | membrane region | CC 2 | 1086 | 50 (4.6%) | 1.18E−03 | 0.00549 |
| GO:0097367 | carbohydrate derivative binding | MF 2 | 2222 | 89 (4.0%) | 1.40E−03 | 0.0164 |
| GO:0098794 | postsynapse | CC 2 | 351 | 21 (6.0%) | 1.70E−03 | 0.00745 |
| GO:0022892 | substrate-specific transporter activity | MF 2 | 1055 | 48 (4.6%) | 1.87E−03 | 0.0164 |
| GO:0022857 | transmembrane transporter activity | MF 2 | 975 | 45 (4.6%) | 1.95E−03 | 0.0164 |
| GO:0098805 | whole membrane | CC 2 | 1916 | 78 (4.1%) | 1.96E−03 | 0.00808 |
| GO:0051716 | cellular response to stimulus | BP2 | 6944 | 237 (3.4%) | 0.00208 | 0.00696 |
| GO:0044708 | single-organism behavior | BP2 | 409 | 23 (5.6%) | 0.00244 | 0.00785 |
| GO:0014069 | postsynaptic density | CC 2 | 183 | 13 (7.1%) | 2.98E−03 | 0.0116 |
| GO:0003823 | antigen binding | MF 2 | 103 | 9 (8.9%) | 2.99E−03 | 0.021 |
| GO:0016787 | hydrolase activity | MF 2 | 2477 | 94 (3.8%) | 0.00498 | 0.0264 |
| GO:0098644 | complex of collagen trimers | CC 2 | 24 | 4 (16.7%) | 4.98E−03 | 0.0184 |
| GO:0002253 | activation of immune response | BP2 | 539 | 27 (5.0%) | 0.00521 | 0.0162 |
| GO:0004872 | receptor activity | MF 2 | 1583 | 64 (4.1%) | 0.00548 | 0.0264 |
| GO:0008289 | lipid binding | MF 2 | 647 | 31 (4.8%) | 0.00565 | 0.0264 |
| GO:0016265 | death | BP2 | 1972 | 77 (3.9%) | 0.00585 | 0.0171 |
| GO:0065009 | regulation of molecular function | BP2 | 2699 | 101 (3.8%) | 0.00588 | 0.0171 |
| GO:0042995 | cell projection | CC 2 | 1769 | 70 (4.0%) | 0.00669 | 0.0234 |
| GO:0005515 | protein binding | MF 2 | 10524 | 338 (3.2%) | 0.00733 | 0.0308 |
| GO:0005604 | basement membrane | CC 2 | 97 | 8 (8.3%) | 0.00748 | 0.024 |
| GO:0045177 | apical part of cell | CC 2 | 348 | 19 (5.5%) | 0.00754 | 0.024 |

Pathway enrichment analysis of the 400 up-regulated genes revealed that PIWIL4 represses the expression of MHC class II mRNAs, including HLA-DRα, HLA-DPα1, HLA-DOα, HLA-DPβ1, cathepsin S, cathepsin E, dynamin 1, and CD74. This might lead to the upregulation of some immune responses involved in the neuronal cell adhesion molecule, the signal regulatory protein family, and the cGMP pathway, as evident in FIG. 11B (a full list is presented in Table 6). These observations were consistent with the enrichment of translation-related mechanisms among the 207 most up-regulated proteins under the PIWIL4 deficiency condition (FIG. 5D, a full list is presented in Table 7). These results implied that PIWIL4 might repress MHC class II, which might help cancer cells avoid immune recognition (Meazza, R., et al (2003) Eur. J. Immunol. 33, 1183-1192, and Mottok, A., et al. (2015) Cell Rep. 13, 1418-1431).

TABLE 6

Pathway analysis of 400 mRNAs significantly upregulated in shPIWIL4 cells.

| Pathway name | set size | Candidates contained | Candidates contained (%) | p-value | q-value | pathway source |
|---|---|---|---|---|---|---|
| NrCAM interactions | 7 | 2 | 28.60% | 0.00569 | 0.0536 | Reactome |
| Endosomal/Vacuolar pathway | 12 | 3 | 25.00% | 0.000945 | 0.0136 | Reactome |
| antigen processing and presentation | 12 | 3 | 25.00% | 0.000945 | 0.0136 | BioCarta |
| Signal regulatory protein (SIRP) family interactions | 13 | 3 | 23.10% | 0.00121 | 0.0161 | Reactome |
| Formyl peptide receptors bind formyl peptides and many other ligands | 9 | 2 | 22.20% | 0.00954 | 0.0754 | Reactome |
| Allograft rejection - *Homo sapiens* (human) | 37 | 7 | 18.90% | 2.43E−06 | 0.000238 | KEGG |
| Translocation of ZAP-70 to Immunological synapse | 24 | 4 | 17.40% | 0.000553 | 0.01 | Reactome |
| Graft-versus-host disease - *Homo sapiens* (human) | 41 | 7 | 17.10% | 5.01E−06 | 0.000403 | KEGG |
| Asthma - *Homo sapiens* (human) | 30 | 5 | 16.70% | 0.000135 | 0.0044 | KEGG |
| cGMP effects | 18 | 3 | 16.70% | 0.00325 | 0.038 | Reactome |
| *Staphylococcus aureus* infection - *Homo sapiens* (human) | 55 | 9 | 16.40% | 3.13E−07 | 0.000123 | KEGG |
| Type I diabetes mellitus - *Homo sapiens* (human) | 43 | 7 | 16.30% | 6.97E−06 | 0.000427 | KEGG |
| Phosphorylation of CD3 and TCR zeta chains | 26 | 4 | 16.00% | 0.000769 | 0.0126 | Reactome |
| Scavenging by Class A Receptors | 19 | 3 | 15.80% | 0.00382 | 0.0415 | Reactome |
| MHC class II antigen presentation | 59 | 9 | 15.50% | 5.02E−07 | 0.000123 | Reactome |
| PD-1 signaling | 29 | 4 | 14.30% | 0.0012 | 0.0161 | Reactome |
| Autoimmune thyroid disease - *Homo sapiens* (human) | 52 | 7 | 13.50% | 2.55E−05 | 0.00125 | KEGG |
| Generation of second messenger molecules | 38 | 5 | 13.50% | 0.000374 | 0.00834 | Reactome |
| Beta2 integrin cell surface interactions | 30 | 4 | 13.30% | 0.00156 | 0.0196 | PID |
| O-glycosylation of TSR domain-containing proteins | 39 | 5 | 12.80% | 0.000481 | 0.00907 | Reactome |
| Inflammatory Response Pathway | 32 | 4 | 12.50% | 0.00199 | 0.0244 | Wikipathways |
| IL1 and megakaryotyces in obesity | 24 | 3 | 12.50% | 0.00749 | 0.0655 | Wikipathways |
| Beta1 integrin cell surface interactions | 66 | 8 | 12.10% | 1.47E−05 | 0.0008 | PID |
| Viral myocarditis - *Homo sapiens* (human) | 58 | 7 | 12.10% | 5.25E−05 | 0.00214 | KEGG |
| Nitric oxide stimulates guanylate cyclase | 25 | 3 | 12.00% | 0.00841 | 0.071 | Reactome |
| Antigen processing and presentation - *Homo sapiens* (human) | 77 | 9 | 11.70% | 5.76E−06 | 0.000403 | KEGG |
| Beta3 integrin cell surface interactions | 43 | 5 | 11.60% | 0.000762 | 0.0126 | PID |
| Endogenous TLR signaling | 26 | 3 | 11.50% | 0.00938 | 0.0754 | PID |
| Intestinal immune network for IgA production - *Homo sapiens* (human) | 47 | 5 | 10.60% | 0.00115 | 0.0161 | KEGG |

TABLE 6-continued

Pathway analysis of 400 mRNAs significantly upregulated in shPIWIL4 cells.

| Pathway name | set size | Candidates contained | Candidates contained (%) | p-value | q-value | pathway source |
|---|---|---|---|---|---|---|
| Allograft Rejection | 80 | 8 | 10.00% | 6.06E−05 | 0.00228 | Wikipathways |
| Binding and Uptake of Ligands by Scavenger Receptors | 40 | 4 | 10.00% | 0.00456 | 0.0456 | Reactome |
| CD4 T cell receptor signaling-ERK cascade | 41 | 4 | 10.00% | 0.00456 | 0.0456 | INOH |
| Leishmaniasis - *Homo sapiens* (human) | 72 | 7 | 9.70% | 0.000211 | 0.00552 | KEGG |
| Peptide GPCRs | 73 | 7 | 9.60% | 0.00023 | 0.00552 | Wikipathways |
| Cell adhesion molecules (CAMs) - *Homo sapiens* (human) | 142 | 13 | 9.20% | 8.26E−07 | 0.000135 | KEGG |
| Inflammatory bowel disease (IBD) - *Homo sapiens* (human) | 65 | 6 | 9.20% | 0.000794 | 0.0126 | KEGG |
| activation of csk by camp-dependent protein kinase inhibits signaling through the t cell receptor | 45 | 4 | 8.90% | 0.00696 | 0.063 | BioCarta |
| Phagosome - *Homo sapiens* (human) | 153 | 13 | 8.50% | 1.93E−06 | 0.000236 | KEGG |
| Complement and Coagulation Cascades | 60 | 5 | 8.30% | 0.00343 | 0.039 | Wikipathways |
| il-2 receptor beta chain in t cell activation | 48 | 4 | 8.30% | 0.00874 | 0.0726 | BioCarta |
| Downstream TCR signaling | 50 | 4 | 8.20% | 0.00939 | 0.0754 | Reactome |
| Rheumatoid arthritis - *Homo sapiens* (human) | 89 | 7 | 7.90% | 0.000774 | 0.0126 | KEGG |
| Human Complement System | 90 | 7 | 7.80% | 0.000827 | 0.0127 | Wikipathways |
| Collagen biosynthesis and modifying enzymes | 64 | 5 | 7.80% | 0.00453 | 0.0456 | Reactome |
| IL12-mediated signaling events | 65 | 5 | 7.80% | 0.00453 | 0.0456 | PID |
| Toxoplasmosis - *Homo sapiens* (human) | 118 | 9 | 7.60% | 0.000176 | 0.00539 | KEGG |
| O-linked glycosylation | 105 | 8 | 7.60% | 0.000406 | 0.0084 | Reactome |
| Platelet homeostasis | 79 | 6 | 7.60% | 0.0022 | 0.0263 | Reactome |
| TCR signaling | 68 | 5 | 7.50% | 0.00551 | 0.0529 | Reactome |
| L1CAM interactions | 100 | 7 | 7.10% | 0.00145 | 0.0187 | Reactome |
| Collagen formation | 87 | 6 | 6.90% | 0.00357 | 0.0398 | Reactome |
| Costimulation by the CD28 family | 75 | 5 | 6.80% | 0.0079 | 0.0679 | Reactome |
| Peptide ligand-binding receptors | 199 | 13 | 6.60% | 3.03E−05 | 0.00135 | Reactome |
| Herpes simplex infection - *Homo sapiens* (human) | 184 | 12 | 6.50% | 6.91E−05 | 0.00242 | KEGG |
| Tuberculosis - *Homo sapiens* (human) | 177 | 11 | 6.20% | 0.000212 | 0.00552 | KEGG |
| Cell-Cell communication | 128 | 7 | 5.50% | 0.00612 | 0.0565 | Reactome |
| G alpha (i) signalling events | 243 | 13 | 5.40% | 0.000235 | 0.00552 | Reactome |
| HTLV-I infection - *Homo sapiens* (human) | 259 | 13 | 5.00% | 0.00047 | 0.00907 | KEGG |
| Class A/1 (Rhodopsin-like receptors) | 326 | 15 | 4.60% | 0.000411 | 0.0084 | Reactome |
| Influenza A - *Homo sapiens* (human) | 175 | 8 | 4.60% | 0.00994 | 0.0773 | KEGG |

TABLE 6-continued

Pathway analysis of 400 mRNAs significantly upregulated in shPIWIL4 cells.

| Pathway name | set size | Candidates contained | Candidates contained (%) | p-value | q-value | pathway source |
|---|---|---|---|---|---|---|
| Epstein-Barr virus infection - *Homo sapiens* (human) | 201 | 9 | 4.50% | 0.00707 | 0.063 | KEGG |
| GPCR ligand binding | 454 | 19 | 4.20% | 0.000237 | 0.00552 | Reactome |
| Extracellular matrix organization | 264 | 11 | 4.20% | 0.00523 | 0.0513 | Reactome |

TABLE 7

Pathway analysis of 207 proteins detectable only in shPIWI4 cells

| Pathway name | set size | candidates contained | % of components | p-value | q-value | pathway source |
|---|---|---|---|---|---|---|
| Ribosomal scanning and start codon recognition | 63 | 7 | 12.30% | 5.27E−06 | 0.000311 | Reactome |
| Translation initiation complex formation | 63 | 7 | 12.30% | 5.27E−06 | 0.000311 | Reactome |
| Activation of the mRNA upon binding of the cap-binding complex and eIFs, and subsequent binding to 43S | 64 | 7 | 12.10% | 5.93E−06 | 0.000311 | Reactome |
| Ribosome biogenesis in eukaryotes - *Homo sapiens* (human) | 87 | 7 | 9.10% | 3.92E−05 | 0.00126 | KEGG |
| L13a-mediated translational silencing of Ceruloplasmin expression | 117 | 9 | 8.40% | 5.70E−06 | 0.000311 | Reactome |
| 3,-UTR-mediated translational regulation | 117 | 9 | 8.40% | 5.70E−06 | 0.000311 | Reactome |
| GTP hydrolysis and joining of the 60S ribosomal subunit | 118 | 9 | 8.30% | 6.15E−06 | 0.000311 | Reactome |
| Cap-dependent Translation Initiation | 125 | 9 | 7.80% | 1.03E−05 | 0.000405 | Reactome |
| Eukaryotic Translation Initiation | 125 | 9 | 7.80% | 1.03E−05 | 0.000405 | Reactome |
| Ribosome - *Homo sapiens* (human) | 137 | 10 | 7.50% | 4.68E−06 | 0.000311 | KEGG |
| RNA transport - *Homo sapiens* (human) | 172 | 10 | 6.00% | 3.29E−05 | 0.00116 | KEGG |
| Translation | 161 | 9 | 6.00% | 8.50E−05 | 0.00251 | Reactome |
| Formation of a pool of free 40S subunits | 107 | 7 | 7.20% | 0.000171 | 0.00466 | Reactome |
| HIV Life Cycle | 142 | 8 | 5.70% | 0.000297 | 0.00738 | Reactome |
| Translation Factors | 50 | 5 | 10.00% | 0.000333 | 0.00738 | Wikipathways |
| Formation of the ternary complex, and subsequently, the 43S complex | 56 | 5 | 10.00% | 0.000333 | 0.00738 | Reactome |
| Mitochondrial translation elongation | 84 | 6 | 7.10% | 0.000534 | 0.0111 | Reactome |
| Mitochondrial translation | 90 | 6 | 6.70% | 0.00077 | 0.0151 | Reactome |
| Nonsense Mediated Decay (NMD) enhanced | 111 | 6 | 5.90% | 0.00148 | 0.0261 | Reactome |

TABLE 7-continued

Pathway analysis of 207 proteins detectable only in shPIWI4 cells

| Pathway name | set size | candidates contained | % of components | p-value | q-value | pathway source |
|---|---|---|---|---|---|---|
| by the Exon Junction Complex (EJC) | | | | | | |
| Nonsense-Mediated Decay (NMD) | 111 | 6 | 5.90% | 0.00148 | 0.0261 | Reactome |
| HIV Infection | 182 | 8 | 4.40% | 0.00155 | 0.0261 | Reactome |
| Clearance of Nuclear Envelope Membranes from Chromatin | 7 | 2 | 28.60% | 0.00295 | 0.0474 | Reactome |
| Infectious disease | 249 | 9 | 3.60% | 0.00311 | 0.0479 | Reactome |
| Mitochondrial translation termination | 84 | 5 | 6.00% | 0.0035 | 0.0487 | Reactome |
| Mitochondrial translation initiation | 84 | 5 | 6.00% | 0.0035 | 0.0487 | Reactome |
| Influenza Life Cycle | 52 | 4 | 7.70% | 0.00357 | 0.0487 | Reactome |
| Eukaryotic Translation Termination | 95 | 5 | 5.80% | 0.00387 | 0.049 | Reactome |
| Host Interactions of HIV factors | 87 | 5 | 5.80% | 0.00387 | 0.049 | Reactome |
| Peptide chain elongation | 96 | 5 | 5.70% | 0.00407 | 0.0492 | Reactome |
| Cytoplasmic Ribosomal Proteins | 88 | 5 | 5.70% | 0.00427 | 0.0492 | Wikipathways |
| Alzheimer,s disease - *Homo sapiens* (human) | 168 | 7 | 4.20% | 0.00433 | 0.0492 | KEGG |
| Late Phase of HIV Life Cycle | 129 | 6 | 4.70% | 0.00445 | 0.0492 | Reactome |
| Nonsense Mediated Decay (NMD) independent of the Exon Junction Complex (EJC) | 100 | 5 | 5.50% | 0.00493 | 0.0503 | Reactome |
| Integration of provirus | 10 | 2 | 22.20% | 0.00497 | 0.0503 | Reactome |
| Influenza Infection | 57 | 4 | 7.00% | 0.00498 | 0.0503 | Reactome |
| Eukaryotic Translation Elongation | 101 | 5 | 5.40% | 0.00516 | 0.0508 | Reactome |
| Purine metabolism | 224 | 8 | 3.60% | 0.00591 | 0.0565 | EHMN |
| Vpr-mediated nuclear import of PICs | 31 | 3 | 9.70% | 0.00612 | 0.057 | Reactome |
| Interactions of Vpr with host cellular proteins | 34 | 3 | 8.80% | 0.00794 | 0.0721 | Reactome |
| Amyotrophic lateral sclerosis (ALS) | 35 | 3 | 8.60% | 0.00861 | 0.0743 | Wikipathways |
| Transport of Mature mRNA Derived from an Intronless Transcript | 35 | 3 | 8.60% | 0.00861 | 0.0743 | Reactome |
| Transport of Mature mRNAs Derived from Intronless Transcripts | 36 | 3 | 8.30% | 0.00931 | 0.0785 | Reactome |

Example 6: MDA-MB-231 Cells Expressed a Small Number of Piwi-Interacting RNA (piRNAs)

Figure 6A:
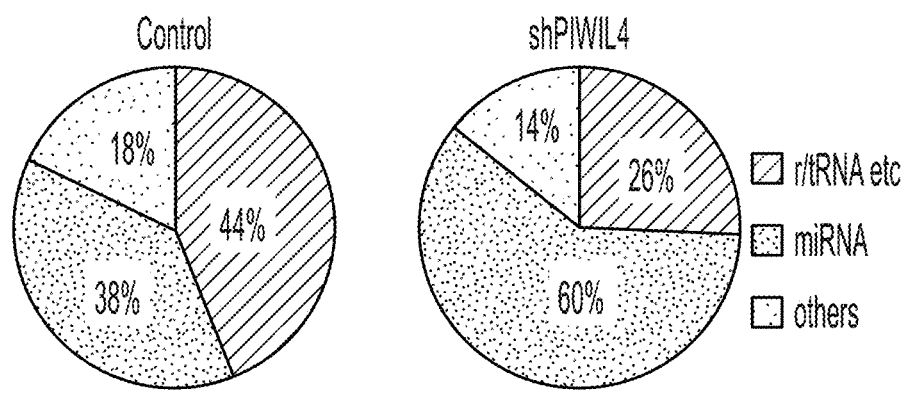
FIG. 6A depicts a diagram showing the results of small RNA (12-42 nucleotides in length) isolated from these cells with or without shPIWIL4 knockdown, followed by RT-PCR and deep sequencing. The presence of many small RNAs in MDA-MB-231 cells was observed under both conditions. These included miRNAs, other small RNAs, and fragments of rRNAs and tRNAs peaked at 19-nucleotide length.
Figure 6B:
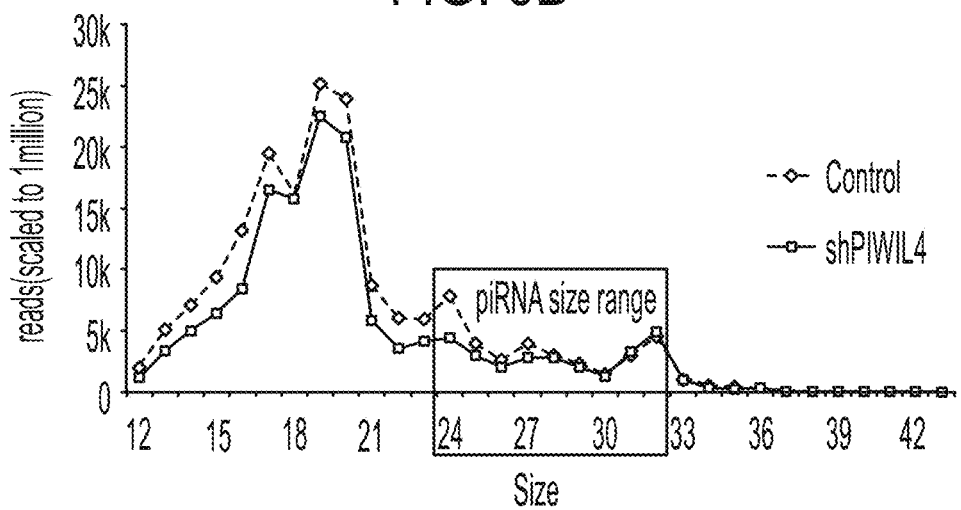
FIG. 6B depicts a graph showing the results of small RNA (12-42 nucleotides in length) isolated from these cells with or without shPIWIL4 knockdown, followed by RT-PCR and deep sequencing. The presence of many small RNAs in MDA-MB-231 cells was observed under both conditions. These included miRNAs, other small RNAs, and fragments of rRNAs and tRNAs peaked at 19-nucleotide length.

As the first step to investigate whether PIWIL4 function in MDAMB-231 cells was related to piRNA, the expression of piRNAs under normal PIWIL4 expression and PIWIL4 knockdown conditions was examined. Small RNA (12-42 nucleotides in length) was isolated from these cells with or without shPIWIL4 knockdown, followed by RT-PCR and deep sequencing. The presence of many small RNAs in MDA-MB-231 cells was observed under both conditions. These included miRNAs, other small RNAs, and fragments of rRNAs and tRNAs peaked at 19-nucleotide length (FIGS. 6A and 6B). Interestingly, under the knockdown condition, the miRNA population became significantly enriched in abundance (from 38% to 60% of the total small RNA reads, reflecting a 58% increase) at the expense of rRNA and tRNA fragments. Although this change could be due to less degradation of rRNA and tRNA in the RNA preparation from the PIWIL4 knockdown cells, this possibility is unlikely because, if so, the "other small RNA" fraction should correspondingly show a 58% increase in its abundance. However, the other small RNA fraction was decreased from 18% to 14%, reflecting a 29% decrease. Therefore, the increase in miRNA abundance mostly, if not exclusively, reflected a role of PIWIL4 in repressing miRNA expression in MDA-MB-231 cells.

Figure 6C:
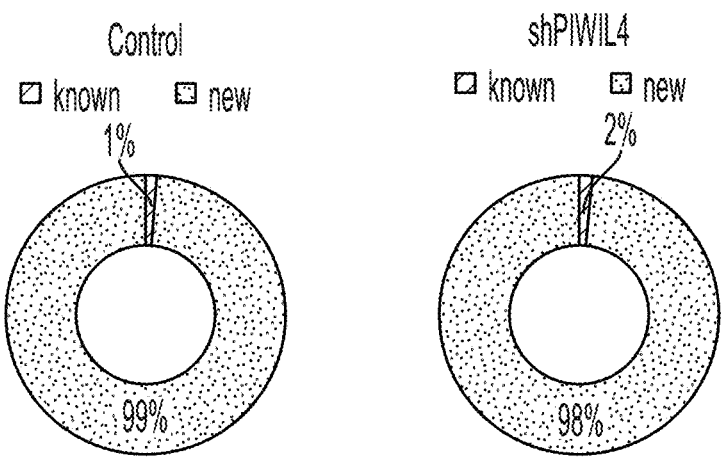
FIG. 6C depicts a graph showing results of 98,139 species of small RNAs from MDAMB-231 cells without PIWIL4 knockdown and 55,624 species from these cells with PIWIL4 knockdown. 61 species had previously been reported as human piRNAs (piRNABank and piRBase), with 50 and 53 species present in the normal and PIWIL4 knockdown MDA-MB-231 cells, respectively, representing 1% and 2% of the total small RNAs from the normal and knockdown cells.

To search for piRNAs, small RNAs were selected in the piRNA size range (24-32 nucleotides) for further analysis. Totally, 98,139 species of small RNAs were in this fraction from MDAMB-231 cells without PIWIL4 knockdown and 55,624 species were in this fraction from these cells with PIWIL4 knockdown. Among them, 61 species had previously been reported as human piRNAs (piRNABank and piRBase), with 50 and 53 species present in the normal and PIWIL4 knockdown MDA-MB-231 cells, respectively, representing 1% and 2% of the total small RNAs from the normal and knockdown cells (FIG. 6C).

The identification of these known piRNAs indicated with reasonable confidence that at least some of the remaining 24- to 32-nucleotide small RNAs were piNRAs. However, these small RNA did not show the enrichment at either the 5' first position for U that was a signature of primary piRNA or at the 5' 10th position for A that was a signature of secondary piRNA (FIG. 6D). This could reflect that some of the small RNAs were not piRNAs. Alternatively, the signature may not be obvious because of the small number of species.

Figure 6E:
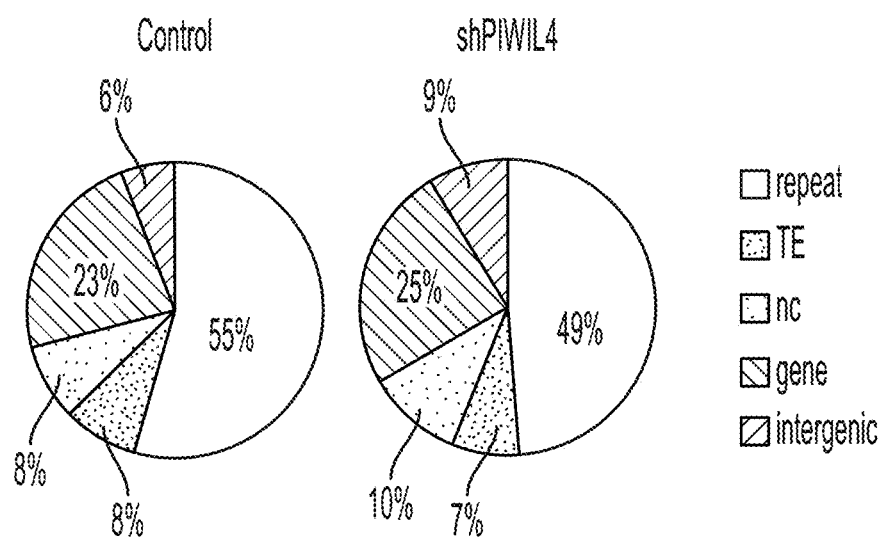
FIG. 6E depicts a graph showing results of the small RNAs mapped onto the genome whereby it was found that they corresponded to DNA repeats, transposons, intergenic sequences, and genes at proportions one would expect from piRNAs.

To further search for sequence features of these small RNAs that may help distinguish between the two possibilities, these small RNAs were mapped onto the genome and it was found that they corresponded to DNA repeats, transposons, intergenic sequences, and genes at proportions one would expect from piRNAs (FIG. 6E). These analyses supported the conclusion that at least some of the small RNAs were likely piRNAs. These data indicated that these small RNAs may be called putative piRNAs. Combined data on the known piRNAs and putative piRNAs indicated that the MDA-MB-231 cells expressed a small number of piRNAs.

Figure 6F:
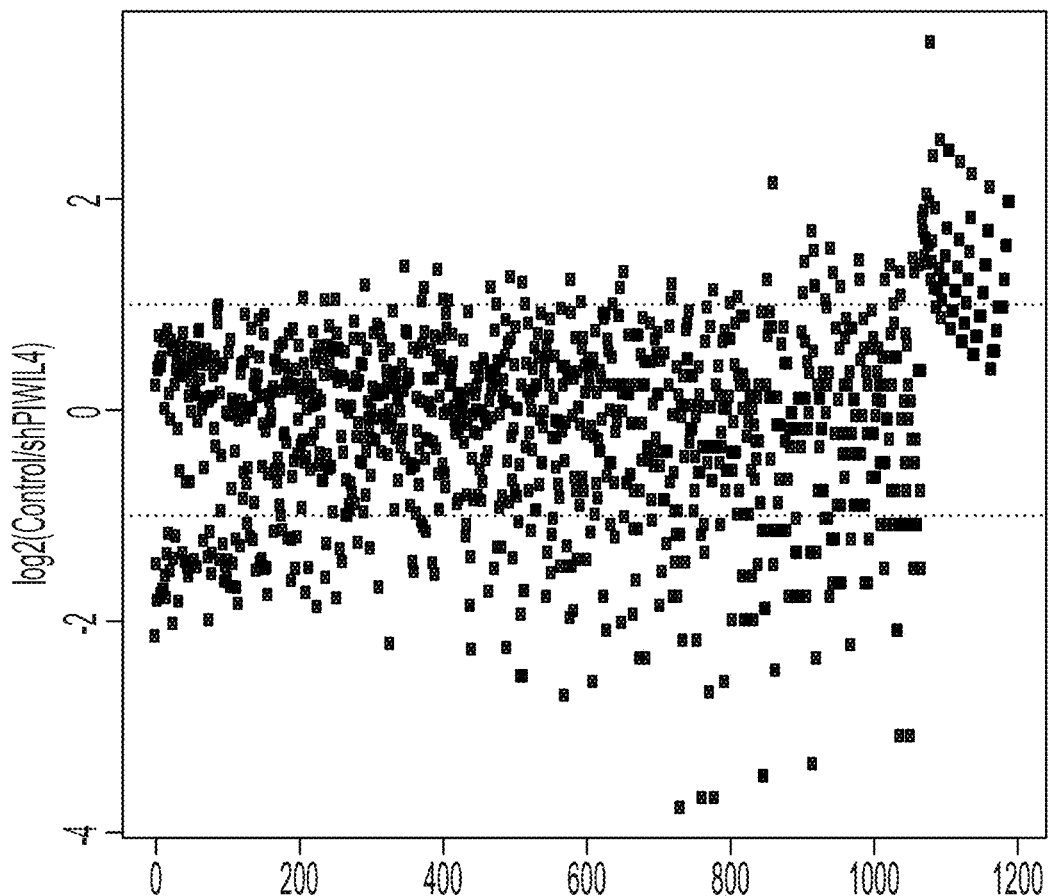
FIG. 6F depicts the putative piRNAs examined by at least 10 mappable reads in both types of the cells. Of 1192 such piRNA candidates, only 333 showed 2-fold or greater changes in abundance.

To assess how much of the expression of the putative piRNAs was affected by PIWIL4 knockdown, 24 known piRNAs (of the 61 known ones) were examined that have at least 10 mappable reads in either normal or knockdown samples. Only three hada 2-fold or more decrease in PIWIL4 knockdown cells, and only one had a more than 2-fold increase, colored in red and blue, respectively, in Table 8. The putative piRNAs were then examined with at least 10 mappable reads in both types of the cells. Of 1192 such piRNA candidates, only 333 showed 2-fold or greater changes in abundance (FIG. 6F). These combined data on the known piRNAs and putative piRNAs indicated that the piRNA expression is not much affected by reducing the PIWIL4 level.

TABLE 8

24-to-32 nt small RNAs that have been reported as piRNAs in piRNABank or piRBase

| sequence | SEQ ID NO: | size | Control Reads | sh PIWIL4 Reads | shPIWIL4/ Control ratio |
|---|---|---|---|---|---|
| GGCCGTGATCGTATAGTGGTTAGTACT** | 3 | 27 | 1026 | 422 | 0.484918803 |
| GATTATGATGATGCCTTAACACTGACT | 4 | 27 | 747 | 631 | 0.995893028 |
| AGCCCTGATGATGCCCACTCCTGAGC | 5 | 26 | 474 | 617 | 1.534654994 |
| CCCCCCACTGCTAAATTTGACTGGCT | 6 | 26 | 386 | 486 | 1.484406677 |
| CCCCCCACTGCTAAATTTGACTGG | 7 | 24 | 298 | 355 | 1.404481502 |
| CCCCCCACTGCTAAATTTGACTGGCTA | 8 | 27 | 249 | 275 | 1.30207884 |
| CCCCCCACTGCTAAATTTGACTGGC | 9 | 25 | 247 | 311 | 1.48445614 |
| CCCCCCACTGCTAAATTTGACTGGT | 10 | 25 | 201 | 274 | 1.607157502 |
| CCCCCACTGCTAAATTTGACTGGC | 11 | 24 | 143 | 147 | 1.211951476 |
| CCCCCACTGCTAAATTTGACTGGCT | 12 | 25 | 97 | 114 | 1.385597374 |
| CTGAGCAACATAGCGAGACCCCGTCTCTA | 13 | 29 | 92 | 57 | 0.73045079 |
| CCCCCACTGCTAAATTTGACTGGCTA | 14 | 26 | 79 | 82 | 1.223744338 |
| CCCCCACTGCTAAATTTGACTGGT | 15 | 24 | 65 | 84 | 1.523596141 |
| GCCTGAGCAACATAGCGAGACCCCGTCTCTA | 16 | 31 | 60 | 45 | 0.884229903 |
| GGCCGTGATCGTATAGTGGTTAGTACTC** | 17 | 28 | 57 | 17 | 0.351623587 |
| ATGCAGTGTGGAACACAATGAACTGAAC | 18 | 28 | 53 | 62 | 1.379176201 |
| GGCCGTGATCGTATAGTGGTTAGTAC | 19 | 26 | 46 | 26 | 0.666376159 |
| GGCCGTGATCGTATAGTGGTTAGTACTCTG | 20 | 30 | 29 | 22 | 0.894393465 |

TABLE 8-continued 24-to-32 nt small RNAs that have been reported as piRNAs in piRNABank or piRBase

| sequence | SEQ ID NO: | size | Control Reads | sh PIWIL4 Reads | shPIWIL4/ Control ratio |
|---|---|---|---|---|---|
| CCCCCCACTG CTAAATTTGA CTGGTT | 21 | 26 | 27 | 45 | 1.96495534 |
| CCCCACTGCT AAATTTGACT GGCT | 22 | 24 | 23 | 13 | 0.666376159 |
| AGCCTGAGCA ACATAGCGAG ACCCCGTCTC TA | 23 | 32 | 21 | 18 | 1.010548461 |
| GCCTGAGCAA CATAGCGAGA CCCCGTCTCT | 24 | 30 | 15 | 10 | 0.785982136 |
| CCTGAGCAAC ATAGCGAGAC CCCGTCTC T** | 25 | 29 | 10 | 2 | 0.235794641 |
| TTCACTGATG AGAGCATTGT TCTGAGC* | 26 | 27 | 10 | 22 | 2.593741049 |
| GTTCACTGAT GAGAGCATTG TTCTGAGC | 27 | 28 | 9 | 10 | 1.309970227 |
| CCCCCACTGC TAAATTTGAC TGGTT | 28 | 25 | 9 | 8 | 1.047976181 |
| CCCACCCAGG GACGCGTGGT GACTTT | 29 | 26 | 6 | 4 | 0.785982136 |
| ATGCAGTGTG GAACACAATG AACTGAA | 30 | 27 | 6 | 2 | 0.392991068 |
| TGCAGTGTGG AACACAATGA ACTGAAC | 31 | 27 | 4 | 6 | 1.768459806 |
| CACTGATGAG AGCATTGTTC TGAGC | 32 | 25 | 2 | 6 | 3.536919612 |
| AGCCTGAGCA ACATAGCGAG ACCCCGTCTC T | 33 | 31 | 4 | 4 | 1.178973204 |
| TTGCAAGCAA CACTCTGTGG CAGATGATC | 34 | 29 | 4 | 2 | 0.589486602 |
| GTAGTGCGCT ATGCCGATCG GGTGTC | 35 | 26 | 1 | 2 | 2.357946408 |
| GTTCACTGAT GAGAGCATTG TTCTGAGCCA | 36 | 30 | 1 | 2 | 2.357946408 |
| TTAAGGGGAA CGTGTGGGCT ATTTAGG | 37 | 27 | 1 | 2 | 2.357946408 |
| TTGCAAGCAA CACTCTGTGG CAGATGA | 38 | 27 | 1 | 2 | 2.357946408 |
| TGGAAAGGAT GAAGAGCTGA CTGATG | 39 | 26 | 4 | 1 | 0.294743301 |
| CCCCCTTTTA AAAGCACTCA ATGGGCC | 40 | 27 | 3 | 1 | 0.392991068 |
| GGTGCTGATG ACACCCACTG GCTGAAC | 41 | 27 | 3 | 1 | 0.392991068 |
| GATCAGTAGT GGGATCGCGC CTGTGAAT | 42 | 28 | 1 | 1 | 1.178973204 |
| TGATCAGTAG TGGGATCGCG CCTGTG | 43 | 26 | 1 | 1 | 1.178973204 |
| TGTAGTGCGC TATGCCGATC GGGTGT | 44 | 26 | 1 | 1 | 1.178973204 |
| GTAGTGCGCT ATGCCGATCG GGTGTCC | 45 | 27 | 5 | 0 | 0 |
| GTAGTGCGCT ATGCCGATCG GGTGT | 46 | 25 | 3 | 0 | 0 |
| TTGCAAGCAA CACTCTGTGG CAGATGAT | 47 | 28 | 2 | 0 | 0 |
| AGTGCGCTAT GCCGATCGGG TGTCC | 48 | 25 | 1 | 0 | 0 |
| TCAGTAGTGG GATCGCGCCT GTGAAT | 49 | 26 | 1 | 0 | 0 |
| TCATACCATA TGCGTGTCTC CAAAGT | 50 | 26 | 1 | 0 | 0 |
| TCGCCGTGAT CGTATAGTGG TTAGTACTCT G | 51 | 31 | 1 | 0 | 0 |
| TGTAAAAGAC GTGAACAGC AGGAGT | 52 | 26 | 1 | 0 | 0 |
| TGGAAAGGAT GAAGAGCTGA CTGATGG | 53 | 27 | 0 | 3 | NA |
| GCAGTGTGGA ACACAATGAA CTGAAC | 54 | 26 | 0 | 2 | NA |
| TGATCAGTAG TGGGATCGCG CCTGTGAAT | 55 | 29 | 0 | 2 | NA |

TABLE 8-continued 24-to-32 nt small RNAs that have been
reported as piRNAs in piRNABank or piRBase

| sequence | SEQ ID NO: | size | Control Reads | sh PIWIL4 Reads | shPIWIL4/ Control ratio |
|---|---|---|---|---|---|
| AGCATTGGTG GTTCAGTGGT AGAATTCTCG C | 56 | 31 | 0 | 1 | NA |
| CAGTGTGGAA CACAATGAAC TGAAC | 57 | 25 | 0 | 1 | NA |
| CTGCAATGAT GAAAATGTAG CTACTGAGC | 58 | 29 | 0 | 1 | NA |
| GAGCATGGTA ATGGATTTAT GGTGGGTCCT T | 59 | 31 | 0 | 1 | NA |
| GGAAAGGATG AAGAGCTGAC TGATGG | 60 | 26 | 0 | 1 | NA |
| TGCGCGACAT CAAGGAGAAG CTGTGCTA | 61 | 28 | 0 | 1 | NA |
| TGTAGTGCGC TATGCCGATC GGGTGTCC | 62 | 28 | 0 | 1 | NA |
| TTGGAGGATG AAACAAGGA ATCTGACT | 63 | 28 | 0 | 1 | NA |

*piRNAs up-regulated in shPIWIL4 cells
**piRNAs down-regulated in shPIWIL4 cells Discussion PIWI proteins have been reported to be ectopically expressed in diverse types of cancer (Kwon, C., et al (2014) Biochem. Biophys. Res. Commun. 446, 218-223, Chen, C., et al (2013) Cancer Biomark. 13, 315-321, Suzuki, R., et al (2012) Front. Genet. 3, 204, Wang, Y. et al (2012) Int. J. Clin. Exp. Pathol. 5, 315-325, and Siddiqi, S., and Matushansky, I. (2012) J. Cell. Biochem. 113, 373-380). However, most of these studies were at a correlative level. The role of PIWI expression in cancer remains unclear. As described herein, PIWIL4 was widely expressed in breast cancer samples from different patients and in multiple breast cancer cell lines. Moreover, using a TNBC line (MDA-MB-231) as a model, PIWIL4 expression promoted cancer cell survival, division, and, more significantly, migration. The study provided a definitive demonstration of the function of PIWI proteins in cancer cells.

Figure 7:
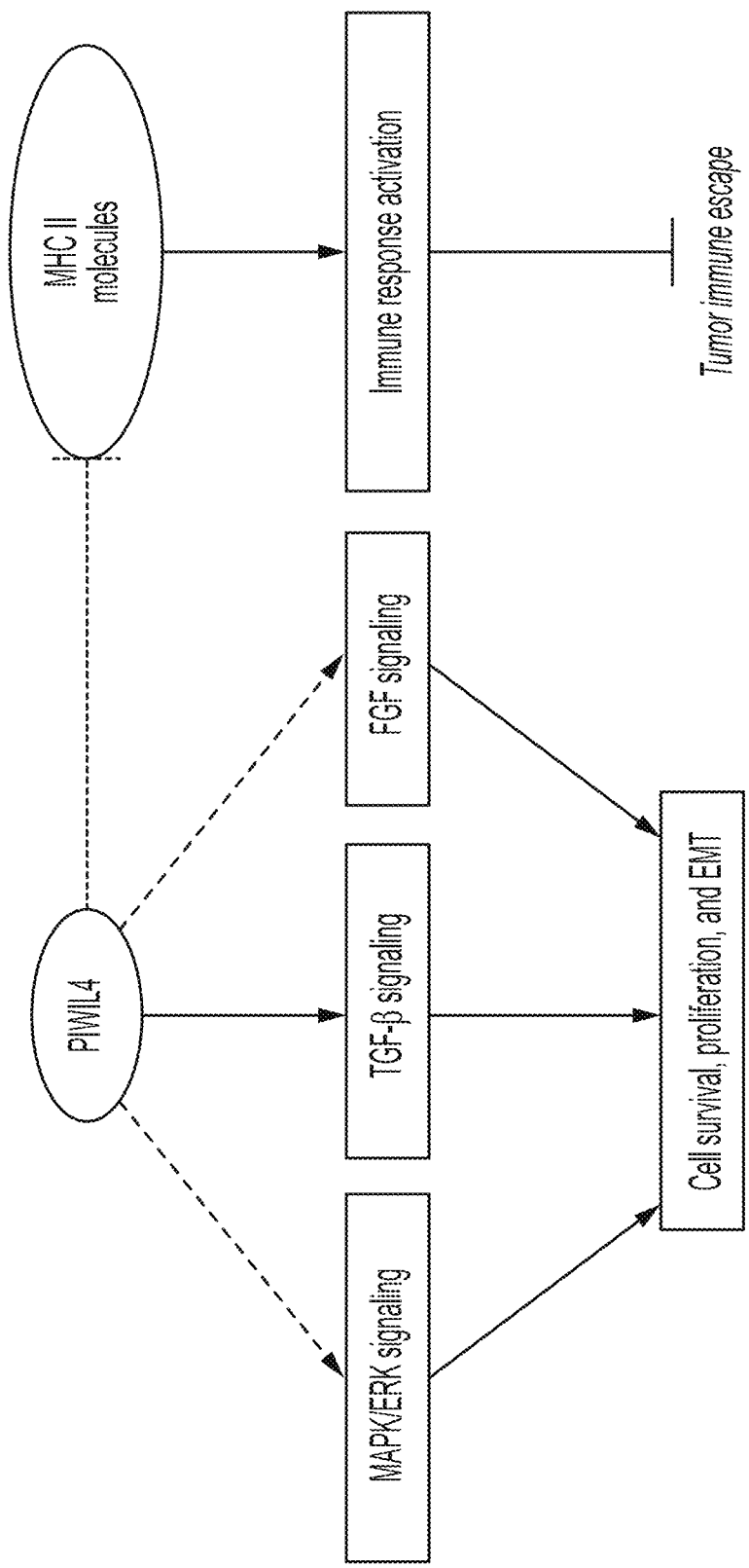
FIG. 7 depicts an image showing the transcriptome analysis which revealed that PIWIL4 achieved its function in the breast cancer cells partially by activating TGF-β, MAPK/ERK, and FGF signaling and repressing MHC class II expression.

Furthermore, the transcriptome analysis revealed that PIWIL4 achieved its function in the breast cancer cells partially by activating TGF-β, MAPK/ERK, and FGF signaling and repressing MEC class II expression (FIG. 7). The TGF-β, FGF, and MAPK-ERK pathways are well known to play key roles in cancer. Specifically, TGFβR1 and TGFβR2 are known as receptors of TGF and other signaling molecules. They then activate downstream signal molecules during epithelial-to-mesenchymal transition of tumor cells (Zavadil, J., and Böttinger, E. P. (2005) Oncogene 24, 5764-5774). Some researchers suggested that the expression of FGF4 and FGFR2 in ovarian cancer stemlike cells/cancer-initiating cells promoted their tumor initiation capacity (Yasuda, K., et al (2014) Lab. Invest. 94, 1355-1369). The mass spectrometry results showed that PIWIL4 promoted the TGF-β and FGF signaling pathways in the breast cancer cell line MDA-MB-231, which linked PIWIL4 function to these important signaling pathways. In addition, the transcriptome analysis demonstrated that PIWIL4 also upregulated the MAPK-ERK signaling pathway (FIG. 11A). These findings revealed a new dimension of regulation of TGFβ and FGF signaling in cancer formation. The PIWIL4 regulation of these classic cancer signaling pathways provides an intellectual framework for further investigation of how PIWIL4 promotes breast cancer cell migration, survival, and proliferation through these pathways It is intriguing to see that PIWIL4 also suppressed the expression of MEC class II genes. Tumorigenesis is a complex process involving not only signaling but also tumor immune escape pathways. MHC class II molecules are constitutively expressed in professional antigen-presenting cells, which are an essential part of cell-mediated immunity, but may also be induced on other cells by interferon γ (Ting, J. P., and Trowsdale, J. (2002) Cell 109, S21-33). The suppression of MEC class II genes might help cancer cells avoid immune recognition and reaction by the T cell pathway. PIWI proteins have multiple roles in the piRNA pathway. They participate in piRNA biogenesis in germ cells and represses transposon activity by affecting local epigenetic states and transcription (Juliano, C et al (2011) Annu. Rev. Genet. 45, 447-469). Correspondingly, piRNAs have important roles in mRNA regulation in the mouse by rendering targeting specificity (Watanabe, T., and Lin, H. (2014) Mol. Cell 56, 18-27, and Watanabe, T., et al (2015) Genome Res. 25, 368-380). Furthermore, some previous researchers suggested that piRNAs have independent functions, such as piR-823 having a role in breast cancer (Yan, H., et al (2015) Leukemia 29, 196-206). The analysis described herein indicated that a small number of piRNAs were expressed in MDAMB-231 cells. This raised the possibility that PIWIL4 worked with piRNA to achieve its function. Further isolation of the PIWIL4-piRNA complex, identification of their regulatory targets, and analysis of their regulatory effect on the targets should shed light on how PIWI-mediated mechanisms function in cancer development.

Materials and Methods

Cell Culture and Clinical Samples

MDA-MB-231, MDAMB-435, MDA-MB-468, and MDA-MB-453 cells were cultured in L-15 medium (Leibovitz, Sigma, L1518-500 ML) supplemented with 10% fetal bovine serum and incubated at 37° C. without $CO_2$. BT474 and 4T1 cells were cultured in RPMI 1640 medium (Life Technologies, 61870036) supplemented with 10% fetal bovine serum, and MCF-10A cells were cultured in MEBM medium (Lonza, CC-3151) supplemented with 10% bovine calf serum, and these three cell lines were incubated at 37° C. with 5% $CO_2$.

20 pairs of clinical samples were purchased from the tissue bank of the Institute of Health Sciences, Chinese Academy of Sciences. The local ethics committee approved the study, and the regulations of this committee were followed.

RNA Extraction and Quantitative Real-Time PCR

Total RNA was isolated using TRIzol (Invitrogen) according to the protocol of the manufacturer. For reverse transcription, 1 µg of RNA reverse transcriptase and the ABI high-capacity kit (Life Technologies, 4368814) were used. Real-time PCR reactions were performed according to the protocol of the Bio-Rad real-time PCR system (iQTM SYBR Green Supermix and CFX96™ real-time system). Primers of GAPDH were designed as the real-time PCR control. Quantitative PCR primers are listed in Table 1A and Table 1B (Soufla, G. et al (2005) *Cancer Lett.* 221, 105-118, and Marek, L., et al (2009) *Mol. Pharmacol.* 75, 196-207).

TABLE 1A

Primers used for qRT-PCR

| Primer set | SEQ ID NO | Oligonucleotide sequences (5'-3') | Primer annealing temperature (° C.) |
|---|---|---|---|
| PIWLI1 | 64 (F): | ACGCTGCATATTTCAGGATAGA | 60 |
|  | 65 (R): | GACAGTGACAGATTTGGCTCTC |  |
| PWIL2 | 66 (F): | TTGTGGACAGCCTGAAGCTA | 60 |
|  | 67 (R): | CCATCAGACACTCCATCACG |  |
| PIWIL4 | 68 (F): | AATGCTCGCTTTGAACTAGAGAC | 60 |
|  | 69 (R): | ATTTTGGGGTAGTCCACATTAAATC |  |
| GAPDH | 70 (F): | GGCTGAGAACGGGAAGCTTGTCAT | 60/55 |
|  | 71 (R): | CAGCCTTCTCCATGGTGGTGAAGA |  |
| TGFBR1 | 72 (F): | TCGTCTGCATCTCACTCAT | 55 |
|  | 73 (R): | GATAAATCTCTGCCTCACG |  |
| TGFBR2 | 74 (F): | GCGGGAGCACCCCTGTGTC | 60 |
|  | 75 (R): | CCCGAGAGCCTGTCCAGATGC |  |
| TGFB1 | 76 (F): | ACCAACTATTGCTTCAGCTC | 55 |
|  | 77 (R): | TTATGCTGGTTGTACAGG |  |
| TGFB3 | 78 (F): | CCTTTCAGCCCAATGGAGAT | 55 |
|  | 79 (R): | ACACAGCAGTTCTCCTCCAA |  |
| FGFR2 | 80 (F): | CGCTGGTGAGGATAACAACACG | 60 |
|  | 81 (R): | TGGAAGTTCATACTCGGAGACCC |  |

TABLE 1B

Primers used for shRNA DNA oligos

| Primer set | SEQ ID NO: | Oligonucleotide sequences (5'-3') |
|---|---|---|
| sh-PIWIL4-1 | 82 | (F): GATCCCCCCAGTACCATGTGACATATTT CAAGAGAATATGTCACATGGTACTGGTTTTTA |
|  | 83 | (R): AGCTTAAAAACCAGTACCATGTGACATA TTCTCTTGAAATATGTCACATGGTACTGGGGG |
| sh-PIWIL4-2 | 84 | (F): GATCCCCCTGTATCGGACCTGAATCATT CAAGAGATGATTCAGGTCCGATACAGTTTTTA |
|  | 85 | (R): AGCTTAAAAACTGTATCGGACCTGAATC ATCTCTTGAATGATTCAGGTCCGATACAGGGG |
| sh-PIWIL4-3 | 86 | (F): GATCCCCCACGTAACGAATGGTATGATT CAAGAGATCATACCATTCGTTACGTGTTTTTA |
|  | 87 | (R): AGCTTAAAAACACGTAACGAATGGTATG ATCTCTTGAATCATACCATTCGTTACGTGGGG |

PIWIL4 cDNA Cloning

The PIWL4 cDNA primers were designed as follows: forward, 5'-CGCGGATCCATGAGTGGAAGAGCCCG-3'; reverse, 5'-CGCGGATCCTCACAGGTAGAAGAGATGG-3' (SEQ ID NOs 88 and 89, respectively). Total RNA was used for cDNA synthesis by SuperScript® III reverse transcriptase (Invitrogen, 18080044) according to the protocol of the manufacturer. The cDNA was used as a template for amplification by Phusion high-fidelity DNA polymerase (New England Biolabs, M0530L) in PCR and cloned into the pMDTM19-T vector by a cloning kit (Takara, 6013).

Western Blotting Analysis

Total proteins were extracted by radioimmunoprecipitation assay buffer (Santa Cruz Biotechnology, sc-24948) according to the protocol of the manufacturer. Samples were mixed (3:1) with 4× protein SDS-PAGE loading buffer (Takara, 9173) and heated at 100° C. for 10 min. The human testicular total protein lysate was purchased from Clontech (catalog no. 635309). 30 µg of protein was resolved by the TGX Fast Cast acrylamide kit, 7.5% or 10% (Bio-Rad, 1610173TA) at 120 V, and electrotransferred to a PVDF membrane (Merck/Millipore, IPVH00010) at 0.3 A for 1.5 h. The membrane was blocked with 5% Difco™ skim milk (BD Biosciences, 232100) at room temperature for 2 h, which was diluted with TBS (Bio-Rad, 1706435) supplemented with 0.1% Tween 20 (Santa Cruz Biotechnology, sc-29113). PIWIL4 antibody (Abcam, ab111714) was used at 1:1000 dilution. N-cadherin ntibody (Abcam, ab18203) at 1:1000 dilution, E-cadherin (Cell Signaling Technology, 3195S) at 1:1000 dilution, cleaved caspase-3 (Cell Signaling Technology, 9664) at 1:1000 dilution, p27 Kip1 (D69C12) XP® rabbit mAb (Cell Signaling Technology, 3686) at 1:1000 dilution, phospho-Smad (Ser-465/467) antibody (Cell Signaling Technology, 3101) at 1:1000 dilution, and β-Actin antibody (Cell Signaling Technology, 4970S) at 1:1000 dilution were used. A cell cycle/checkpoint antibody sampler kit (Cell Signaling Technology, 9917) was used for detecting cell cycle-dependent phosphorylation of CDC2 and CHK2.

PIWIL4 shRNA Knockdown Analysis

RNAi vector pSUPERpuro was purchased from Promega. Three short hairpin DNA sequences were designed as in Table 1B. The DNA sense and antisense sequences were annealed in a pairwise fashion and cloned into the pSUPERpuro vector.

MDA-MB-231 cells were transfected with Lipofectamine 2000 (Life Technologies, 11668019) according to the instructions of the manufacturer. Transfected cells were selected using 0.8 µg/ml puromycin. The silencing effect on the PIWIL4 gene was assessed by quantitative PCR and Western blotting analysis according to the aforementioned protocols.

Nuclear-Cytoplasmic Fractionation

Approximately $10^6$ cells were washed with PBS twice, followed by centrifugation at 1000×g for 3 min. The resulting supernatant was discarded. The pellet was added to 150-200 µl of buffer B (10 mM Hepes, 10 mM KCl, 2 mM $MgCl_2$, 0.1 mM EDTA, 0.2% Nonidet P-40, protease inhibitor, and 1 mMDTT), incubated on ice for 30 min, and centrifuged at 4° C. at 13,200 rpm for 6 min. Cytoplasmic proteins were collected as the supernatant to new tubes and stored at −80° C. until use. The nuclear pellet was washed with 500 µl of wash buffer (10 mM Hepes, 20 mM KCl, 2 mM $MgCl_2$, 0.1 mM EDTA, protease inhibitor, and 1 mM DTT) and centrifuged at 4° C. at 3000 rpm for 5 min. The supernatant was discarded, and the nuclear pellet was dissolved in 50-80 µl of extraction buffer (20 mM Hepes, 0.64 mM NaCl, 1.5 mM $MgCl_2$, 0.2 mM EDTA, 2.5% glycerol, protease inhibitor, and 1 mM DTT), vortexed for 15 s, incubated on ice for 30 min, vortexed for 10-15 s at 10-min intervals, and centrifuged at 4° C. and 13,200 rpm for 20 min. The supernatants, which contained nucleus proteins, were collected in new tubes and stored at −80° C. for later use. Separation of the cytoplasmic and nuclear fractions was verified by Western blotting for β-tubulin and TBP (Cell Signaling Technology, anti-β-tubulin and anti-TBP antibody).

Apoptosis Assay

Cancer cells were stained with the FITC Annexin V apoptosis detection kit I (BD Biosciences, 556547) according to the protocol of the manufacturer and analyzed early- and late-stage apoptosis by FACS (FACS Aria™ IIII, BDBiosciences).

Cell Death and Cell Proliferation Assays

Cells were mixed (1:1) with trypan blue solution, 0.4% (Gibco, 15250061), 100 of which was seeded on Countess chamber slides (Invitrogen, C10312) and counted with a Countess™ automated cell counter (Invitrogen, C10227). $2 \times 10^3$ cells/well were seeded in 96-well cell culture plates and 6-cm$^2$ dishes. Each sample had three repeats. Cell proliferation was determined using CellTiter 96® AQueous MTS (3-(4,5-dimethylthiazol-2-yl)-5-(3-carboxymethoxyphenyl)-2-(4-sulfophenyl)-2H-tetrazolium, inner salt) reagent powder (Promega, G1111) according to the instructions of the manufacturer. Absorbance at 490-nm wavelength was read using EnSpire® multimode plate readers (PerkinElmer Life Sciences), and clone formation was visualized by staining with crystal violet solution (Beyotime Biotechnology, C0121).

Wound Healing and Transwell Migration Assays $5 \times 10^4$ cells were seeded in a 96-well plate, and a wound was introduced with a wound maker kit (Essen Bioscience). Wounded monolayers were washed twice with PBS to remove non-adherent cells. Cells were cultured in 2% FBS for 48 h, and the wound healing tracks were recorded with an IncuCyte® Zoom live-cell analysis system (Essen Bioscience). The transwell assay was done using Corning FluoroBlok™ cell culture inserts (Falcon, 351152) according to the protocol of the manufacturer.

Immunofluorescence Microscopy $2 \times 10^5$ cells were seeded on a coverslip (Fisherbrand, 12-545-83) in a 24-well plate. After 24 h, cells were washed three times in 1×PBST (1% Tween 20 in phosphate-buffered saline, 5 min each time), fixed in 4% formaldehyde (paraformaldehyde powder, 95%, 158127-2.5 KG, Sigma) at room temperature for 15 min, incubated with 0.1% Triton X-100 (Santa Cruz Biotechnology, sc-29112) at room temperature for 15 min, washed in PBST three times (5 min each wash), blocked in 3% BSA at room temperature for 2 h, and washed in TBST again for 5 min. The cells were incubated with anti-PIWIL4 (Abcam, ab111714, 1:500 dilution) and antihDcpla (56-Y) antibodies (Santa Cruz Biotechnology, sc-100706, 1:500 dilution) in 3% BSA at 4° C. overnight with no primary antibody addition as a negative control. After incubation, cells were washed three times in 1×PBST, 5 min each time. FITC-conjugated AffiniPure goat anti-mouse IgG and IgM (heavy and light chain) (Jackson ImmunoResearch Laboratories, 115-095-044, 1:100 dilution) or Alexa Fluor 594-conjugated AffiniPure goat anti-rabbit IgG, Fc fragment-specific (Jackson ImmunoResearch Laboratories, 111-585-008, 1:500 dilution) were added and incubated at room temperature for 2 h, followed by a PBST wash once for 5 min. DAPI (Life Technologies, D1306, 1:5000 dilution) was then added to the PBST buffer and incubated at room temperature for 10 min, followed by three washes in PBST, 5 min each time. Coverslips were removed one at a time, and 1 drop of FluorPreserve™ (Merck/Millipore, 345787-25MLCN) was added, mounted them to the glass slide, pressed gently, sealed them with nail polish, and stored them at 4° C. overnight before confocal immunofluorescence microscopy (Zeiss, LSM710).

Mass Spectrometry and RNA Deep Sequencing $\sim 10^6$ MDAMB-231 cells or cells treated with shPIWIL4-1, shPIWIL4-2, or shPIWIL4-3 were collected, lysed in 200_1 of SDT lysis buffer (4% (w/v) SDS, 100 mM Tris/HCl (pH 7.6), and 0.1 M DTT), and then incubated at 95° C. for 3-5 min. Filter-aided proteome preparation was carried out according to the protocol detailed in below, under "Filter aided proteome preparation (FASP) and sequenced by Thermo Scientific Fusion with EASY-nLC 1000.

For RNA sequencing, $\sim 10^6$ MDA-MB-231 cells with or without shPIWIL4-3 treatment were collected. Total RNA was isolated using TRIzol (Invitrogen, 15596026) according to the protocol of the manufacturer. mRNAs and small RNAs were sequenced with an Illumina HiSeq3000 platform (Jing Neng Co., Shanghai, China). HTSeq software was used for the statistics of the original mRNA deep sequencing data of the control and shPIWIL4-3-treated samples. DESeq software was used to screen differentially expressed genes compared with the control ($p \leq 0.05$ or -fold change$\geq 2$).

Filter Aided Proteome Preparation (FASP)

In-gel digestion for mass spectrometry-based proteomics is extremely robust whereas in-solution digestion is more easily automated and minimizes sample handling. Filter aided proteome preparation (FASP), combines these advantages by completely solubilizing the proteome in sodium dodecyl sulfate (SDS), which is exchanged by urea on a standard filtration device. Peptides eluted after digestion on the filter were pure, allowing single run analysis of organelles and unprecedented depth of proteome coverage. Materials used included: SDT-lysis buffer: 4% (w/v) SDS, 100 mM Tris/HCl pH 7.6, 0.1M DTT, UA: 8 M urea (Sigma, U5128) in 0.1 M Tris/HCl pH 8.5, UB: 8 M urea (Sigma, U5128) in 0.1 M Tris/HCl pH 8.0, IAA solution: 0.05 M iodoacetamide in UA, Endoproteinase Lys-C from Wako Bioproducts (Richmond, Va.) Stock 5 pg/pl, Trypsin, Stock 0.4 pg/pl, 0.5M NaCl in water, ABC: 0.05M NH$_4$HCO$_3$ in water, Microcon YM-30 (Millipore, Cat. No. 42410) or Microcon YM-10 (Millipore, Cat. No. number 42407), 3M Empore HP Extraction disk cartridge (C18-SD); 7 mm/3 ml (Varian Cat. No. 12144002).

Cells and tissues were lysed in SDT-lysis buffer using 1:10 sample to buffer ratio for at 95° C. for 3-5 min. The DNA was sheared by sonication to reduce the viscosity of the sample. Before starting sample processing the lysate was clarified by centrifugation at 16,000×g for 5 min (Note: the tissues have to be homogenized with a blender in the lysis solution before heating, and avoid temperatures below 15° C. and potassium salts to avoid precipitation of concentrated SDS).

Sample processing: 1. Mix up to 30 pl of a protein extract with 200 pl of UA in the filter unit and centrifuge at 14,000×g for 40 min. 2. Add 200 pl of UA to the filter unit and centrifuge at 14,000×g for 40 min. 3. Discard the flow-through form the collection tube, 4. Add 100 pl IAA solution and mix at 600 rpm in thermo-mixer for 1 min and incubate without mixing for 5 min, 5. Centrifuge the filter units at 14,000×g for 30 min. 6 Add 100 pl of UB to the filter unit and centrifuge at 14,000×g for 40 min. Repeat this step twice. 7. Add 40 pl of UB with Lys-C (enzyme to protein ration 1:50) and mix at 600 rpm in thermo-mixer for 1 min 8. Incubate the units in wet chamber overnight. 9. Transfer the filter units to new collection tubes. 10 Add 120 pl ABC with trypsin (enzyme to protein ration 1:100) and mix at 600 rpm in thermo-mixer for 1 min. 11 Incubate the units at RT for 4 h. 12. Centrifuge the filter units at 14,000×g for 40 min.

13. Add 50 pl 0.5 M NaCl and centrifuge the filter units at 14,000×g for 20 min. 14 Acidify with CF₃COOH and desalt the filtrate.

Desalting of peptides: Small amounts of digest for direct LC-MS analysis can be desalted on StageTips, and large amounts of peptide mixtures have to be desalted on SPE cartridges according to the following protocol: 1. Place a 3 ml MILI-SPE Extraction disk cartridge (C18-SD) in and 15 ml conical tube, 2. 2. Add 1 ml of CH₃OH and centrifuge at 1,500×g for 1 min. 3. Add 0.5 ml of 0.1% CF₃COOH, 70% CH₃CN in water and centrifuge at 1,500×g for 1 min. 4. Add 0.5 ml of 0.1% CF₃COOH in water and centrifuge at 1,500×g for 1 min. 5 Load the filtrate (2.2 step 15) and centrifuge at 150×g for 3 min. 6 Add 0.5 ml of 0.1% CF₃COOH in water and centrifuge at 150×g for 3 min. 7. Transfer the cartridge to anew tube, add 0.5 ml 70% CH₃CN in water and centrifuge at 150×g for 3 min. 8. The eluate contains desalted peptides.

Yield determination: Concentration of the peptides was estimated by UV spectrometer assuming that 0.1% solution of vertebrate proteins has at 280 nm an extinction of 1.1 absorbance units (1 mg/ml solution has 1.1 au) (Winiewski J R, et al., (2009). *Nat Methods.* 6(5):359-62)

Gene Ontology and Pathway Analysis

A gene ontology and pathway analysis was conducted using an online tool. Gene ontology level 2 and 3 categories were selected for mRNA sequencing and mass spectrometry analysis, respectively.

Genome Mapping

The small RNA sequences were generated with Illumina HiSeq3000, and the linkers were trimmed off with the FASTX toolkit. Sequences were selected with sizes ranging from 12-43 nucleotides for analysis. The reference genome was human genome hg38. The gene annotation information was based on the Ensembl annotation. The miRNA annotation was based on version 21 of miRBase. Repeats and transposon annotation were based on RepeatMasker. Complete rRNA references were from the NCBI. One mismatch was allowed for mapping sequences against rRNA, tRNA, small nucleolar RNA, and small nuclear RNA.

Identification of Known piRNAs

Human known piRNAs in piRNABank and piRBase served as references to identify known piRNAs. Only the small RNAs that had an identical sequence to these reference piRNA sequences were defined as known piRNAs.

Effect of PIWIL4 Knockdown on Known piRNAs

The abundance of piRNAs was scaled according to the total mapped reads for comparison across different conditions. The shPIWIL4 treated to-nontreated control ratio was calculated to measure the effect of PIWIL4 knockdown on piRNAs. In total, ~200 small RNAs annotated as piRNAs in piRNABank and piRBase were detected, of which ~20 were affected (fold change≥2 or ≤½) when PIWIL4 was knocked down.

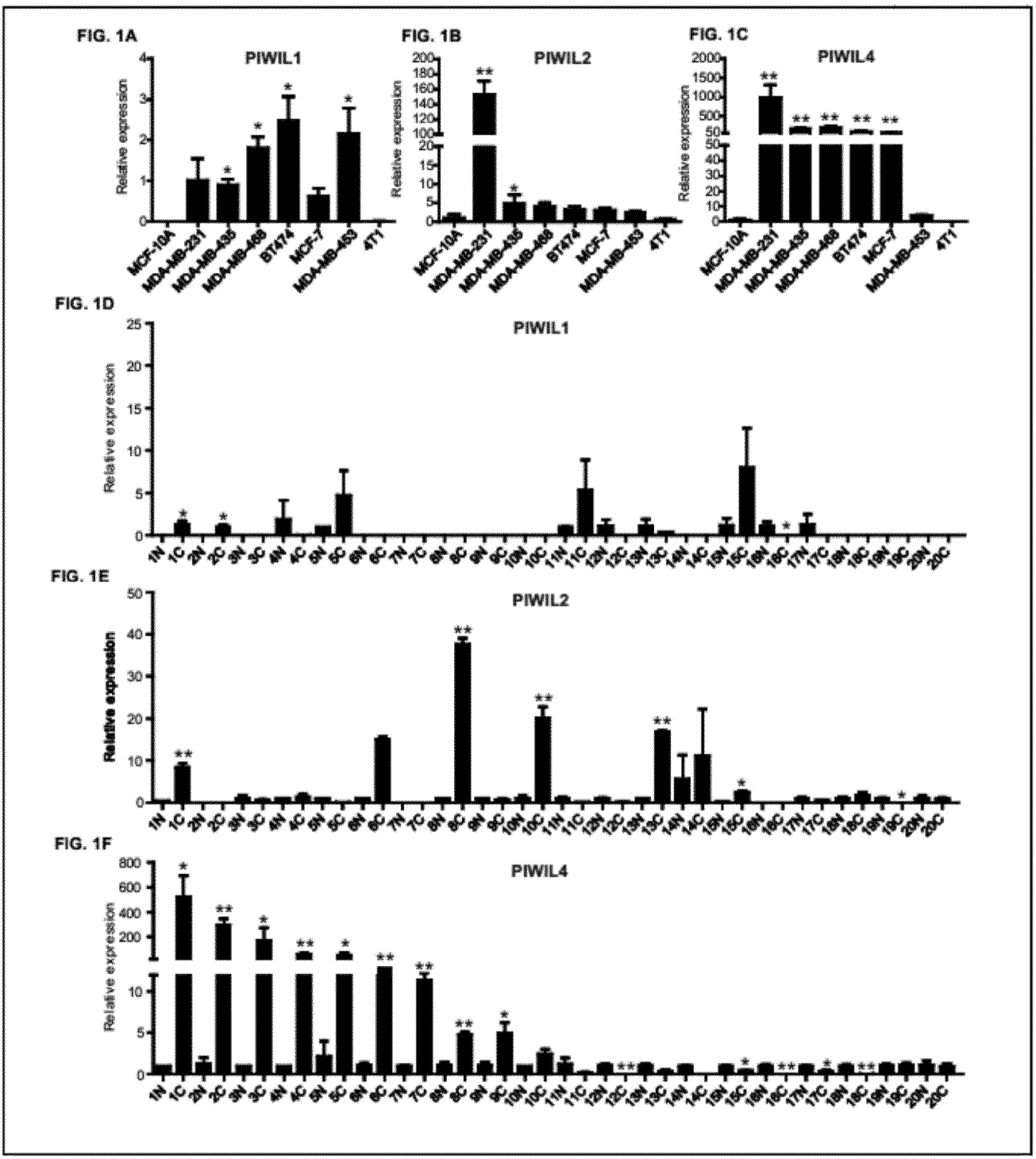

What is claimed is:

1. A method for treating breast cancer in a subject in need thereof, the method comprising reducing P-element induced wimpy testis-like protein 4 (PIWIL4) expression and/or activity in cells of the cancer by administering a PIWIL4-specific inhibitory nucleic acid to the subject.

2. The method of claim 1, wherein PIWIL4 expression and/or activity is reduced by the PIWIL4-specific inhibitory nucleic acid.

3. The method of claim 2, wherein the inhibitory nucleic acid is an RNA interfering agent (RNAi).

4. The method of claim 1, wherein the breast cancer is a triple negative breast cancer.

5. The method of claim 4, wherein the method comprises administering at least one additional therapeutic agent in combination with the PIWIL4-specific inhibitory nucleic acid.

6. The method of claim 1, further comprising detecting the expression of PIWIL4 in the cells of the cancer.

* * * * *

UNITED STATES PATENT AND TRADEMARK OFFICE
CERTIFICATE OF CORRECTION

Page 1 of 2

PATENT NO. : 10,787,666 B2
APPLICATION NO. : 16/469816
DATED : September 29, 2020
INVENTOR(S) : Haifan Lin et al.

It is certified that error appears in the above-identified patent and that said Letters Patent is hereby corrected as shown below:

On the Title Page

Under abstract "6 Claims, 27 Drawing Sheets" should read --6 Claims, 28 Drawing Sheets--.

In the Drawings

Add omitted Figures (Fig. 1A-1F) as shown on the attached drawing sheet.

Signed and Sealed this
Eighth Day of June, 2021

Drew Hirshfeld
*Performing the Functions and Duties of the
Under Secretary of Commerce for Intellectual Property and
Director of the United States Patent and Trademark Office*